(12) United States Patent
Yang et al.

(10) Patent No.: US 10,371,708 B2
(45) Date of Patent: Aug. 6, 2019

(54) METAL ION SENSORS AND METHODS OF DETECTING METAL IONS

(71) Applicant: Georgia State University Research Foundation, Inc., Atlanta, GA (US)

(72) Inventors: Jenny Jie Yang, Marietta, GA (US); Shen Tang, Atlanta, GA (US); You Zhuo, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 448 days.

(21) Appl. No.: 14/908,684

(22) PCT Filed: Aug. 6, 2014

(86) PCT No.: PCT/US2014/049927
§ 371 (c)(1),
(2) Date: Jan. 29, 2016

(87) PCT Pub. No.: WO2015/021143
PCT Pub. Date: Feb. 12, 2015

(65) Prior Publication Data
US 2016/0245831 A1    Aug. 25, 2016

Related U.S. Application Data

(60) Provisional application No. 61/862,663, filed on Aug. 6, 2013, provisional application No. 61/923,252, filed on Jan. 3, 2014.

(51) Int. Cl.
| | |
|---|---|
| *G01N 33/84* | (2006.01) |
| *C07K 14/47* | (2006.01) |
| *C07K 14/43* | (2006.01) |
| *G01N 21/64* | (2006.01) |
| *G01N 33/58* | (2006.01) |
| *C07K 14/435* | (2006.01) |

(52) U.S. Cl.
CPC ....... *G01N 33/84* (2013.01); *C07K 14/43595* (2013.01); *C07K 14/4728* (2013.01); *G01N 21/6428* (2013.01); *G01N 33/582* (2013.01); *C07K 2319/04* (2013.01); *C07K 2319/60* (2013.01); *G01N 2021/6441* (2013.01)

(58) Field of Classification Search
None
See application file for complete search history.

(56) References Cited

U.S. PATENT DOCUMENTS

| 2005/0196768 A1 | 9/2005 | Campbell et al. |
| 2010/0137158 A1 | 6/2010 | Shusta et al. |
| 2011/0097731 A1 | 4/2011 | Oertner et al. |

FOREIGN PATENT DOCUMENTS

| WO | 2006020550 A2 | 2/2006 |
| WO | 2006024041 A2 | 3/2006 |
| WO | 2008046029 A2 | 4/2008 |
| WO | 2012054648 A2 | 4/2012 |

OTHER PUBLICATIONS

International Search Report for PCT/US2014/049927 dated Jan. 12, 2015.
Nigo, JT et al., "Mutant Methionyl-tRNA Synthetase From Bacteria Enables Site-Selective N-terminal Labeling of Proteins Expressed in Mammalian Cells", PNAS. Mar. 26, 2013, vol. 110, No. 13; pp. 4992-4997; Supporting Information. DOI: 10.1073/pnas.1216375110/-/DCSupplemental; Supporting Information, figure S3A, p. 3, third paragraph; p. 3, fourth paragraph; GenBank Accession No. KC608723.1.
Clapham, D.E., Calcium signaling. Cell, 2007. 131(6): p. 1047-58.
Berridge, M.J., M.D. Bootman, and P. Lipp, Calcium—a life and death signal. Nature, 1998. 395(6703): p. 645-8.
Berridge, M.J., Neuronal calcium signaling. Neuron, 1998.21(1): p. 13-26.
Bers, D.M. and T. Guo, Calcium signaling in cardiac ventricular myocytes. Ann N Y Acad Sci, 2005. 1047: p. 86-98.
Spitzer, C.C., Calcium: first messenger. Nat Neurosci, 2008. 11(3): p. 243-4.
Baylor, S.M. and S. Hollingworth, Sarcoplasmic reticulum calcium release compared in slow-twitch and fast-twitch fibres of mouse muscle. J Physiol, 2003. 551(Pt 1): p. 125-38.
Bean, B.P., The action potential in mammalian central neurons. Nat Rev Neurosci, 2007. 8(6): p. 451-65.

(Continued)

*Primary Examiner* — Suzanne M Noakes
(74) *Attorney, Agent, or Firm* — Thomas|Horstemeyer, LLP

(57) ABSTRACT

A method for constructing an metal ion binding motif by identifying an metal ion binding peptide that binds an metal ion with specificity, ascertaining at least a portion of a nucleic acid sequence encoding the metal ion binding peptide, tailoring the nucleic acid sequence encoding the metal ion binding peptide into an metal ion binding site, identifying a host protein and a relevant portion of the nucleic acid sequence of the host protein, operatively linking the tailored nucleic acid sequence encoding the metal ion binding peptide and the host protein nucleic acid sequence into an metal ion binding motif sequence, and expressing metal ion binding motif sequence, in which the nucleic acid sequence encoding the metal ion binding peptide is tailored so as to achieve the metal ion binding motif with a desired specificity for the metal ion. Also, the proteins encoded by the metal ion binding motif sequence as constructed by the method.

9 Claims, 33 Drawing Sheets
Specification includes a Sequence Listing.

(56) References Cited

OTHER PUBLICATIONS

Locknar, S.A., et al., Calcium-induced calcium release regulates action potential generation in guinea-pig sympathetic neurones. J Physiol, 2004. 555(Pt 3): p. 627-35.
Sandler, V.M. and J.G. Barbara, Calcium-induced calcium release contributes to action potential-evoked calcium transients in hippocampal CA1 pyramidal neurons. J Neurosci, 1999. 19(11): p. 4325-36.
Borst, J.G. and B. Sakmann, Effect of changes in action potential shape on calcium currents and transmitter release in a calyx-type synapse of the rat auditory brainstern. Philos Trans R Soc Lond B Biol Sci, 1999. 354(1381): p. 347-55.
Fill, M. and J.A. Copello, Ryanodine receptor calcium release channels. Physiol Rev, 2002. 82(4): p. 893-922.
Okayama, H. and P. Berg, High-efficiency cloning of full-length cDNA. Mol Cell Biol, 1982. 2(2): p. 161-70.
Okayama, H. and P. Berg, A cDNA cloning vector that permits expression of cDNA inserts in mammalian cells. Mol Cell Biol, 1983. 3(2): p. 280-9.
Meur, G., et al., Targeting and retention of type 1 ryanodine receptors to the endoplasmic reticulum. J Biol Chem, 2007. 282(32): p. 23096-103.
Shaner, N.C., et al., Improving the photostability of bright monomeric orange and red fluorescent proteins. Nat Methods, 2008. 5(6): p. 545-51.
Schreiber, G. and A.R. Fersht, Rapid, electrostatically assisted association of proteins. Nat Struct Biol, 1996. 3(5): p. 427-31.
Radic, Z., et al., Electrostatic influence on the kinetics of ligand binding to acetylcholinesterase. Distinctions between active center ligands and fasciculin. J Biol Chem, 1997. 272(37): p. 23265-77.
Scott, A.M., C.E. Antal, and A.G. Newton, Electrostatic and hydrophobic interactions differentially tune membrane binding kinetics of the C2 domain of protein kinase Calpha. J Biol Chem, 2013. 288(23): p. 16905-15.
Shu, X., et al., Novel chromophores and buried charges control color in mFruits. Biochemistry, 2006. 45(32): p. 9639-47.
Seefeldt, B., et al., Fluorescent proteins for single-molecule fluorescence applications. J Biophotonics, 2008. 1(1): p. 74-82.
Mizushima, et al., "pEF-BOS, a powerful mammalian expression vector", 1990, Nucleic Acids Research, vol. 18, No. 17, p. 5322.
Hink et al., "Practical Use of Corrected Fluorescence Excitation and Emission Spectra of Fluorescent Proteins in Forster Resonance Energy Transfer (FRET) Studies", (2003) J. Fluoresc. 13: 185-188.
Carlson, et al., "Circular permutated red fluorescent proteins and calcium ion indicators based on mCherry", Protein Engineering, Design & Selection, vol. 26, No. 12, pp. 763-772, 2013.
Yang, W., et al., Rational design of a calcium-binding protein. J Am Chem Soc, 2003. 125(20): p. 6165-71.
Chinese Office Action for CN Application No. 2014800551977 dated Jun. 26, 2017.
Chinese Office Action for CN 2014800551977 dated Nov. 28, 2016.
Extended Supplementary European Search Report for EP 14 83 4333 dated Feb. 28, 2017.
Supplementary Partial European Search Report for EP 14 83 4333 dated Oct. 28, 2016.
Tang, et al., "Design and application of a class of sensors to monitor Ca2+ dynamics in high Ca2+ concentration cellular compartments", PNAS, Sep. 27, 2011, vol. 108, No. 39, pp. 16265-16270.
Richmond, et al., "Engineered Metal Binding Sites on Green Fluorescence Protein", Biochemical and Biophysical Research Communications, 2000, vol. 268, No. 2, pp. 462-465.

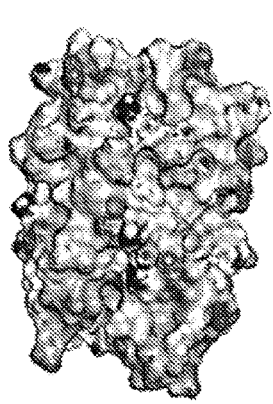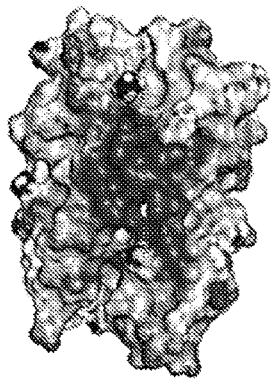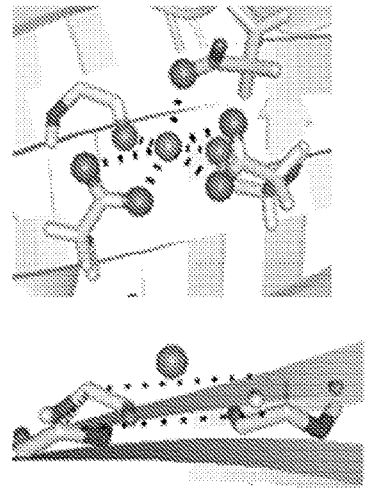
Fig. 1C
Fig. 1D
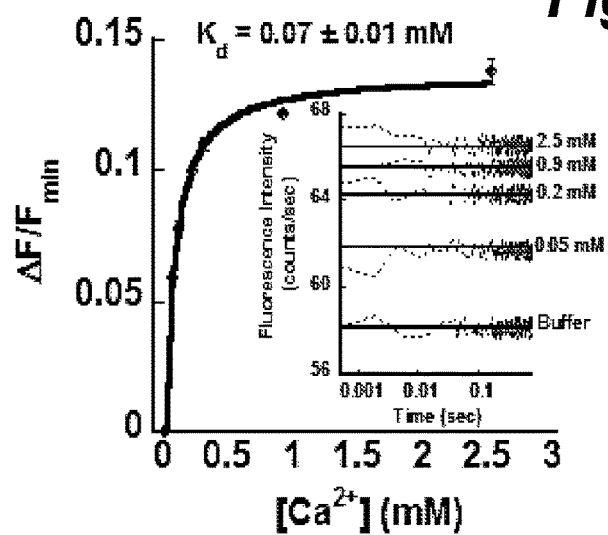
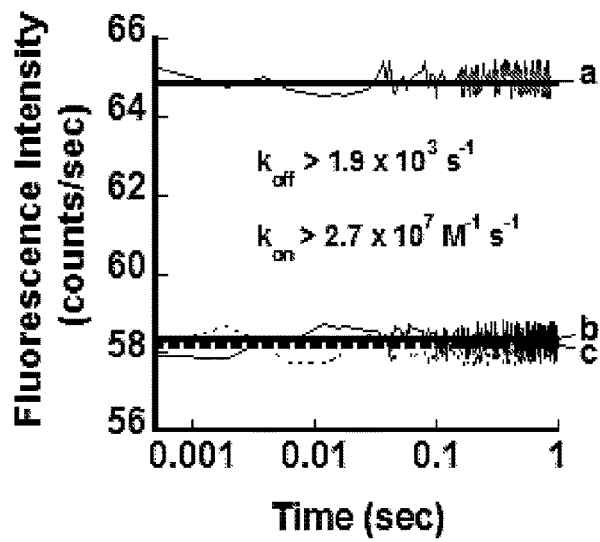
Fig. 1E

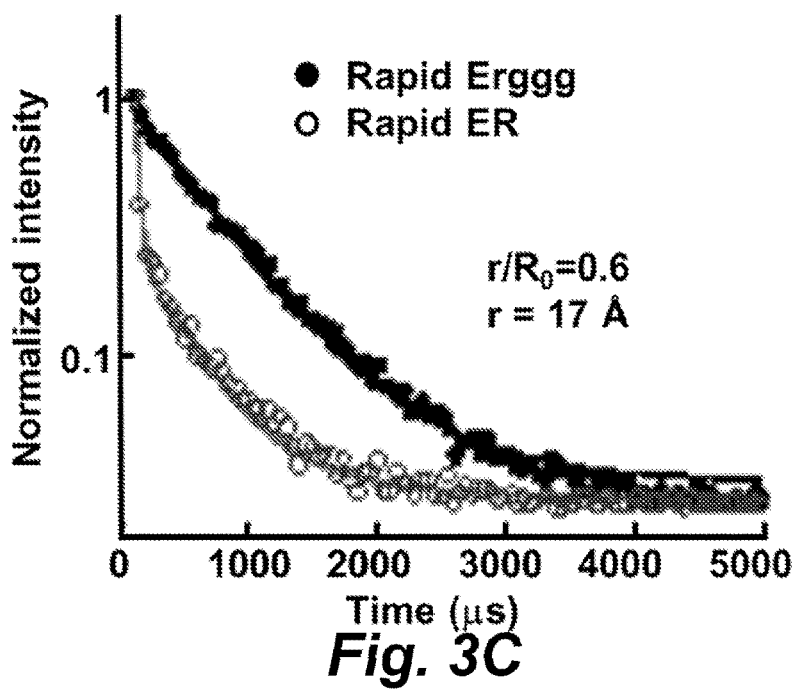
*Fig. 3C*
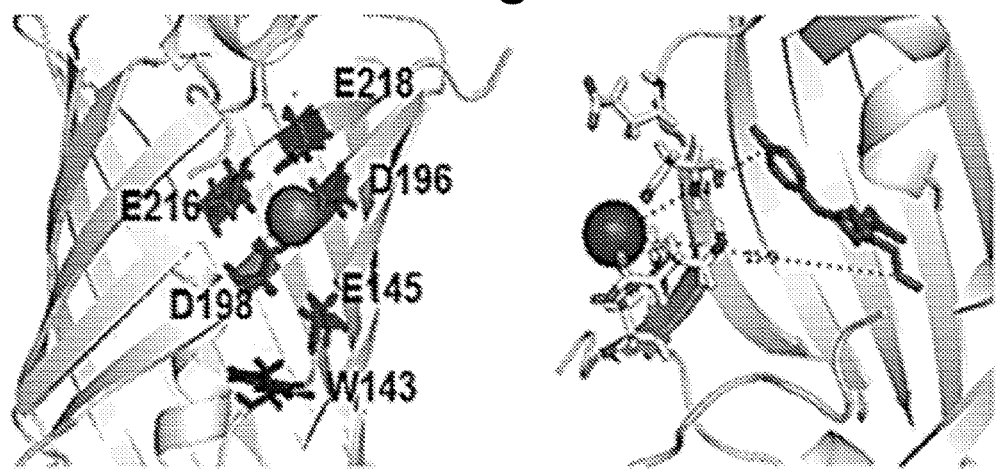
*Fig. 3D*          *Fig. 3E*
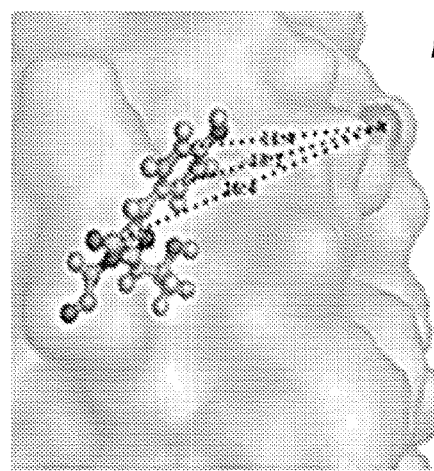
*Fig. 3F*

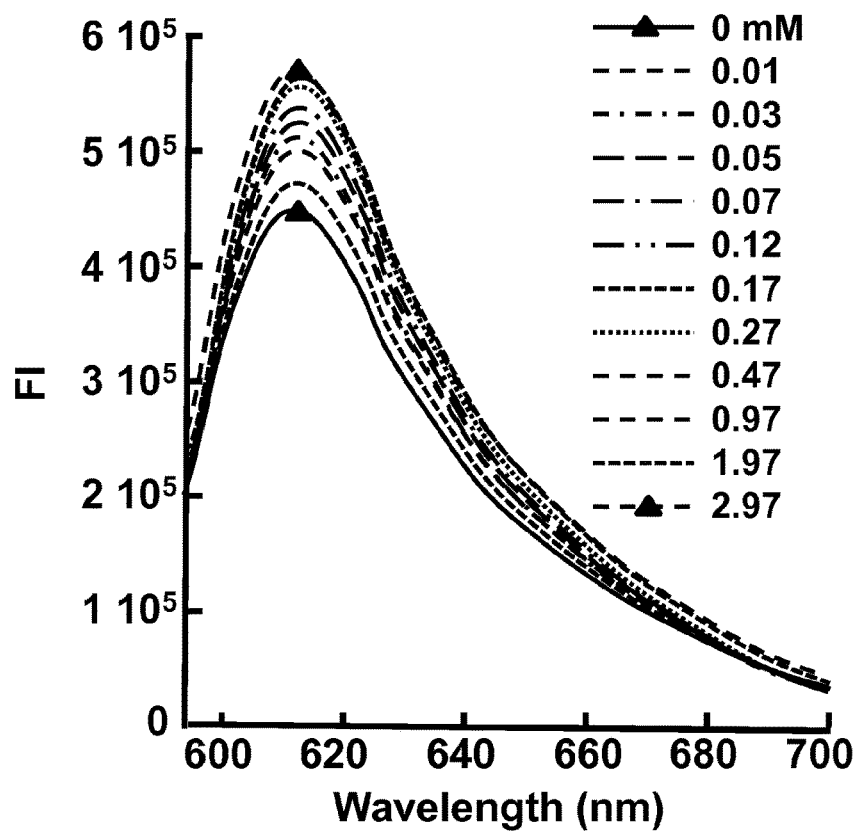
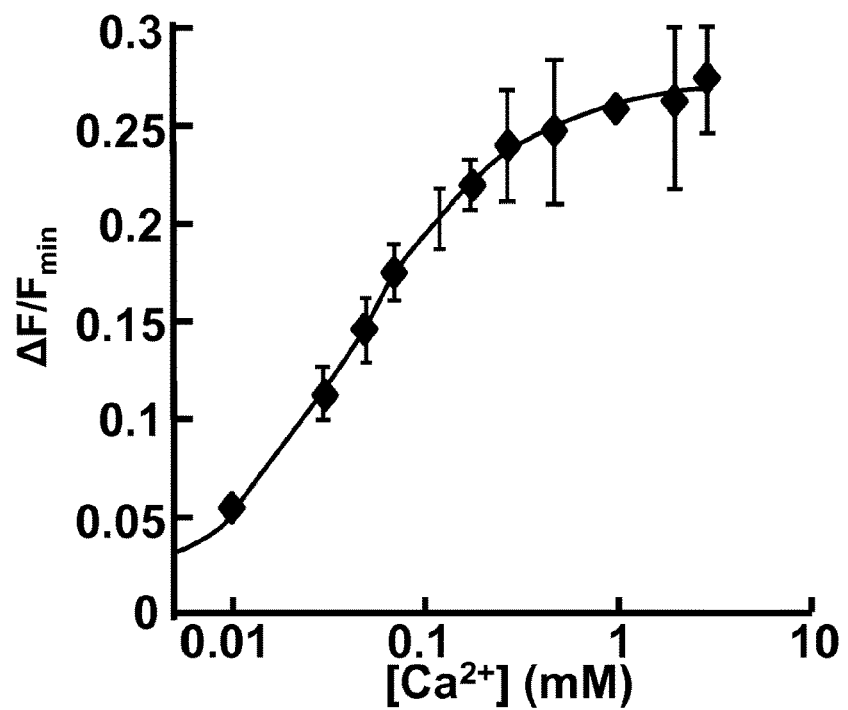
*Fig. 5A*

```
                                         1        10        20        30
                      10        20       30        40        50        60
                       |         |       ||         |         |         |
mCherry                                  MVSKGEEDNMAIIKEFMRFKVHMEGSVNGHEFEIEGE
MCD1er       MLLSVPLLLGLLGLAAADGDPAT-----------------------------------------
MCD15er      ------------------------------------------------------------
MCD1                                  ------------------------------------
MCD14                                 ------------------------------------
MCD15                                 ------------------------------------
MCD14Y                                ------------------------------------
MCD14YS                               ------------------------------------
MCD16                                 ------------------------------------
MCD17                                 ------------------------------------
MCD18                                 ------------------------------------
MCD19                                 ------------------------------------
MCD110                                ------------------------------------
MCD111                                ------------------------------------
MCD112                                ------------------------------------
MCD22                                 ------------------------------------
MCD23                                 ------------------------------------
MCD24                                 ------------------------------------
MCD25                                 ------------------------------------
MCD26                                 ------------------------------------
MCP4                                  ------------------------------------

40        50        60        70        80        90
                      70        80        90       100       110       120
                       |         |         |         |         |         |
mCherry      GEGEGRPYEGTQTAKLKVTKGGPLPFAWDILSPQFMYGSKAYVKHPADIPDYLKLSFPEG
MCD1er       ------------------------------------------------------------
MCD15er      ------------------------------------------------------------
MCD1         ------------------------------------------------------------
MCD14        ------------------------------------------------------------
MCD15        ------------------------------------------------------------
MCD14Y       ------------------------------------------------------------
MCD14YS      ------------------------------------------------------------
MCD16        ------------------------------------------------------------
MCD17        ------------------------------------------------------------
MCD18        ------------------------------------------------------------
MCD19        ------------------------------------------------------------
MCD110       ------------------------------------------------------------
MCD111       ------------------------------------------------------------
MCD112       ------------------------------------------------------------
MCD22        ------------------------------------------------------------
MCD23        ------------------------------------------------------------
MCD24        ------------------------------------------------------------
MCD25        ------------------------------------------------------------
MCD26        ------------------------------------------------------------
MCP4         ------------------------------------------------------------
```

*Fig. 15*

```
             100       110       120       130       140       150
             130       140       150       160       170       180
              |         |         |         |         |         |
mCherry  FKWERVMNFEDGGVVTVTQDSSLQDGEFIYKVKLRGTNFPSDGPVMQKKTMGWEASSERM
MCD1er   ------------------------------------------------------E-----
MCD15er  ------------------------------------------------------E-----
MCD1     ------------------------------------------------------E-----
MCD14    ------------------------------------------------------E-----
MCD15    ------------------------------------------------------E-----
MCD14Y   ------------------------------------------------------E-----
MCD14YS  ------------------------------------------------------E-----
MCD16    ------------------------------------------------------E-D---
MCD17    ------------------------------------------------------E-----
MCD18    ------------------------------------------------------E-----
MCD19    ------------------------------------------------------E-----
MCD110   ------------------------------------------------------E-----
MCD111   ------------------------------------------------------E-----
MCD112   ------------------------------------------------------E-----
MCD22    ------------------------------------------------------------
MCD23    ------------------------------------------------------------
MCD24    ------------------------------------------------------------
MCD25    ------------------------------------------------------------
MCD26    ------------------------------------------------------------
MCP4     ----------------------------------------------------E--------

160       170       180       190       200       210
             190       200       210       220       230       240
              |         |         |         |         |         |
mCherry  YPEDGALKGEIKQRLKLKDGGHYDAEVKTTYKAKKPVQLPGAYNVNIKLDITSHNEDYTI
MCD1er   ------------------------------------------D-D--------------
MCD15er  ------------------------------------------D-E--------------
MCD1     ------------------------------------------D-D--------------
MCD14    ------------------------------------------D-D--------------
MCD15    ------------------------------------------D-E--------------
MCD14Y   ------------------------------------------DYD--------------
MCD14YS  ------------------------------------------DYDS-------------
MCD16    ------------------------------------------D-D--------------
MCD17    ------------------------------------------DTESA------------
MCD18    ------------------------------------------D-E-A------------
MCD19    ------------------------------------------D-E--------------
MCD110   --------------------------------------------S--------------
MCD111   ------------------------------------------E----------------
MCD112   ------------------------------------------D-D--------------
MCD22    ------------------------------------------------------------
MCD23    ------------------------------------------E-E--------------
MCD24    ------------------------------------------E-Q--------------
MCD25    ------------------------------------------E-N--------------
MCD26    ------------------------------------------------------------
MCP4     ------------E-E---------------------------------------------
```

*Fig. 15 Cont'd*

```
                               220       230
                                250       260
                                 |         |
mCherry   VEQYERAEGRHSTGGMDELYK
MCD1er    -----E--------------KDEL
MCD15er   -----E---E----------KDEL
MCD1      -----E--------------
MCD14     -----E---E----------
MCD15     -----E---E----------
MCD14Y    -----E---E----------
MCD14YS   -----E---E----------
MCD16     -----E---E----------
MCD17     -----E---E----------
MCD18     -----E---E----------
MCD19     -----E--------------
MCD110    -----E---E----------
MCD111    -----E---E----------
MCD112    ---------Q----------
MCD22     ---E-E--------------
MCD23     ---E-E--------------
MCD24     ---E-E--------------
MCD25     ---E-E--------------
MCD26     ---E-D--------------
MCP4      --------------------
```

| | |
|---|---|
| mCherry | SEQ ID NO: 40 |
| MCD1er | SEQ ID NO: 41 |
| MCD15er | SEQ ID NO: 42 |
| MCD1 | SEQ ID NO: 43 |
| MCD14 | SEQ ID NO: 44 |
| MCD15 | SEQ ID NO: 45 |
| MCD14Y | SEQ ID NO: 49 |
| MCD14YS | SEQ ID NO: 50 |
| MCD16 | SEQ ID NO: 51 |
| MCD17 | SEQ ID NO: 52 |
| MCD18 | SEQ ID NO: 53 |
| MCD19 | SEQ ID NO: 54 |
| MCD110 | SEQ ID NO: 55 |
| MCD111 | SEQ ID NO: 56 |
| MCD112 | SEQ ID NO: 57 |
| MCD22 | SEQ ID NO: 58 |
| MCD23 | SEQ ID NO: 59 |
| MCD24 | SEQ ID NO: 60 |
| MCD25 | SEQ ID NO: 61 |
| MCD26 | SEQ ID NO: 62 |
| MCP4 | SEQ ID NO: 63 |

*Fig. 15 Cont'd*

```
                                1         10        20        30        40        50        60
CatchER              MLLSVPLLLGLLGLAAAD              VSKGEELFTGVVPILVELDGDLNGHKFSVSGEGEG
CatchER-ER TAG       MLLSVPLLLGLLGLAAADGSGPSRM---------------------------------------
CatchER-T            MLLSVPLLLGLLGLAAADGSGPSRM---------------------------------------
CatchER-T 149EY39N      VPLLLGLLGLAAADGSGPSRM-----------V-------------------------------
CatchER-T Y39N          VPLLLGLLGLAAADGSGPSRM-----------V-------------------------------
CatchER-T S30R       MLLSVPLLLGLLGLAAADGSGPSRM-------V---------------------------R---
CatchER-T S30RY39N   MLLSVPLLLGLLGLAAADGSGPSRM-------V---------------------------R---
CatchER-JP45                              M---------V-------------------------------
                                          1         10        20        30

70        80        90        100       110       120
CatchER              DATYGKLITLKFICTTGKLPVPWPTLVTTLTYGVQCFSRYPDHMKQHDFFKSAMPEGYVQE
CatchER-ER TAG       ------------------------------------------------------------
CatchER-T            ------------------------------------------------------------
CatchER-T 149EY39N   ---N--------------------------------------------------------
CatchER-T Y39N       ---N--------------------------------------------------------
CatchER-T S30R       ------------------------------------------------------------
CatchER-T S30RY39N   ---N--------------------------------------------------------
CatchER-JP45         ------------------------------------------------------------
                               40        50        60        70        80        90

130       140       150       160       170       180
CatchER              RTIFFKDDGNYKTRAEVKFEGDTLVNRIELKGIDFKEDGNILGHKLEYNYNEHNVYITAD
CatchER-ER TAG       ------------------------------------------------------------
CatchER-T            ------------------------------------------------------------
CatchER-T 149EY39N   ----------------------------------------E-------------------
CatchER-T Y39N       ------------------------------------------------------------
CatchER-T S30R       ------------------------------------------------------------
CatchER-T S30RY39N   ------------------------------------------------------------
CatchER-JP45         ------------------------------------------------------------
                              100       110       120       130       140       150
```

METAL ION SENSORS AND METHODS OF DETECTING METAL IONS

CROSS-REFERENCE TO RELATED APPLICATIONS

This application is the 35 U.S.C. § 371 national stage application of PCT Application No. PCT/US2014/049927, filed Aug. 6, 2014, which claims priority to U.S. Provisional Patent Application Ser. No. 61/862,663, entitled "ANALYTE SENSORS, METHODS FOR PREPARING AND USING SUCH SENSORS, AND METHODS OF DETECTING ANALYTE ACTIVITY" filed on Aug. 6, 2013, and U.S. Provisional Patent Application Ser. No. 61/923,252 entitled "ANALYTE SENSORS, METHODS FOR PREPARING AND USING SUCH SENSORS, AND METHODS OF DETECTING ANALYTE ACTIVITY" filed on Jan. 3, 2014, the entireties of which are hereby incorporated by reference.

FIELD OF THE DISCLOSURE

The present disclosure relates to engineered protein metal ion sensors comprising a metal ion binding site engineered into a fluorescent polypeptide for the detection of metal ion analytes and to methods of their use in vivo and in vitro.

SEQUENCE LISTING

The present disclosure includes a sequence listing incorporated herein by reference in its entirety.

BACKGROUND

Calcium transient is originated from calcium concentration gradients across biological membranes and determined by the calcium-binding affinity and kinetics of calcium channels/pumps as well as intracellular calcium-binding proteins. The spatial-temporal calcium concentration change results in different physiological signal transduction, including muscle contraction, heart beating, neurotransmitter release, and gene expression, etc. (Clapham D E (2007) *Cell* 131: 1047-1058; Berridge et al., (1998) *Nature* 395: 645-648; Berridge M J (1998) *Neuron* 21: 13-26; Bers & Guo (2005) *Ann. N. Y. Acad. Sci.* 1047: 86-98; Spitzer N C (2008) *Nat. Neurosci.* 11: 243-244).

The time scale of calcium signaling is varied, ranged from mille-seconds to minutes. Fast calcium signaling, especially associated with action potential, usually occurs with a rapid local calcium rise (milliseconds) due to calcium influx via the membrane voltage-gated calcium channel and calcium release from internal stores, for example, excitation-contraction coupling (EC coupling) in muscle cells and neurontransmitter release in neuron cells (Berridge M J (1998) *Neuron* 21: 13-26; Rios & Pizarro (1991) *Physiol. Rev.* 71: 849-908; Schneider M F (1994) *Ann. Rev. Physiol.* 56: 463-484; Baylor & Hollingworth (2003) *J. Physiol.* 551: 125-138; Bean B P (2007) *Nat. Revs. Neurosci.* 8: 451-465; Locknar et al., (2004) *J. Physiol.* 555: 627-635; Sandler & Barbara (1999) *J. Neurosci.* 19: 4325-4336; Borst & Sakmann (1999) Philosoph. *Trans R. Soc. London. Series B, Biol. Sci.* 354: 347-355; Lopez-Lopez et al., (1995) *Science* 268: 1042-1045; Cannell et al., (1995) *Science* 268: 1045-1049; Polakova et al., (2008) *J. Physiol.* 586: 3839-3854; Fill & Copello (2002) *Physiol. Rev.* 82: 893-922). Slower calcium signaling usually happens in cellular events such as an immune response, which can last minutes and to hours. In slow calcium signaling pathways, the calcium transient is controlled by several factors and secondary messengers like DAG, $IP_3$ and ATP, involving more complicated regulation mechanisms.

To accurately monitor calcium transients in terms of kinetics, amplitude and duration, calcium indicators are required to have several key properties. It is necessary to match the dissociation equilibrium constant $K_d$ of calcium indicators to the resting calcium concentration of the sub-cellular compartment in the magnitude of $10^2$ $s^{-1}$. To detect fast calcium-release from calcium pools in muscle and neuronal cells, calcium-binding affinity in the range of 0.1-1 mM and a calcium disassociation-rate of the indicator greater than 500 $s^{-1}$ is necessary.

The development of genetically-encoded indicators (GE-CIs) allows probing spatial-temporal cellular events and cell signaling in real time. GECIs are a big family including, but not limited to, GCaMP, GECO, TN and the Cameleon series. They are composed of a fluorescent protein moiety and take advantage of the native cytosolic calcium-binding proteins (CBPs) Calmodulin (CaM) or Troponin C (TnC) to sensor calcium and calcium-induced global conformational rearrangements. Each CaM or TnC can bind four calcium ions in a cooperative manner with a high calcium-binding affinity ($K_d=10^{-7}$ M) at the cytosolic calcium change and their calcium-binding on-rates are in the magnitude of $10^7$ $M^{-1}$ $s^{-1}$. The high calcium-binding affinity and on-rate enable them to sense the immediate [$Ca^{2+}$] rise in the cytosol.

These GECIs, however, have slow dissociation-rates of around 0.1-10 $s^{-1}$ likely due to the cooperativity associated with multiple calcium-binding sites and multiple layers of conformational change. The slow kinetics of signal decay is disadvantageous to probe physiological fast calcium transient, especially in the neuron and skeletal muscle cells. Therefore, efforts have been made to reduce the calcium-binding affinities. One typical example was Cameleon D1ER, which has a multiple $K_d$s around 0.8 and 60 µM and an off-rate of about 256 $s^{-1}$. However, it is still not fast enough to capture calcium release from sarcoplasmic reticulum (SR) upon the stimulation in the mouse FDB fibers.

Accordingly, to fulfill the unmet need of a fast calcium indicator, a calcium indicator, designated "CatchER" was generated without incorporating a native calcium-binding domain by engineering a calcium-binding site into a single fluorescent protein EGFP. The calcium-binding stoichiometry is 1:1 and the $K_d$ is 0.18 mM in vitro and 0.8 mM calibrated in situ, allowing the measurement of basal calcium in different cell lines and their changes responding to different drugs. Compared to Cameleon D1ER, CatchER exhibited faster kinetics, allowing it to catch the calcium change in SR in the skeletal muscle cells.

SUMMARY

The present methodology provides designing calcium-binding+ biosensors by creating a calcium-binding site on a fluorescent with site-direct mutagenesis that can be used in tissue and animal imaging, to accurately measure a real-time calcium ion concentration in a cell. Provided are enhanced sensors with different signal peptides and multiple-magnitude binding affinities, which can help in detecting $Ca^{2+}$ signaling responses to different agonists in various subcellular organelles of diverse cell types.

Accordingly, one aspect of the disclosure encompasses embodiments of a polypeptide metal ion sensor comprising an engineered red fluorescent polypeptide (RFP) having a heterologous metal ion binding site comprising a plurality of negatively charged residues that in the presence of a metal ion bound thereto comprise a plurality of carboxyl oxygens orientated in a pentagonal bipyrimdal geometry, and wherein the metal ion binding site is in cooperative interaction with a chromophore region of the engineered RFP such that when the sensor does not have a metal ion bound thereto it emits a first fluorescent signal and when the sensor does have a metal ion bound thereto it emits a second fluorescent signal, wherein the first and the second fluorescent signals are distinguishably detectable, and wherein the metal ion sensor has a $k_{off}$ value for the metal ion of at least $10\ s^{-1}$.

Another aspect of the disclosure encompasses embodiments of a recombinant nucleic acid having a nucleotide sequence having at least 95% similarity to a sequence selected from the group consisting of SEQ ID NOs: 7-36 or encoding a polypeptide metal ion sensor to an amino acid sequence selected from the group consisting of SEQ ID NOs: 41-63.

Another aspect of the disclosure encompasses embodiments of a polypeptide metal ion sensor comprising an engineered green fluorescent polypeptide (GFP) having a heterologous metal ion binding site, wherein said engineered GFP is a variant having at least 90% similarity to the amino acid sequence SEQ ID NO: 37 and having at least one amino acid substitution in sequence SEQ ID NO: 37 and selected from the group consisting of L22V, S175G, and I218M and, when having a metal ion species bound thereto, has an elevated fluorescence output compared to the polypeptide SEQ ID NO: 37 binding to the same metal ion species at 37° C.

Still another aspect of the disclosure encompasses embodiments of a recombinant nucleic acid can have a nucleotide sequence having at least 95% similarity to a sequence selected from SEQ ID NOs: 65-75 and 79-82.

Still another aspect of the disclosure encompasses embodiments of a method of detecting metal ion in a biological sample, comprising: (i) providing a polypeptide metal ion sensor selected from: (a) an engineered red fluorescent polypeptide (RFP) having a heterologous metal ion binding site comprising a plurality of negatively charged residues that in the presence of a metal ion bound thereto comprise a plurality of carboxyl oxygens orientated in a pentagonal bipyrimdal geometry, and wherein the metal ion binding site is in cooperative interaction with a chromophore region of the engineered RFP such that when the sensor does not have a metal ion bound thereto it emits a first fluorescent signal and when the sensor does have a metal ion bound thereto it emits a second fluorescent signal, wherein the first and the second fluorescent signals are distinguishably detectable, and wherein the metal ion sensor has a $k_{off}$ value for the metal ion of at least $10\ s^{-1}$ and (b) an engineered green fluorescent polypeptide (GFP) having a heterologous metal ion binding site, wherein said engineered GFP is a variant having at least 90% similarity to the amino acid sequence SEQ ID NO: 37 and having at least one amino acid substitution in sequence SEQ ID NO: 37 and selected from the group consisting of L22V, S175G, and I218M and, when having a metal ion species bound thereto, has an elevated fluorescence output compared to the polypeptide SEQ ID NO: 37 binding to the same metal ion species at 37° C.; (ii) delivering the polypeptide metal ion sensor or an expression vector having an nucleic acid sequence encoding said metal sensor to a biological sample; (iii) detecting a first fluorescent signal emitted by said sensor; (iii) generating a physiological or cellular change in the biological sample; (iv) detecting a second fluorescent signal emitted by said sensor after step (iii); and (v) comparing the first and second fluorescent signals, wherein a ratiometric change in at least one of a wavelength, an intensity, and a lifetime between the first and second fluorescent signals indicates a change in the rate of release or intracellular concentration of a metal ion in the sample.

Still another aspect of the disclosure encompasses embodiments of a genetically modified cell comprising a recombinant nucleic acid according to the disclosure.

BRIEF DESCRIPTION OF THE FIGURES

Further aspects of the present disclosure will be more readily appreciated upon review of the detailed description of its various embodiments, described below, when taken in conjunction with the accompanying drawings.

FIG. 2B illustrates the pH profile of wild type mCherry (SEQ ID NO: 40) and RapidER (MCD1) (SEQ ID NO: 43) in the absence and presence of calcium.

FIG. 3C illustrates the use of $Tb^{3+}$ as a probe to determine the calcium-binding to MCD15 (SEQ ID NO: 45). The dissociation constant was 0.27±mM. The inset shows fluorescence spectra at different concentrations of $Tb^{3+}$ recorded from 500 to 570 nm by fluorescence spectrophotometer with excitation at 282 nm.

FIG. 3D illustrates a structure model of RapidER (MCD1) (SEQ ID NO: 43).

FIG. 3E illustrates a structure model of $Ca^{2+}$-RapidER.

FIG. 3F illustrates a structure model of $Ca^{2+}$-CatchER.

FIG. 5A illustrates calcium titration traces. Calcium was added to 10 µM RapidER (MCD1) (SEQ ID NO: 43) at room temperature.

FIG. 6A illustrates the calculated $K_d$.

FIG. 6B illustrates the average of calculated calcium concentration. For comparison, the calcium concentration was back-calculated assuming the protein concentration was the same. Using extinction coefficients $E_{280}$=38.9 $mM^{-1}$ $cm^{-1}$. The concentrations of total protein wild-type mCherry (SEQ ID NO: 40), MCD1 (SEQ ID NO: 43), MCD14 (SEQ ID NO: 44), MCD15 (SEQ ID NO: 45) and mcP6 at equilibrium were 15 µM, 11 µM, 45 µM, 38 µM and 30 µM, respectively. The black bar indicates the protein sample in the dialysis bag, and the white bar indicates the buffer samples that were collected outside the dialysis bags.

FIG. 7A illustrates the $Tb^{3+}$ lifetime of the free form and in the FRET pair. The average lifetime was obtained by the double exponential fitting according to the Equation 51.

FIG. 7B illustrates the distance of the $Ca^{2+}$-chromophore measured in the modeled structure of $Ca^{2+}$-RapidER (MCD1) (SEQ ID NO: 43), ranged in 10.4-15.9 Å.

FIG. 8A illustrates the MCD15er (SEQ ID NO: 42) fluorescence change in response to drugs in the transiently transfected BHK cell line.

FIG. 8B illustrates the MCD15er (SEQ ID NO: 42) fluorescence change in response to drugs in the transiently transfected HeLa cell line.

FIG. 8C illustrates the MCD15er (SEQ ID NO: 42) fluorescence change in response to drugs in the transiently transfected C2C12 cell line.

FIG. 8D is a digital image illustrating MCD15 (SEQ ID NO: 45) sensing $Ca^{2+}$ release from endoplasmic reticulum in C2C12 cells.

FIG. 15 illustrates the amino acid sequence alignments for the RFP (mCherry-based) metal ion sensors of the disclosure. The chromophore is indicated in bold. Dashes indicate identical amino acids and blanks indicate deleted or absent residues. The drawings are described in greater detail in the description and examples below.

The $\Delta F/F_0$ time course was averaged from N cells/ROIs, and the experimental event markers were labeled. The fluorescence and bright filed images at the beginning and the end of the time course were shown in the bottom panel.

Figure 20A:
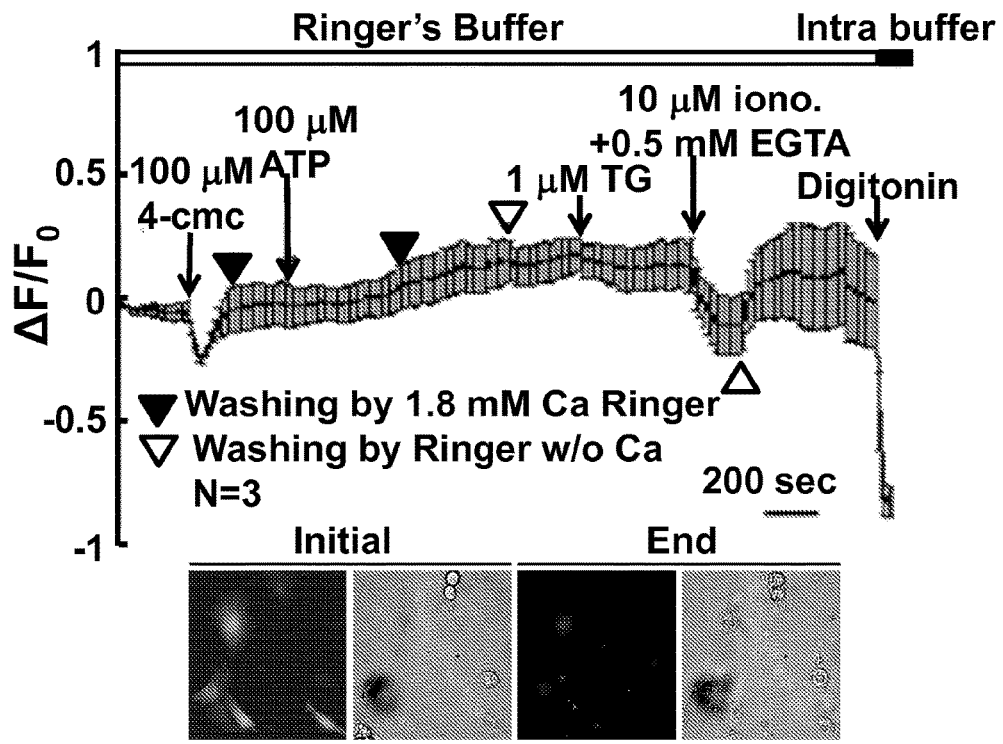
FIG. 20A illustrates CatFKBP responding to drugs in non-differentiated C2C12 cells.
Figure 20B:
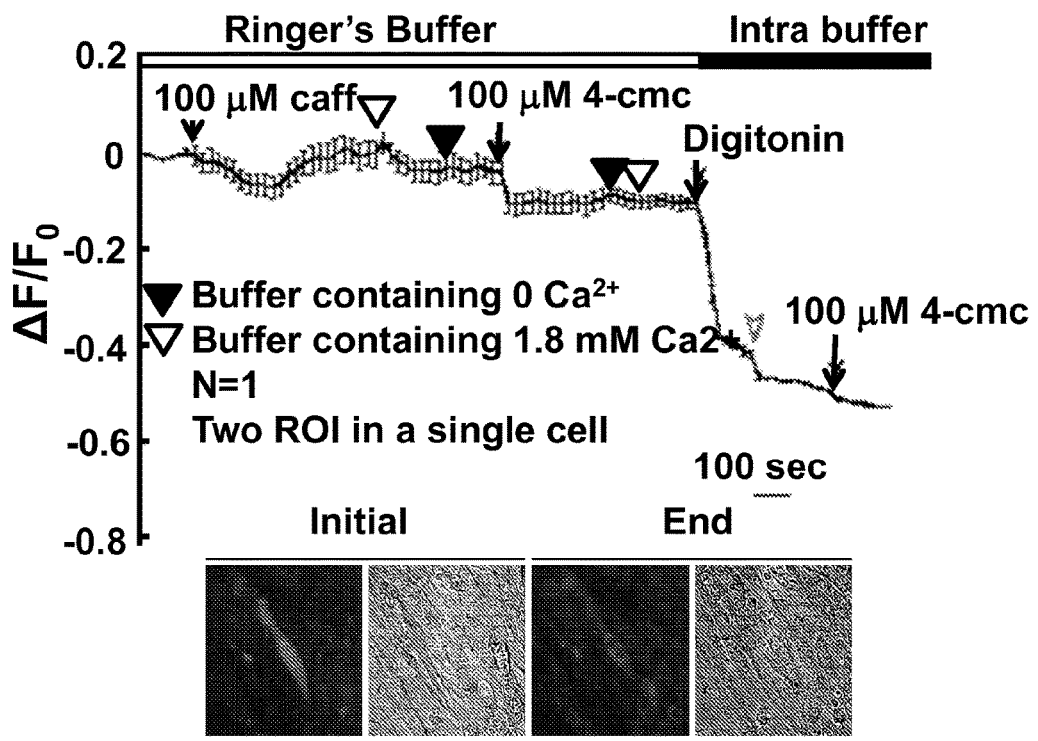

FIG. 20B illustrates CatFKBP responding to drugs in induced differentiated C2C12 cells.

The $\Delta F/F_0$ time course was averaged from N cells/ROIs, and the experimental event markers were labeled. The fluorescence and bright filed images at the beginning and the end of the time course were shown in the bottom panel.

Figure 21A:
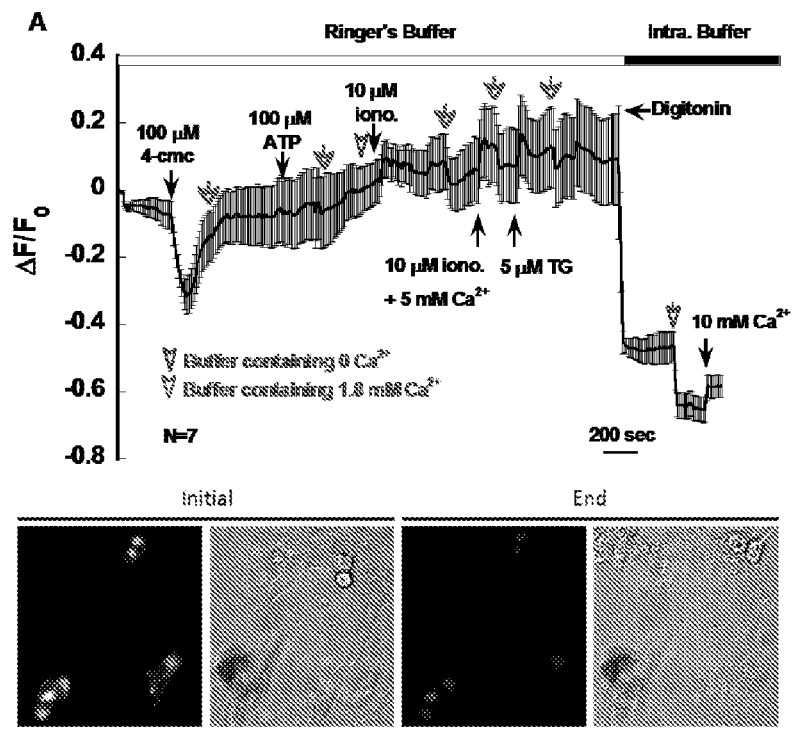

FIG. 21A illustrates calcium imaging of CatZ5 transfected to C2C12 myoblasts. Caffeine, 4-cmc and digitonin were applied and the time points of reagents addition were labeled.

Figure 21B:
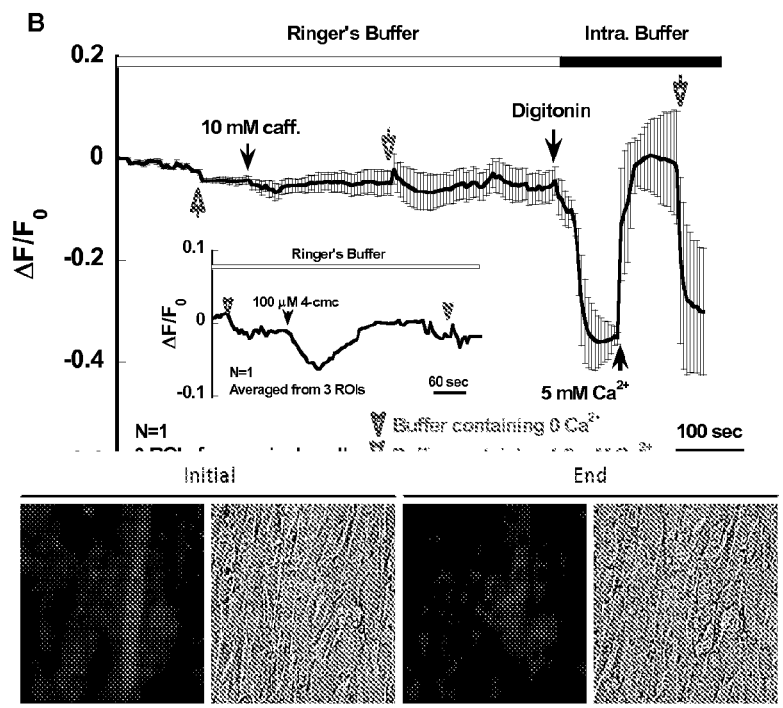

FIG. 21B illustrates calcium imaging of CatZ5 transfected to differentiated C2C12 cells. The inset shows the 4-cmc induced fluorescence change in one cell other than the one treated with caffeine. The fluorescence and bright field images were taken in the beginning and the end of the imaging record.

Figure 22A:
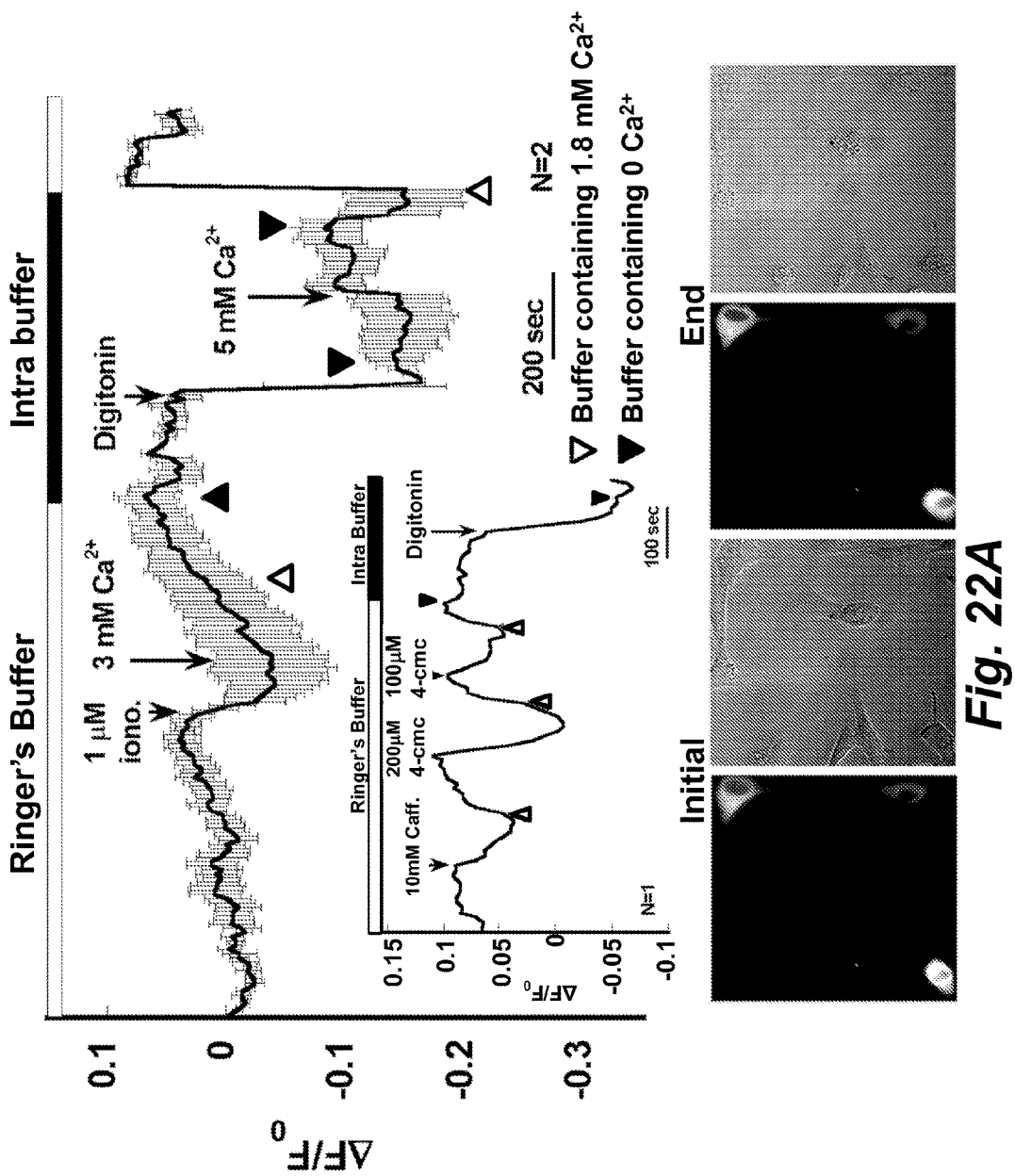

FIG. 22A illustrates calcium imaging of Z10Cat transfected to C2C12 myoblasts. Caffeine, 4-cmc, ionomycin and digitonin were applied and the time points were labeled. The fluorescence and bright field images were taken in the beginning and the end of the experiment. The inset shows the time course of fluorescence in panel A was data collected from the other cell.

Figure 22B:
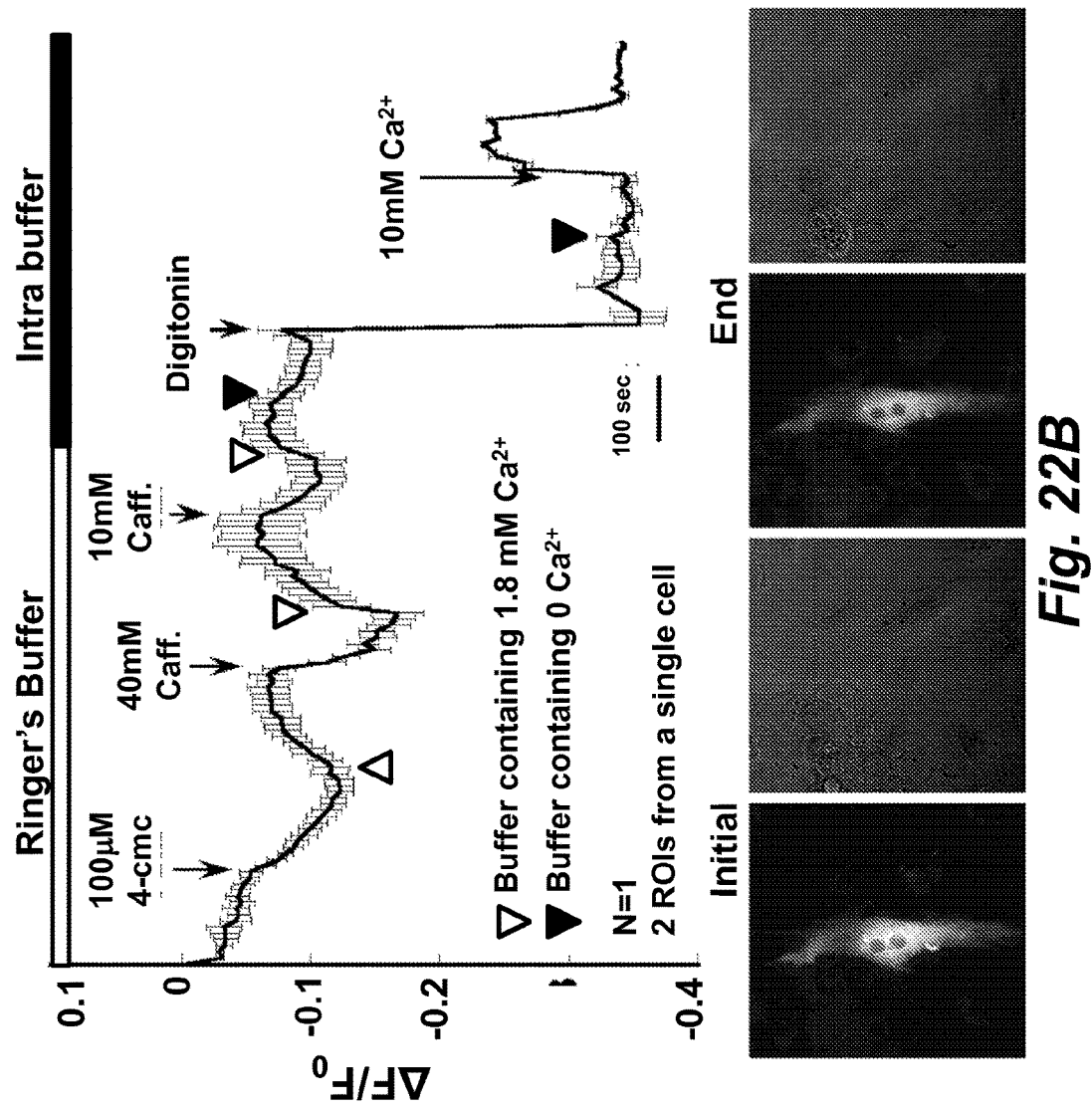
Figure 23:
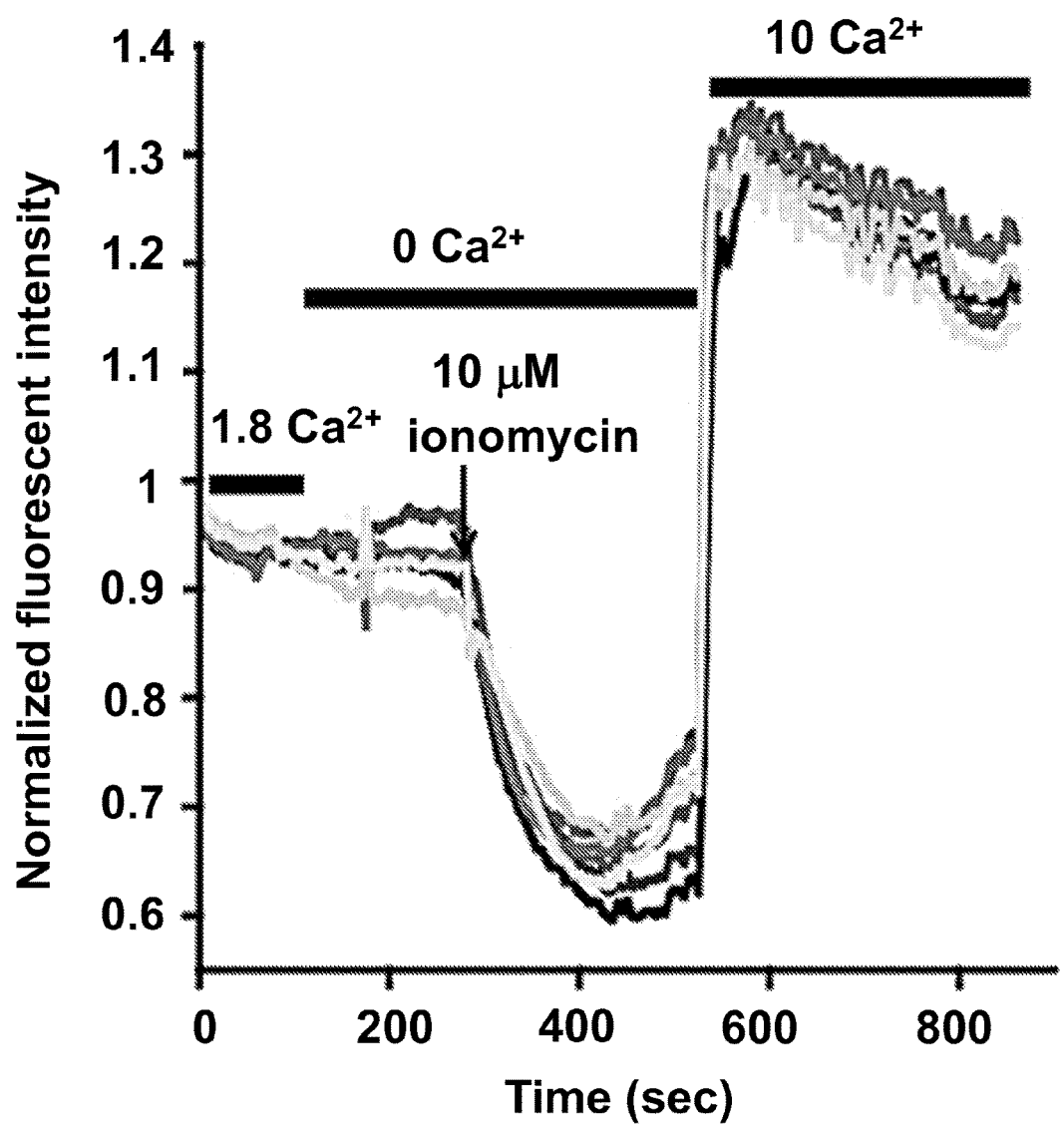

FIG. 22B illustrates calcium imaging of Z10Cat transfected to differentiated C2C12 cells. Caffeine, 4-cmc, ionomycin and digitonin were applied and the time points were labeled. The fluorescence and bright field images were taken in the beginning and the end of the experiment. The inset shows the time course of fluorescence in panel A was data collected from the other cell FIG. 23 is a graph illustrating the effects of adding ionomycin and calcium to HEK293 cells expressing the metal ion sensor CatchER-T at 37° C.

Figure 24:
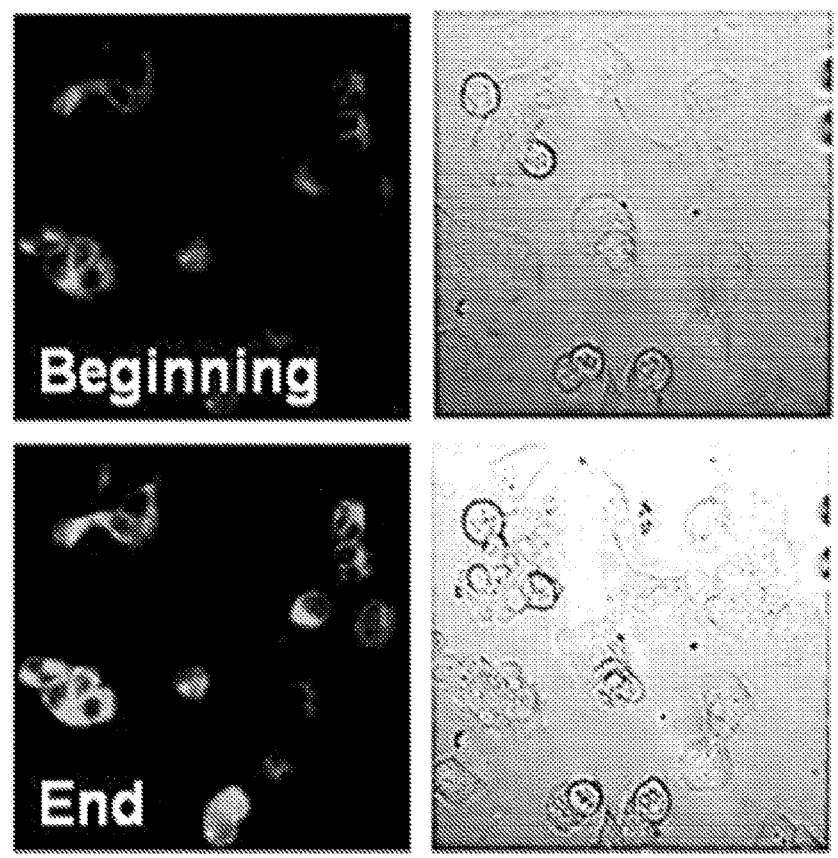

FIG. 24 illustrates the effects of adding ionomycin and calcium to HEK293 cells expressing the metal ion sensor CatchER-T at 37° C. as imaged using the fluorescent signal from the intracellular sensor polypeptide.

Figure 25:
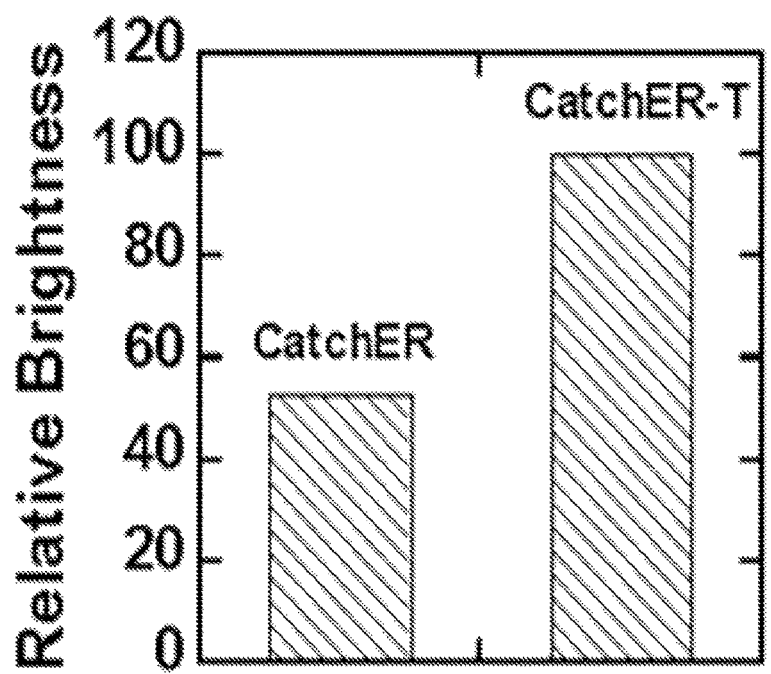

FIG. 25 is a graph illustrating the increase in brightness (intensity) of the fluorescent signal from the sensor variant CatchER-T (SEQ ID NO: 65).

Figure 26:
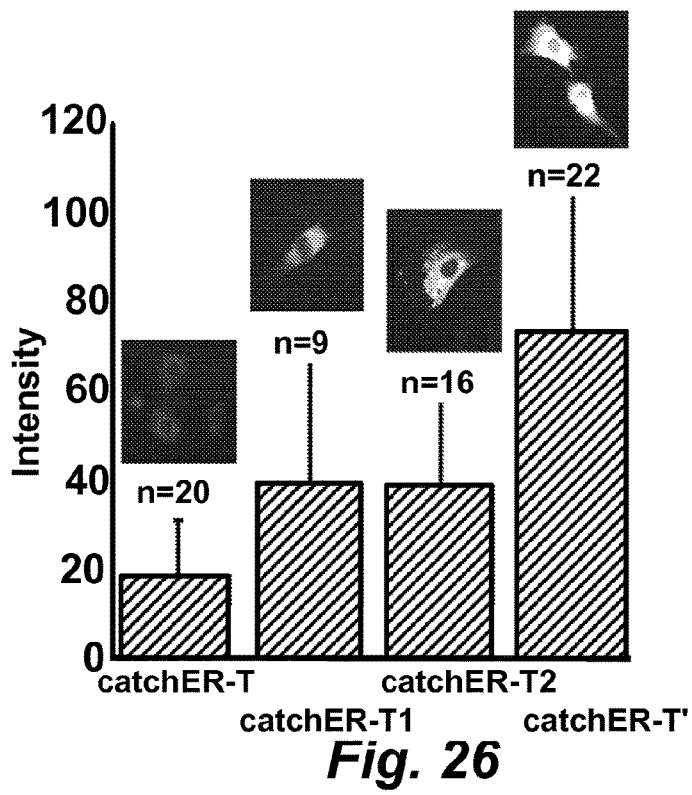

FIG. 26 is a trace illustrating the monitoring of endoplasmic reticulum calcium release during cytosolic calcium oscillation as determined using the sensor CatchER-t (SEQ ID NO: 65).

Figure 27:
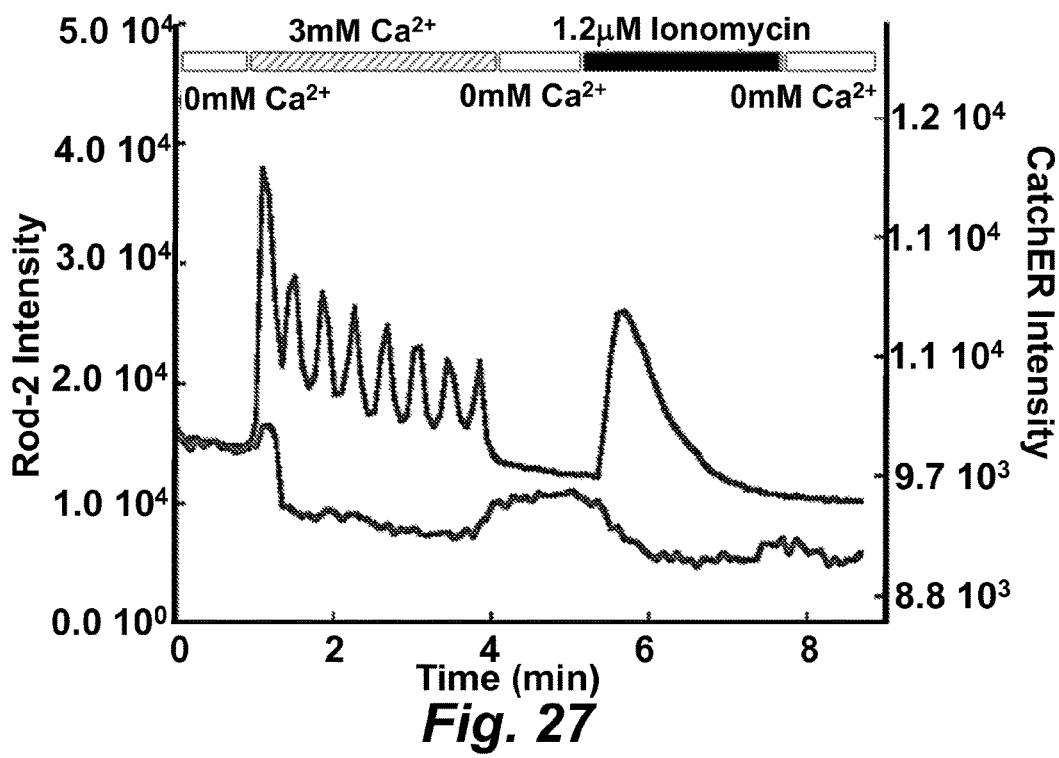

FIG. 27 illustrates a graph showing the increase in detectable intensity of fluorescence emitted by the calcium sensors CatchER-T1 (CatchER Y39N, SEQ ID NO: 72), CatchER-T2 CatchER S30R, SEQ ID NO: 73), and CatchER-T' (CatchER S30R Y39N, SEQ ID NO: 74) compared with the parent sensor CatchER-T, which is itself capable of a brighter emission than CatchER.

Figure 28:
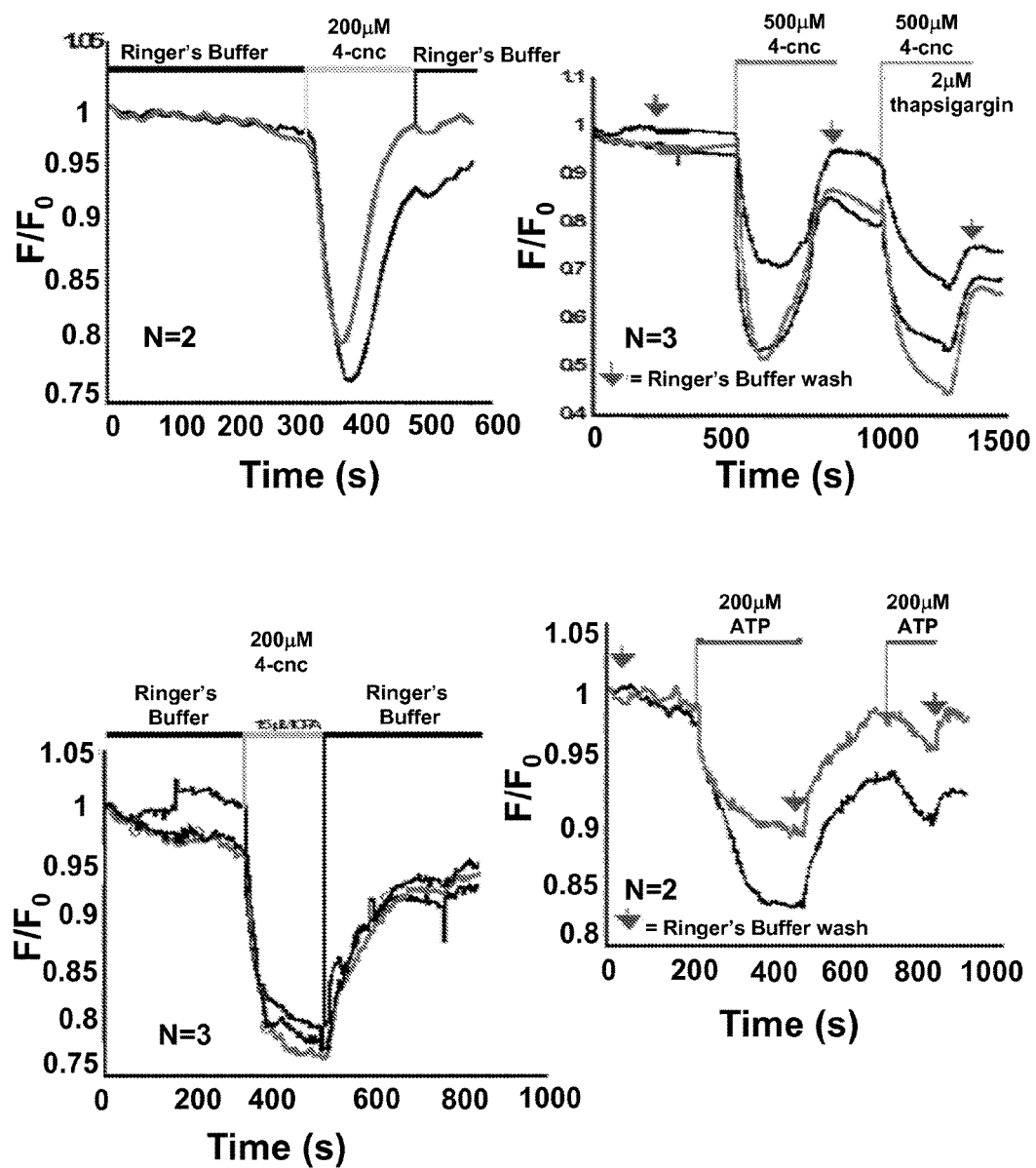

FIG. 28 illustrates a series of graphs showing the use of the sensor CatchER-T' to detect calcium concentration changes in C2C12 cells treated with different drugs.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Definitions

In describing and claiming the disclosed subject matter, the following terminology will be used in accordance with the definitions set forth below. Further definitions are provided in context below. Unless otherwise defined, all technical and scientific terms used herein have the same meaning as commonly understood by one of ordinary skill in the art of molecular biology. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001). As appropriate, procedures involving the use of commercially available kits and reagents are generally carried out in accordance with manufacturer defined protocols and/or parameters unless otherwise noted.

The term "polypeptide metal ion sensor" as used herein refers to polypeptide that includes a metal ion binding site generated by the interaction of negatively-charged amino acid side-chains and a metal ion. Advantageously, the sensor can bind to calcium and Tb3+, but the sensors of the disclosure can be capable of binding other ions, most advantageously divalent ions.

The term "engineered polypeptide" as used herein refers to a polypeptide that has been designed to have a heterologous metal ion binding site. The term "engineered" as used herein refers to the generation of mutations in the amino acid sequence of a polypeptide sensor such as a fluorescent protein to introduce negatively charged amino acids that on folding of the polypeptide form a calcium binding site or, if not participating in the site, generate advantageous properties in the sensor not found in the non-mutated parent sensor. For example, but not intended to be limiting, such advantageous properties may be a change in the detectable wavelength of the emitted fluorescence, in the intensity of the fluorescent signal, the magnitude of the signal under elevated temperatures, the kinetics of the binding and dissociation of the metal ion analyte, and the like.

The term "heterologous metal ion binding site" as used herein refers to a metal ion-specific binding site of an engineered polypeptide and which is not found in the native or wild-type fluorescent protein. While the native protein may attract metal ions under some conditions, a heterologous site with the context of the disclosure refers to the juxtaposition of substituted and non-native negatively-charged amino acid side-chains that can form a binding site not found in the wild-type.

The term "co-operative interaction" as used herein refers to changing a fluorescent signal of a fluorescent protein, the changing being generated by the binding of a metal ion such as calcium to a calcium-binding site and the result in the forming of new bonds with a chromophore site within the protein due to conformational changes of the protein.

The term "heterologous negatively-charged amino acid substitution" as used herein refers to negatively-charged amino acids not found in the same position in the native or wild-type protein.

The term "polypeptide" as used herein refers to proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three-letter or a single-letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "variant" as used herein refers to a polypeptide or polynucleotide that differs from a reference polypeptide or polynucleotide, but retains essential properties. A typical variant of a polypeptide differs in amino acid sequence from another, reference, polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions).

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

The term "identity" as used herein refers to a relationship between two or more polypeptide sequences as determined by comparing the sequences. By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given percent identity is determined by multiplying the total number of amino acids in the reference polypeptide by the numerical percent of the respective percent identity (divided by 100) and then subtracting that product from said total number of amino acids in the reference polypeptide.

The term "polynucleotide" as used herein refers to any polyribonucleotide or polydeoxribonucleotide that may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

As used herein, DNA may obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

cDNA can be cloned from mRNA encoding the protein by, for example, the following method: First, the mRNA encoding the protein is prepared from the above-mentioned tissues or cells expressing and producing the selected protein. mRNA can be prepared by isolating total RNA by a known method such as guanidine-thiocyanate method (Chirgwin et al., (1979) Biochemistry 18: 5294), hot phenol method, or AGPC method, and subjecting it to affinity chromatography using oligo-dT cellulose or poly-U Sepharose.

The cDNA is then synthesized, for example, by a well-known method using reverse transcriptase, such as the method of Okayama et al., (1982) *Mol. Cell. Biol.* 2: 161; (1983) Mol. Cell. Biol. 3: 280, or the method of Hoffman et al., (1983) *Gene* 25: 263, and converted into double-stranded cDNA. A cDNA library is prepared by transforming *E. coli* with plasmid vectors, phage vectors, or cosmid vectors having this cDNA or by transfecting *E. coli* after in vitro packaging.

The term "substantially pure" as used herein in reference to a given polypeptide or polynucleotide means that the polypeptide is substantially free from other biological macromolecules. For example, the substantially pure polypeptide or polynucleotide is at least 75%, 80, 85, 95, or 99% pure by dry weight. Purity can be measured by any appropriate standard method known in the art, for example, by column chromatography, polyacrylamide gel electrophoresis, HPLC analysis, and the like.

The term "primer" as used herein refers to an oligonucleotide complementary to a DNA segment to be amplified or replicated. Typically primers are used in PCR. A primer hybridizes with (or "anneals" to) the template DNA and is used by the polymerase enzyme as the starting point for the replication/amplification process. By "complementary" it is meant that the primer sequence can form a stable hydrogen bond complex with the template.

The term "vector" as used herein refers to a genetic unit (or replicon) to which or into which other DNA segments can be incorporated to effect replication, and optionally, expression of the attached segment. Examples include, but are not limited to, plasmids, cosmids, viruses, chromosomes and mini-chromosomes. Exemplary expression vectors include, but are not limited to, baculovirus vectors, modified vaccinia Ankara (MVA) vectors, plasmid DNA vectors, recombinant poxvirus vectors, bacterial vectors, recombinant baculovirus expression systems (BEVS), recombinant rhabdovirus vectors, recombinant alphavirus vectors, recombinant adenovirus expression systems, recombinant DNA expression vectors, and combinations thereof.

The plasmid vectors used herein are not limited as long as they are replicated and maintained in hosts. Any phage vector that can be replicated in hosts can also be used. Examples of commonly used cloning vectors are pUC19, λgt10, λgt11, and so on. A vector having a promoter that can express a gene encoding the desired protein in a host is preferably used.

cDNA can be inserted into a plasmid by, for example, the methods of Maniatis et al. (Molecular Cloning, A Laboratory Manual, second edition, Cold Spring Harbor Laboratory, p. 1.53, 1989). These methods can be simply performed by using a commercially available cloning kit. The recombinant plasmid or phage vector thus obtained is introduced into an appropriate host cell such as a prokaryote (for example, *E. coli* strains HB101, DH5a, MC1061/P3, etc.) or as disclosed herein.

Examples of a method for introducing a plasmid into a host are the calcium chloride method, the calcium chloride/rubidium chloride method, a liposome method, and an electroporation method. Phage vectors can be introduced into host cells by, for example, a method in which the phage DNAs are introduced into grown hosts after in vitro packaging. In vitro packaging can be easily performed with a commercially available in vitro packaging kit.

The term "recombinant vector" as used herein refers to any vector that can be used as long as it is capable of retaining replication or self-multiplication in each host cell of prokaryotic and/or eukaryotic cells, including plasmid vectors and phage vectors. The recombinant vector can easily be prepared by ligating the DNA encoding the protein with a vector for recombination available in the art (plasmid DNA and bacteriophage DNA) by the usual method.

Specific examples of the vectors for recombination used are *E. coli*-derived plasmids such as pBR322, pBR325, pUC12, pUC13, and pUC19, yeast-derived plasmids such as pSH19 and pSH15, and *Bacillus subtilis*-derived plasmids such as pUB110, pTP5, and pC194. Examples of phages are a bacteriophage such as lambda phage, and an animal or insect virus (pVL1393, Invitrogen) such as a retrovirus, vaccinia virus, and nuclear polyhedrosis virus.

The term "expression vector" as used herein refers to a vector useful for expressing the DNA encoding the protein used herein and for producing the protein. The expression vector is not limited as long as it expresses the gene encoding the protein in various prokaryotic and/or eukaryotic host cells and produces this protein. Examples thereof are, but not limited to, pMAL C2, pEF-BOS ((1990) *Nucleic Acids Res.* 18:5322, and so on), pME18S pCDNA (Experimental Medicine: SUPPLEMENT, "Handbook of Genetic Engineering" (1992)), etc.

When bacteria, particularly *E. coli*, are used as host cells an expression vector generally comprises, at least, a promoter/operator region, an initiation codon, the DNA encoding the protein termination codon, terminator region, and replicon.

When yeast, animal cells, or insect cells are used as hosts, an expression vector is preferably comprised of, at least, a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used. DNA plasmids can also be directly introduced to the mammalian cells of animals to express proteins.

A promoter/operator region to express the protein in bacteria comprises a promoter, an operator, and a Shine-Dalgarno (SD) sequence (for example, AAGG). For example, when the host is *E. coli*, it preferably comprises a Trp promoter, a lac promoter, a recA promoter, a λPL promoter, a tac promoter, or the like. Examples of a promoter to express the protein in yeast are a PH05 promoter, a PGK promoter, a GAP promoter, an ADH promoter, and so on. When the host is *Bacillus*, examples thereof can be an SL01 promoter, an SP02 promoter, a penP promoter, and so on. When the host is a eukaryotic cell such as a mammalian cell, examples thereof are a SV40-derived promoter, a retrovirus promoter, a heat shock promoter, and so on, and preferably an SV-40 and retrovirus-derived one. As a matter of course, the promoter is not limited to the above examples. In addition, using an enhancer is effective for expression.

The term "codon" means a specific triplet of mononucleotides in the DNA chain or mRNA that make up an amino acid or termination signal. A preferable initiation codon is, for example, a methionine codon (ATG). A commonly used termination codon, for example, TAG, TAA, TGA, is exemplified as a termination codon. Usually, used natural or synthetic terminators are used as a terminator region.

A selectable marker usually employed can be used according to the usual method. Examples thereof are resistance genes for antibiotics, such as tetracycline, ampicillin, or kanamycin.

Affinity tags such His-tag and GST can be added at the sequence end to facilitate protein purification and recognition by Western blot and pulldown assay. Examples of other tags such as HA and FLAG can also be added to allow further manipulation of the constructs.

As used herein, "transformants" can be prepared by introducing the expression vector mentioned above into host cells.

As used herein, "host" cells are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces, Pichia*, and such), animal cells, or insect cells).

*E. coli* or animal cells are preferably used. Specific examples are *E. coli* strains DH5α, TB1, HB101, and the like, mouse-derived cells (COP, L, C127, Sp2/0, NS-1, NIH 3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such). The proteins disclosed herein, can be produced by cultivating transformants (in the following, this term includes transfectants) comprising an expression vector prepared as mentioned above in nutrient media.

The nutrient media preferably comprise a carbon source, an inorganic or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meat extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

The terms "chimeric", "fusion" and "composite" are used to denote a protein, peptide domain or nucleotide sequence or molecule containing at least two component portions that are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences that encode them, are recombinant in the sense that they contain at least two constituent portions that are not otherwise found directly linked (covalently) together in nature.

An "insertion" or "addition", as used herein, refers to a change in an amino acid or nucleotide sequence resulting in the addition or insertion of one or more amino acid or nucleotide residues, respectively, as compared to the corresponding naturally occurring molecule.

A "deletion" or "subtraction", as used herein, refers to a change in an amino acid or nucleotide sequence resulting in the deletion or subtraction of one or more amino acid or nucleotide residues, respectively, as compared to the corresponding naturally occurring molecule.

A "substitution", as used herein, refers to the replacement of one or more amino acids or nucleotides by different amino acids or nucleotides, respectively.

A "mutation" is an inheritable change in a DNA sequence relative to a reference "wild-type" DNA sequence. Mutations can occur as a result of a single base change, multiple base changes, or the addition or deletion of more than one nucleotide to a DNA sequence.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

A "wild-type" strain is capable of a full range of metabolic activities. For example, wild-type strains of *Salmonella* can synthesize all 20 amino acids from a single carbon source. A "wild-type" protein or polypeptide as used herein refers to an amino acid sequence unmodified from a sequence found in nature.

A "point mutation" is a change in one, or a small number of base pairs, in a DNA sequence. Point mutations may result from base pair substitutions or from small insertions or deletions.

A "transition" is a point mutation in which a purine is replaced with a purine or a pyrimidine is replaced with a pyrimidine.

A "transversion" is a point mutation in which a purine is replaced with a pyrimidine or a pyrimidine with a purine. Generally speaking, transitions are more common than transversions because the former are not detected by the proofreading enzymes.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used.

"Fluorescent protein" refers to any protein capable of emitting light when excited with appropriate electromagnetic radiation. Fluorescent proteins include proteins having amino acid sequences that are either natural or engineered, such as the green fluorescent proteins derived from *Aequorea*-related fluorescent proteins or red fluorescent proteins derived from *Discosoma* sp.

"Physical linkage" refers to any method known in the art for functionally connecting two molecules (which are termed "physically linked"), including without limitation, recombinant fusion with or without intervening domains, non-covalent association, covalent bonding (e.g., disulfide bonding and other covalent bonding), hydrogen bonding; electrostatic bonding; and conformational bonding, e.g., antibody-antigen, and biotin-avidin associations. "Fused" refers to linkage by covalent bonding.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

The term "analytes" as used herein refers to atoms, molecules or ions that can bind to proteins or peptides. An analyte may bind reversibly or irreversibly and such a bond may be covalent or non-covalent. While $Ca^{2+}$, $Tb^{3+}$, $Ln^{3+}$ and $Pb^{2+}$ are used in preferred embodiments of this disclosure as an exemplary analyte, it is understood that analytes suitable with this disclosure include, but are not limited to, metal ions including Group IIA metal ions, transition metal ions, and Lanthanide Series ions.

"Binding motif" is part of a binding site, often in a larger protein. The term binding site may be used interchangeably with the term binding motif and vice versa.

"Chemical reactions" can include the formation or dissociation of ionic, covalent, or non-covalent structures through known means. Chemical reactions can include changes in environmental conditions such as pH, ionic strength, and temperature.

"Conformation" is the three-dimensional arrangement of the primary, secondary, and tertiary structures of a molecule, and in some instances the quaternary structure of a molecule, including side groups in the molecule; a change in conformation occurs when the three-dimensional structure of a molecule changes. A conformational change may be a shift from an alpha-helix to a beta-sheet or a shift from a beta-sheet to an alpha-helix.

"Detectable changes" or "responsiveness" means any response of a protein to its microenvironment. Such detectable changes or responsiveness may be a small change or shift in the orientation of an amino acid or peptide fragment of the sensor polypeptide as well as, for example, a change in the primary, secondary, or tertiary structure of a polypeptide, and in some instances the quaternary structure of a polypeptide, including changes in protonation, electrical and chemical potential and or conformation. A "measurable difference" in any fluorescent properties between the active and inactive states suffices for the utility of the fluorescent protein substrates of the disclosure in assays for activity. A measurable difference can be determined by measuring the amount of any quantitative fluorescent property, e.g., the fluorescence signal at a particular wavelength or the integral of fluorescence over the emission spectrum.

"Operatively inserted" or "linked" refers to a juxtaposition wherein the components so described are in a relationship permitting them to function in their intended manners. A control sequence operatively linked to a coding sequence is ligated such that expression of the coding sequence is achieved under conditions compatible with the control sequences.

"Responsive" is intended to encompass any response of a polypeptide or protein to an interaction with an analyte.

Description

Rapid transient changes of cytosolic calcium level leads to various physiological actions. There is an ongoing need to develop calcium sensors with fast calcium-binding kinetic properties and pH-independent fluorescence change to probe calcium fluctuation in high calcium environments like endoplasmic reticulum. The present disclosure provides embodiments of engineered variants of the red calcium sensor Rapid ER (MCD1) with fast kinetics with a $k_{off}$ between about 800 $s^{-1}$ and about 2500 $s^{-1}$, including but not limited to about 1900 $s^{-1}$) and a $k_0$ greater than $2.7 \times 10^7$ $M^{-1}$ $s^{-1}$. Half-shell coordination, negatively-charged solvent accessible area, electrostatic binding energy change, and the hydrogen bonding network of the chromophore provide factors to control calcium-binding affinity, kinetics and calcium-binding-dependent change of optical properties.

Calcium-binding results in an increase of the quantum yield and calcium titration showed a fluorescence signal increase with a $K_d$ of 0.1 mM. Tryptophan-$Tb^{3+}$ FRET and $Tb^{3+}$-RapidER (MCD1) FRET support that calcium binds to the artificial i.e. engineered binding sites of the sensors of the disclosure. The pH stability of the red sensors was enhanced, with a $pK_a$ below 5, compared to engineered GFP-derived calcium sensors. The results further showed the developed calcium sensors of the disclosure are able to monitor endoplasmic reticulum (ER) calcium release responses to activators and inhibitors of the calcium channels in ER membrane and thus demonstrate that the metal ion sensors of the disclosure are useful for detecting, both qualitatively and quantitatively rapid changes in calcium ion concentration in living cells. The in vitro data illustrating the optical property changes that occur in the red fluorescent sensors of the disclosure provide support for their use as metal ion (e.g. calcium, but not limited thereto) detectors in a non-cellular environment such as in an aqueous solution, or if the sensors are bound to such as a solid support.

Key Factors for Binding Affinity and Kinetic Properties:

Calcium-binding accepts a flexible coordination number from 3-8. Because it is a soft metal, oxygen is preferred to be the coordinator. From a statistical analysis of calcium-binding sites in protein data banks, aspartic acid, glutamic acid and water are the principal three residues providing oxygen to bind calcium ion.

The calcium-binding features of protein-based calcium indicators have been mainly determined by the calcium-binding moiety (calmodulin (CaM) or troponin C (TnC)) involved. The calcium-binding affinity of both CaM and TnC is about $10^{-6}$-$10^{-7}$ M. The stoichiometry for both calmodulin and troponin C is 1:4, two calcium ions in each terminal domain. The calcium-binding follows a cooperative manner in each domain, which may contribute to the slow calcium dissociation-rate of between about 0.2-$s^{-1}$ to about 20 $s^{-1}$. In addition, the two domains are relatively independent, resulting in the biphasic calcium-binding curve observed in the sensor Cameleon.

Efforts have been taken to reduce the $K_d$ of previously known GECIs. Thus, in the sensor Cameleon 3, the mutation E104Q locating in the third EF-hand motif in CaM domain eliminated the high calcium-binding component of the CaM C-domain and the $K_d$ value of is 4.4 μM. For Cameleon 4, the mutation E31Q locating in the first EF-hand motif further decreased the binding affinity in CaM N-domain but did not significantly affect the high affinity C-domain. The resulting $K_d$ of Cameleon 4 is 83 nM and 700 μM with hill coefficients 1.5 and 0.87 respectively. The charged residue in the interface switched between M13 and CaM decreased the apparent $K_d$ (0.8 and 60 μM) and increased the $k_{off}$ (256 $s^{-1}$), although the original purpose was to eliminate perturbation of the normal calcium signaling by interaction with their intrinsic target proteins. A similar situation was observed in a recent version of GCaMP that was generated by altering the interface between M13 and CaM as well as the one between CaM and cpEGFP. GCaMP6f exhibited faster calcium response to action potentials in neuronal activity than other GCaMPs. These results showed that the apparent $K_d$ of the calcium indicators involving CaM and M13 peptide was not only determined by the calcium-binding motifs, but also the linker and domain interface.

TnC also has two terminal domains like CaM. The N-terminal domain binds $Ca^{2+}$ with lower affinity than C-domain, which is a regulatory site. The TnC molecule undergoes structural rearrangement after Calcium-binding. TN-XL with faster kinetics than TN-L15 was created by switching the residue N and D at position 109, 111, 145 and 147 at the third and fourth EF-hand motifs in C-terminal domain of TnC, whereupon the calcium-binding affinity was lowered ($K_d$=2.2 μM, Hill coefficient 1.7). Magnesium interference was also abolished. The resulting off-rate of TN-XL measured by stopped-flow spectrometer was around 5 $s^{-1}$, approximately 5-fold greater than TN-L15 and TN-XXL.

The cooperative binding, the slow dissociation kinetics and the high calcium-binding affinity are signatures for native calcium-binding proteins of GECIs. In addition, the $K_d$ is not controlled by the calcium binding alone due to the multiple steps required for fluorescence signal change. Therefore, it is has proven difficult to tune the binding affinity and kinetics as well as to avoid cooperativity in the same construct by rational design. In contrast, the GFP-based sensor CatchER (SEQ ID NO: 37) had improved fast kinetics, low calcium-binding affinity and 1:1 stoichiometry by avoiding the native calcium-binding moiety. In such a simplified calcium indicator as CatchER (SEQ ID NO: 37), the calcium-sensing relies on the local dynamics in the calcium-binding site. Accordingly, the simple calcium-binding site engineered into CatchER (SEQ ID NO: 37) was a useful basis for modifications to increase the kinetics further by reducing the positively charged residues around the binding site.

Compared with CatchER (SEQ ID NO: 37), the RFP-based RapidER (MCD1) (SEQ ID NO: 43) of the present disclosure, and variants thereof, has a higher calcium-binding affinity as well as faster kinetics, in agreement with the calculation of the electrostatic binding energy change and the negatively-charged solvent accessible surface area. The faster calcium dissociation rate in both CatchER (SEQ ID NO: 37) and RapidER (MCD1) (SEQ ID NO: 43) than in previously used EF-hand motif can be attributed to the geometry of the designed half-shell calcium-binding site, where there is little steric barrier for calcium release. However, there are three positively charged residues: K74, K166 and R220, around the calcium-binding site in RapidER (MCD1) (SEQ ID NO: 43) compared to CatchER (SEQ ID NO: 37), where there is only one K42 nearby. The edge of the enlarged negative circle may also be neutralized by these positive residues and thus increased the dissociation-rate. The evidence for the role of the positive residues around the binding site can be found in the crystal structure of $Ca^{2+}$-CatchER CatchER with a calcium ion bound thereto), where there were two populations of calcium ion positions observed, both of which are coordinated by E147 but away from E223 and E225 that are close to K42. It is likely that positively charged residues around the calcium-binding site attract electron density to increase the dissociation-rate.

Electrostatic energy changes and solvent accessible areas in MCD1 and variants thereof were compared to CatchER are shown in Table 1.

TABLE 1

The electrostatic binding energy calculation

| Proteins | Coulombic Energy (kT) | $\Delta G_{elec\_mut}$ (kT) | $\Delta G_{elec\_binding}$ (kT) | Negatively charged SAA ($Å^2$) |
|---|---|---|---|---|
| mCherry | −4165.8 | | | |
| RapidER (MCD1) (SEQ ID NO: 43) | −3201.3 | 964.45 | −73.03 | 655.188 |
| $Ca^{2+}$-MCD1 | −4053.8 | 111.96 | −852.49 | |
| EGFP | −3596.6 | | | |
| CatchER (SEQ ID NO: 37) | −3223.9 | 372.71 | −59.48 | 589.203 |
| $Ca^{2+}$-CatchER | −3905.0 | −308.35 | −681.06 | |

Positions of Calcium-Binding Sites:

Red Fluorescent Protein (RFP) has a larger conjugated system than that of Green Fluorescent Protein (GFP), which was extended to the backbone of F65 before the cyclized chromophore tri-peptide. Like GFP the chromophore environment of RFP plays important roles in maintaining fluorescence. The side-chain orientation of the neighboring residues in β sheets is usually opposite. Those projecting to the interior of the β-can form hydrophobic or electrostatic interactions to participate in or protect the chromophore environment, while the others facing the solvent assist to keep the protein from aggregation or degradation. The residues with side chains in the interior of the protein have more direct contact with the chromophore so as to affect the optical property directly.

For example, mutation of the E215 in mCherry resulted in the blue shift of the spectrum, where the original E215 was protonated and formed a hydrogen bond between the protonated carboxyl group and the imidazolinone ring nitrogen. However, calcium-binding in the surface of the β-barrel mainly involves the side chains protruding outside. hi order to change the spectral properties by calcium-binding, the designed calcium coordinators need to influence those residues in the chromophore environment.

As shown in FIG. 1, in the chromophore of mCherry, the chromophore phenol hydroxyl group is close to the opening of the β-barrel, where a loop region is located. The corresponding location in GFP served as a tunnel to allow proton migration during excited state proton transfer. This phenolate oxygen formed H-bonds to the side chain of S146 (both states), to the main chain of E144 through a bridging water molecule (wat1), and to the side chain of Q163. E215 in mCherry has been proposed to be protonated to form an H-bond with imidazolinone nitrogen. The position of this residue is relatively rigid because a network was observed among the chromophore, E215, Q42, S69 and a water molecule (wat4 shown in the FIG. 1). Both main chains and side chains of these three residues together with the chromophore have contact with each other, leading to a tight association. H-bonds were found from the side chains of R95 and Q64 to the imidazolinone oxygen. Since the peptide bond connecting F64 and the chromophore was part of the conjugated system in mCherry, the main-chain oxygen in F64 was also under consideration, which formed H-bonds with the side chain Q109 and S111 via water molecules.

Thus, three potential calcium-binding sites were selected to affect the phenol group. Pocket 1 of RapidER (MCD1) (SEQ ID NO: 43) was one, including the mutation A145E between E144 and S146. Pocket 2 includes E144, and pocket 3 had the mutation E164 adjacent to Q163. Pockets 1 and 2 had mutations R216E next to E215. Pocket 4 was selected as near R95 and Q109, including mutations K92E and T108E. The results suggested that only variants of pockets 1 and 2 show a calcium-dependent fluorescence change. The equilibrium-dialysis assay confirmed that variant MCP6 (SEQ ID NO: 48) (K92E/E94/T108E/D110) belonging to the pocket 6 variants also bound calcium with a binding affinity comparable to those of pockets 1 and 2.

The lifetime of $Tb^{3+}$-RapidER (MCD1) FRET verified that the calcium went to the expected position in RapidER (MCD1) (SEQ ID NO: 43). Calcium-binding increases the lifetime of RapidER (MCD1) (SEQ ID NO: 43) and thus the quantum yield was enhanced. Therefore, the phenol hydroxyl group was more sensitive than others to the change of the electrostatic environment and consequently has the major potential to affect the optical property.

Accordingly, the design strategy of the disclosure of combining the chromophore environment and the calcium-binding site correlates the calcium-binding and the fluorescence change. The half-shell design allows the creation of a single calcium-binding site with the dissociation constant in the range of 0.1-0.5 mM in vitro. The introduction of mutations results in decreases of the extinction coefficient and the quantum yield. Calcium-binding does not change the extinction coefficient but increases the quantum yield back to a level similar to that of the wild type mCherry. RapidER (MCD1) (SEQ ID NO: 43) was named as such because of the recognition of its fast calcium-binding kinetics. Compared to GFP-based calcium-binding proteins, RapidER (MCD1) (SEQ ID NO: 43) showed less pH-dependent fluorescence change in physiological range. It successfully detected the calcium release from endoplasmic reticulum resulting from administration of the calcium ionophore, the activators of RyR and $IP_3R$, and an inhibitor of SERCA to mammalian cells. The variant proteins of the disclosure are advantageous for improving the dynamic range of fluorescence change upon calcium-binding and expand the spectrum window and the measurable range of calcium concentration of available calcium sensors.

Embodiments of the metal ion sensors according to the disclosure comprise a fluorescent host polypeptide and a molecular recognition motif that interacts with an analyte (e.g., calcium (or other metal as noted herein) or a flux of calcium in its microenvironment. Upon interaction of a metal ion analyte with the molecular recognition motif, the sensor generates an optically-detectable signal (or the optically-detectable signal is altered) which is produced during exposure to an analyte. The molecular recognition motif is integrated or operatively linked into (within the amino acid sequence) a fluorescent host polypeptide. The interaction of the analyte with the molecular recognition motif produces a detectable change in fluorescence properties (e.g., change of the intensity, or maxima wavelength or the imaging of the absorption, transmitted light, fluorescent excitation or emission change, light scattering, and/or energy transfer of the chromophore and the protein) of the metal ion sensor based on the quantity of the analyte.

Using relevant molecular recognition motifs, the metal ion sensitive sensors of the disclosure can be used to investigate the mechanisms of diseases, track the process of diseases and diagnose some diseases related to analyte activity in vitro, in living cells and in vivo. In addition, a specific signal peptide can also be useful for investigating mechanisms such as their activation or inhibition of diseases related to calcium (or other metals as noted herein) activities in various cellular compartments in real time and in situ, which is useful in biotechnology, cell biology and medicinal chemistry, disease diagnosis and prognosis, calcium inhibitor screening and drug development.

Embodiments of the metal ion sensors of the disclosure, therefore, include an engineered fluorescent host polypeptide having a metal ion binding site comprising a plurality of negatively charged residues, wherein the negatively charged residues comprise a plurality of carboxyl oxygens orientated in a pentagonal bipyrimdal geometry wherein said geometry provides a metallic ion binding site operatively interacting with a chromophore region of the engineered fluorescent host polypeptide such that binding of a metal ion analyte to the molecular recognition motif modulates the emission of a fluorescent signal emitted by the fluorescent host polypeptide, and optionally, the absorbance spectrum of the engineered fluorescent host polypeptide.

Upon interaction of the analyte (e.g., calcium, lead, and/or lanthanide) with the analyte binding site, the metal ion sensor produces an altered signal relative to the metal ion sensor prior to interaction. In this regard, the relative three dimensional position of the chromophore within the fluorescent host polypeptide is altered upon interaction of the analyte with the analyte binding site, where such alteration generates the altered signal. The ratiometric change of the signal (chromophore signal) after the interaction allows an accurate measurement of the analyte activity (e.g., in vitro and in vivo with normalized sensor concentration). The inclusion of the structure motif allows optimal molecular recognition by incorporating essential structural and chemical properties required for a specific type of analyte. For example, inclusion of the structure motif allows for: solvent accessibility for the easy access of calcium, flexiblility required for the recognition, a special geometric pocket for the interaction, a hydrophilic surface or charged environments to facilitate the binding process and a required environment for the fast kinetic rates such as good off rate required for real time measurements.

In other words, the metal ion sensors have a folding arrangement in a three-dimensional space that produces a specific signal. The metal ion sensor can undergo a local conformational change into another folding arrangement with an alteration of the chromophore microenvironment under the inducement of an analyte (e.g., calcium, lead, or a lanthanide) with the analyte binding site. The conformational change can be detected and measured and compared to the signal generated by the calcium sensor prior to interaction with the analyte.

The advantages of embodiments of the present disclosure can include one or more of the following: (i) embodiments of the present disclosure are capable of monitoring numerous cellular events in living cells or organisms via live cell imaging. Embodiments of the present disclosure can provide continuous and dynamic movies of the cellular event and their responses by the stimuli or drugs. Embodiments of the present disclosure largely overcome the limitations of currently commercial available small molecule dyes, peptide/mimics probes with one snap shot of the analyte action; (ii) embodiments of the present disclosure include single fluorescent proteins that are more easily and better translocated under cellular environment to probe analyte reaction in situ than FRET pairs that used two fluorescent proteins. With the addition of signal peptides, these metal ion sensors can be specifically expressed/placed at the cellular environments such as ER, mitochondrial, Golgi or nuclei to monitor cellular event with spatial resolution in addition to temporal resolution. Currently available dye detection methods simply rely on passive diffusion of the probe through the membrane, and permits only short snapshots of calcium actions without the capability of detecting reactions at targeted cellular locations. These probes do not provide continuous dynamic imaging of calcium actions due to limited cellular lifetime and specificity; (iii) embodiments of the present disclosure do not use existing/natural calcium binding proteins to sense metal ions (e.g., calcium, lead, or a lanthanide), thus they have minimized perturbation of cellular network; (iv) embodiments of the present disclosure include single fluorescent protein units that overcome the limitations observed with FRET-based sensors that are prone to fluorescence photobleaching, poor orientation and translocation in the cellular compartments due to their large size; (v) the ratiometric signal change of embodiments of the present disclosure with absorption or excitations at wavelengths such as 398 and 490 nm permit quantitative and accurate measurement of the calcium (or other metal as noted herein) action by normalizing the concentration change of the sensors and cellular and instrumental interference of the fluorescence signal; (vi) creating different sensors with different metal ion affinities allows for monitoring of cellular response with high accuracy and sensitivity; (vii) the structural motifs used in embodiments of the present disclosure allow the maximal optical responses as well the optimal molecular recognition required for chemical reactions; and (viii) the developed metal ion sensors can be expressed in bacterial, mammalian cells, and animals such as mice with good optical properties such as those described herein. The changes in the fluorescent and absorbance properties of the engineered polypeptides of the disclosure inducible by metal ion binding may also be used to detect the removal of the metal ion resulting in a reverse change.

Thus, the systems, sensors, and methods of the present disclosure can be used to detect, measure, quantitate, and image interactions between the analytes with the analyte binding site, in vitro and in vivo. In particular, embodiments of the present disclosure can be used to detect (and visualize) and/or quantitate calcium interactions or events in vitro as well as in in vivo. In addition, the systems, sensors, and methods of the present disclosure can be used to detect, measure, quantitate pH change with the analyte binding site, in vitro and in vivo. Furthermore, the systems, sensors, and methods of the present disclosure can be used to control the concentration of an analyte in a system.

Based on the fluorescence properties of the metal ion sensor, a DNA construct of the metal ion sensor may be inserted into a recombinant vector or any suitable vectors that may conveniently be subjected to recombinant DNA procedures. The specific vector can depend on the type of host cells. For example, recombinant DNA plasmid vectors, which can exist as an extrachromosomal entity, may be a suitable vector. Alternatively, the vector may be one that, when introduced into a host cell, is integrated into the host cell genome and replicates together with the chromosome(s) into which it has been integrated. Once the metal ion sensor has been constructed, vectors comprising the fluorescent nucleic acid molecules may be formulated into a variety of compositions, such as solutions (for example, buffer solutions) to be used in transfecting host cells.

A fluorescent host polypeptide or variant thereof according to the disclosure can be linked to a molecule directly or indirectly, using any linkage that is stable under the conditions to which the protein-molecule complex is to be exposed. Thus, the fluorescent host polypeptide and molecule can be linked via a chemical reaction between reactive groups present on the protein and molecule, or the linkage can be mediated by a linker moiety, which contains reactive groups specific for the fluorescent host polypeptide and the molecule. It will be recognized that the appropriate conditions for linking the fluorescent host polypeptide variant and the molecule are selected depending, for example, on the chemical nature of the molecule and the type of linkage desired. Where the molecule of interest is a polypeptide, a convenient means for linking a fluorescent host polypeptide variant and the molecule is by expressing them as a fusion protein from a recombinant nucleic acid molecule, which includes a polynucleotide encoding, for example, a fluorescent host polypeptide operatively linked to a polynucleotide encoding the polypeptide molecule.

The metal ion sensor may be produced as chimeric proteins by recombinant DNA technology. Recombinant production of proteins including fluorescent host polypeptides involves expressing nucleic acids having sequences that encode the proteins. Nucleic acids encoding fluorescent host polypeptides can be obtained by methods known in the art. For example, a nucleic acid encoding the protein can be isolated by a polymerase chain reaction of DNA from a *Discosoma* sp. using primers based on the DNA sequence of a *Discosoma* sp. RFP. Mutant versions of fluorescent host polypeptides can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

A molecular recognition motif can include the analyte binding site, one or more structural motif, and a targeting motif. The analyte binding site and the structural motif can include those described above. The targeting motif can target organelles and sub-organelles such as, but not limited to, ER, mitochondrion, Golgi, nucleus, channels, gap junctions, and extracellular spaces. The targeting motif includes, but is not limited to, signal peptides encoded in the proteins located in the target organelles. As disclosed above, the motifs can be positioned differently than described herein as long as they have characteristics that are consistent with the embodiments disclosed. Additional details and the examples that describe specific embodiments of the present disclosure are provided below.

The present disclosure provides for metal ion sensors that comprise a molecular recognition motif that binds a metal ion analyte (e.g., calcium, lead, and/or lanthanide) and a fluorescent host polypeptide in which the molecular recognition motif is operatively linked to or integrated therein. Interaction of the analyte with the molecular recognition motif produces a detectable change. The metal ion sensors of the disclosure can have a protein sequence that includes the molecular recognition motif and the fluorescent host polypeptide selected from: SEQ ID NOs: 41-63, or conservative variants thereof.

Methods of Use:

It is contemplated that the metal ion sensors of the disclosure can be used in vivo and/or in vitro. The metal ion sensors or systems expressing such sensors of the disclosure can be introduced into a cell or host, the metal ion sensors or systems can be expressed in the system, and/or the metal ion sensors or systems can be included in a transgenic animal or plant. The metal ion sensor can include a specific signal peptide for the delivery of the metal ion sensor to different subcellular compartments such as cytosol, nucleus, mitochondrial matrix, endoplasmic reticulum, golgi and peroxisome, and the like.

Embodiments of the present disclosure provide for methods of detecting and measuring a metal ion analyte. The methods can include: introducing an metal ion sensor into a system; allowing the metal ion sensor to interact with the analyte of interest, which can interact with the analyte binding site of the metal ion sensor; and detecting or measuring the fluorescent properties or changes derived from the fluorophore operable linked to the analyte binding site. As the change in fluorescent activity of the metal ion sensor is a proxy for the activity of the analyte of interest, this method provides a means for studying and evaluating analyte activity.

Embodiments of the method of the disclosure can include: introducing a plasmid encoding the metal ion sensor into a host cell by standard gene transfer methods; expressing the metal ion sensor in the host cell; allowing the metal ion sensor to interact with the analyte of interest, which can interact with the analyte binding site of the metal ion sensor, and thereby detect or measure a fluorescent signal or changes. As the change in fluorescent activity of the metal ion sensor is a proxy for the activity of the analyte of interest, this method provides a means for studying and evaluating analyte activity.

The methods can include: introducing an metal ion sensor into a system; allowing the metal ion sensor to interact with a metal ion analyte which can interact with the analyte binding site of the metal ion sensor; and detecting or measuring the fluorescent properties or changes, which can be correlated to a pH change.

Embodiments of the present disclosure can further provide for methods of controlling the concentration of one or more metal ion analytes. In an embodiment, the methods can include: introducing an metal ion sensor into a system; allowing the metal ion sensor to interact with the analyte, which can interact with the analyte binding site of the metal ion sensor. The bonding of the analyte with the analyte controls the amount of analyte in the cell or host.

Samples useful with this disclosure include biological samples, environmental samples, or any other samples for which it is desired to determine whether a particular molecule is present therein. The sample can be, but is not limited to, a living cell or a cell extract, which may be obtained from an animal or a plant. Alternatively, the cells can originate from or be derived from bacterial cells. Further, the cells may be obtained from a culture of such cells, for example, a cell line, or can be isolated from an organism. Where the method is performed using an intact living cell or a freshly isolated tissue or organ sample, the presence of a molecule of interest in living cells can be identified, thus providing a means to determine, for example, the intracellular compartmentalization of the molecule in real time.

Detecting with the Metal Ion Sensor:

Methods for detecting with the metal ion sensor or of a cell expressing containing an metal ion sensor may include, but are not limited to, illuminating the metal ion sensor or cell expressing the sensor with an illumination source such that the metal ion sensor or cell expressing the metal ion sensor emits a radiation. Such detection methods may use an illumination source such as an incandescent light source, a fluorescent light source, a halogen light source, sunlight, a laser light, and other equivalent sources. When illuminated by such an illumination source, the metal ion sensor can emit fluorescent light that may be detected by unaided optical observation or by other qualitative or quantitative methods. Suitable methods for measuring fluorescence of samples are known and understood by those with ordinary skill in the art.

CatchER Variant Calcium Sensors

To address the pressing need to detect the calcium concentration in a high-calcium environment such as the ER/SR, a modified EGFP, designated CatchER (Calcium sensor for detecting high concentration in the ER) was designed as a sensitive fluorescence calcium probe (Tang et al., (2011) *Proc. Natl. Acad. Sci. USA* 108: 16265-16270). CatchER was generated by the addition of a calcium binding site formed by five calcium ligand residues (residues 147, 202, 204, 223, and 225) in the beta-barrel in proximity of the phenol group of the chromophore from the single enhanced green fluorescent protein (EGFP) carrying the deprotonated chromophore (CRO) with resolution 1.20. Excitation of both the neutral and anionic chromophore leads to the dominating anion emission at 510 nm, indicating the occurrence of the excited state proton transfer (ESPT). The fluorescence increase accompanied by the increasing calcium concentration, follows a 1:1 binding curve. The absorbance spectra showed that the population of the neutral form (ROH) decreased while the anionic form (RO$^-$) increased when calcium concentration increased. Fluorescence studies showed that the fluorescence intensity of the Ca$^{2+}$-bound CatchER increased when CatchER was excited at both neutral ($\lambda_{abs}$ 395 nm) and anionic ($\lambda_{abs}$ 488 nm) forms. CatchER exhibited unprecedented Ca$^{2+}$ release kinetics with an off-rate estimated around 700 s$^{-1}$ and appropriate Ca$^{2+}$ binding affinity for detecting high concentration in the ER. CatchER is able to measure the calcium concentration change in various cell types and monitor SR luminal Ca$^{2+}$ in flexor digitorum brevis muscle fibers to determine the mechanism of diminished SR Ca$^{2+}$ release in aging mice using the intensity-based fluorescence imaging.

The present disclosure now provides embodiments of the EGFP-derived metal ion (calcium) sensors specifically targeted to a cellular organelle, allowing the measurement of intracellular calcium concentrations and the kinetics of changes in intracellular calcium levels. The embodiments of the Catcher variants herein disclosed have increased thermal stability compared to CatchER itself. The embodiments further include heterologous target-specific motifs that allow for localization of expressed sensors to target cellular organelles complicit in calcium-based cell processes. For example, but not intended to be limiting, the targeting sequence from segments of the transmembrane domains of RyR1, and used FKBP12 (FK506 binding protein)-CatchER chimera protein to anchor a sensor such as CatchER to the ER membrane and allow CatchER to face cytoplasm to enable investigation the amplitude and kinetics of calcium release from the SR during CICR.

In one embodiment, to obtain the clone of CatchER-FKBP fusion protein (encoded by the nucleotide sequence SEQ ID NO: 6), FKBP12 was fused to the C-terminal of CatchER without any targeting sequence in pcDNA3.1(+). A linker of Gly-Gly-Ser-Gly-Gly (SEQ ID NO: 84), along with the restriction enzyme C/al site was inserted between CatchER and FKBP12.

The rabbit ryanodine receptor 1 (GenBank: X15209) transmembrane domain M5 and M10, based on Zorato's RyR1 topology model (Ma et al., (2004) *Cell Biochem. Biophys.* 40: 207-224), were applied as the ER membrane anchoring sequence. The extended Z5 (4551-4597) (SEQ ID NO: 76) only can anchor GFP to the ER membrane (Meur et al., (2007) *J. Biol. Chem.* 282: 23096-23103). Extended Z10 (4907-4943) (SEQ ID NO: 77) is composed of 37 amino acids and is the last transmembrane (TM) domain in the rabbit ryanodine receptor 1 model.

Figure 17:
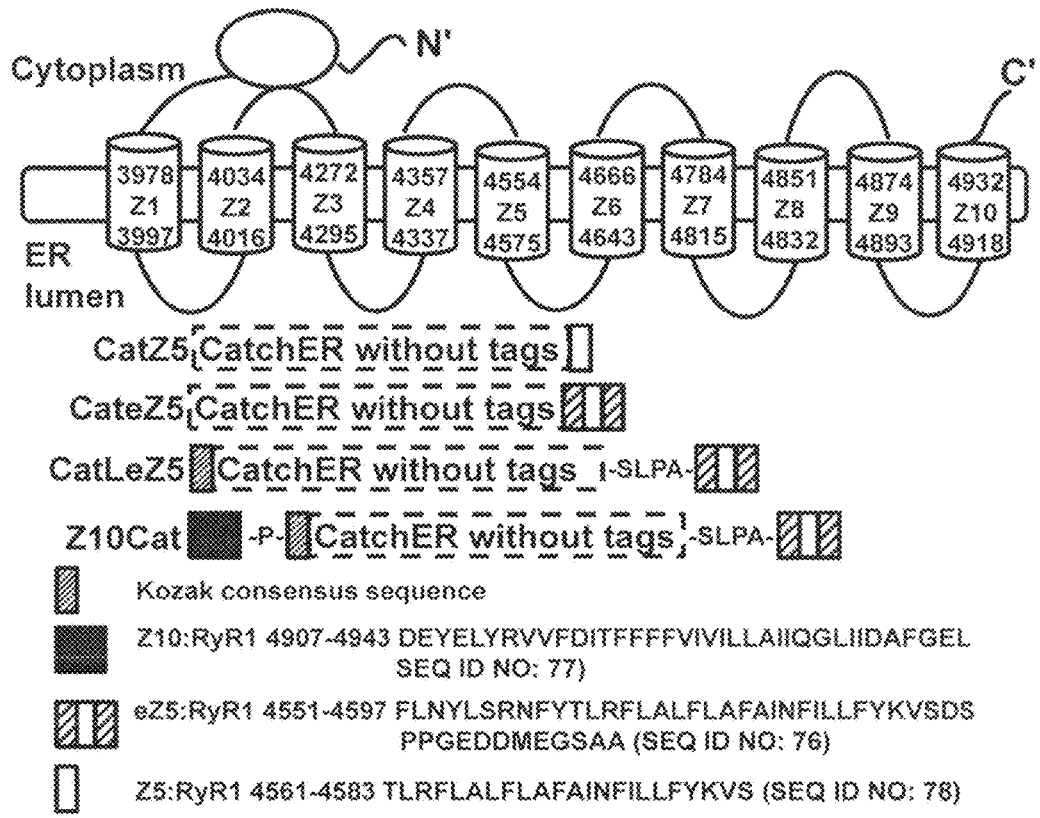
FIG. 17 illustrates the construction of ER-anchoring CatchER variants. (Top) The Zozrato's RyR1 topology model. Z5 and Z10 domains are the selected anchoring sequences. (Bottom) The chimera of Z10-CatchER-Z5. The extended Z5 (4551-4597) (SEQ ID NO: 76), Z5 (4561-4583) (SEQ ID NO: 78), and Z10 (4907-4943) (SEQ ID NO: 77) motifs were fused to the C terminal, or N terminal of CatchER.

As illustrated in FIG. 17, the extended Z5 (4551-4597) (SEQ ID NO: 76), Z5 (4561-4583) (SEQ ID NO: 78), and Z10 (4907-4943) (SEQ ID NO: 77) motifs were fused to the C terminal, or N terminal of CatchER with neither calreticulin targeting sequence nor ER retention sequence (Lys-Asp-Glu-Leu, SEQ ID NO. 83), to allow the protein to face to the cytosol, respectively. The consensus translation initiation Kozak sequence (gccaccATGG, SEQ ID NO: 85) was placed between the Z10 (SEQ ID NO: 77) sequence followed by a proline and CatchER. A linker composed of four amino acids Ser-Leu-Pro-Ala (SEQ ID NO: 86) was inserted between CatchER and extended Z5 (eZ5) (4551-4597) (SEQ ID NO: 76) to separate the transmembrane region from the calcium sensor. The hot start KOD DNA polymerase kit was used for the PCR reaction. The ligation was carried out using T4 DNA ligase (New England Biolabs) at 4° C. for 48 h.

C2C12 myoblasts were induced to differentiate by changing 2% FBS DMEM and used to investigate specific targeting of the CatchER variants to the ER/SR membrane. All ER membrane targeted constructs, including CatZ5, CateZ5, CatLeZ5, and Z10Cat were tested by fluorescence immunostaining for the cellular distribution C2C12 myoblasts. The confluency of C2C12 cells was maintained at approximately 30-40% to avoid the differentiation. Cover slips 0.5 mm thick were used for seeding cells and 1.5 µg plasmid DNA encoding the calcium-sensor was transfected. Cells were cultured at 30° C. for 48 h before imaging. Cells were fixed to the cover slip with 3.7% formaldehyde. Triton X-100 and digitonin were used for permeablizing membranes. Digitonin is able to complex with sterol-like cholesterol that is a component of the cell membrane, but not the ER membrane, and thus disrupts the packing of the lipid bi-layer. Triton X-100 is a detergent that can solubilize all membranes. The cover slip was blocked by PBS containing 5% BSA and the primary antibody (anti-GFP or anti-Calnexin) was added. The secondary antibody conjugated with Alexa Fluor dyes was applied for imaging using the confocal microscopy ZEISS LSM 700 with a resolution of about 50-100 nm, which is not able to distinguish whether the protein is anchored in the ER membrane or free in the ER lumen.

Figure 18:
FIG. 18 illustrates digital confocal images of targeted CatchER in non-differentiated C2C12 myoblasts.
Figure 19:
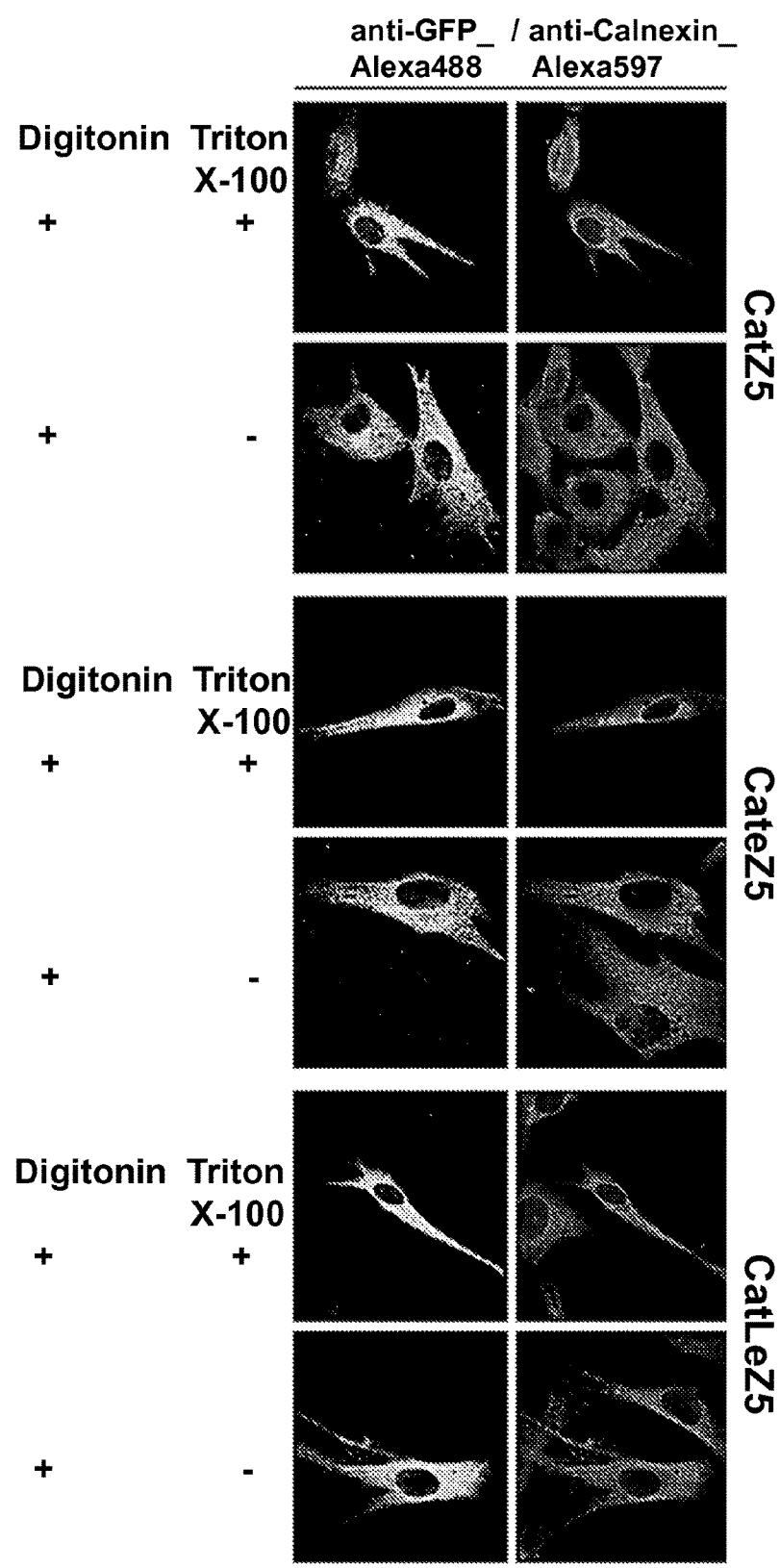
FIG. 19 illustrates digital confocal images of targeted CatchER in non-differentiated C2C12 myoblasts. Both anti-GFP and anti-Calnexin antibodies were used together. Secondary antibody conjugated with Alexa Fluor488 was used for GFP and Alexa Fluor597 for calnexin. Before fixed with formaldehyde, digitonin at the final concentration of 25 µM was added to PBS and incubated for 3 min to permeabilize plasma membrane. Incubation with 0.2% Triton X-100 in for 5 min PBS was used to disrupt all cell membranes.

With treatment with digitonin without pre-fixation, the self-fluorescence of Z10Cat expressed in C2C12 myoblasts showed the reticular architecture (FIG. 18), which was co-localized with calnexin. The fluorescence of CatZ5, CateZ5 and CatLeZ5 was not as bright as CatchER. Therefore, anti-GFP antibody was applied for visualizing the distribution of targeted sensors. Similarly with Z10Cat, the ER reticular network was observed for these three targeted sequences (FIG. 19), suggesting the membrane association and the location in the cytosolic side. However, there remained possibility that some Z10Cat remaining in the ER lumen.

Cell imaging studies were carried out to evaluate the CatchER FKBP and ER anchoring sequences fusion. Plasmid DNA (1.5-2.0 µg) encoding the targeted CatchER was transfected to non-differentiated C2C12 myoblasts at a confluency of about 30% and the cells were cultured at 30° C. for 36-48 h. To express CatchER-based sensors in the induced differentiated C2C12 cells, DMEM was substituted with the differentiation medium containing 2% FBS when the cell confluency reached 70%. Plasmid DNA (2 µg) was transfected 72 h after changing medium. Cells were cultured at 30° C. for 1 week before imaging.

FIG. 20A illustrates the calcium concentration change induced by RyR1 agonist 4-cmc (100 µM), ATP (100 µM), SERCA pump inhibitor thapsigargin (1 µM), ionomycin (10 µM) and digitonin (25 µg/ml) that was monitored by Cat-FKBP in C2C12 myoblasts.

After differentiation began, the C2C12 cells grew in parallel generally and appeared long and thin (FIG. 20B). DNA transfection efficiency in the differentiated C2C12 cells was low so only a single cell in the observation field was recorded. The fluorescence intensity was not as bright as CatchER expressed in C2C12 myoblasts. The color contrast formed between the nucleus and cell plasma could be distinguished, and the nucleus region was darker. After digitonin permeabilization, the fluorescence was maintained in the perinuclear region, while only auto-fluorescence was seen in other regions, implying that the majority of Cat-FKBP was free in cytosol and a portion was able to bind RyR1. Applying caffeine caused fluorescence intensity fall by about 7%. Without extracellular calcium, it did not recover after 4-cmc triggered fluorescence decrease. After being permeabilized, intensity decreased slightly by adding 4-cmc. The drug treatments indicated there was CatchER expressed in ER lumen.

For differentiated C2C12 cells, several nuclei can be found in the long tubule-like cell (FIG. 21). The basal fluorescence intensity was very low. A perinuclear pattern of fluorescence was observed. After permeabilization, intensity dropped by about 40%, indicating approximately half of the CatZ5 was either free in cytosol or not anchored to the membrane. The remaining CatZ5 responded to the switch of low and high calcium solution.

Due to limitations of the brightness of CateZ5, it was difficult to subtract the photobleaching and autofluorescence from the total observed fluorescence. Accordingly, to enhance fluorescence, a linker composed of the four amino acids Ser-Leu-Pro-Ala (SLPA) was inserted between CatchER and the eZ5 fragment as encoded by the nucleotide sequence SEQ ID NO: 5.

Although the brightness was enhanced by inserting the linker, the presence of free cytosolic and the luminal CatLeZ5 still remained problems. Another transmembrane domain of RyR1, Z10 (SEQ ID NO: 77), was fused to N-terminal of CatchER. The resulting construct Z10Cat encoded by the nucleotide sequence SEQ ID NO: 2) was brighter than CatLeZ5, and the brightness under microscope was comparable with CatchER.

For differentiated C2C12 cells, as shown in FIG. 22, Z10Cat responded like ER luminal CatchER, where 4-cmc and caffeine induced fluorescence decrease by 6% (2 min), and 10% (40 mM) and 4% (10 mM). There was around 30% fluorescence decrease after digitonin treatment, more than that observed in non-differentiated C2C12 cells. The dynamic range of 10% was seen in response to 10 mM $Ca^{2+}$.

Binding FKBP to RyR1 is the pre-requisite for CatFKBP targeting to the ER. Thus CatFKBP failed to form a reticular network in C2C12 myoblasts lacking the RyR1 expression and it could form the prinuclear pattern after permeabilization of plasma membrane in differentiated myotubule, as shown in FIG. 20B. The calcium imaging for CatFKBP demonstrated that this construct could be used in differentiated C2C12 cells after the plasma membrane was permeabilized. However, the endogenous FKBP occupies the RyR1 so that the binding of CatFKBP decreases.

To minimize interactions between CatchER and the targeting domain, the peptide length was kept as short as possible. Hence, a single transmembrane domain was first taken into account. The Z5 motif (SEQ ID NO: 78) failed to target the fusion protein to the membrane in either C2C12 myoblasts or the differentiated C2C12 cells. Compared to Z5, the longer sequence eZ5 (SEQ ID NO: 76) was better at ER targeting in the C2C12 myoblast. The result is in agreement with reports indicating the eZ5 sequence alone is sufficient for ER targeting of RyR1 in COS cells. However, the eZ5 was not successful in the differentiated one either. Besides that, the fusion with the transmembrane domains also traded in the brightness. Among the current four RyR1 transmembrane fragment-fused CatchER, CatLeZ5 is the most advantageous because it takes the advantage of good targeting in the differentiated C2C12 cells and relatively good brightness.

Table 2 lists the amplitude and the time-to-peak of 4-cmc-induced calcium release detected by CatchER with the different targeting fragments (eZ5, Z5, and Z10) in C2C12 myoblast and differentiated cells, as well as the loss of CatchER fluorescence after digitonin permeabilization. Accordingly, the sensors of the disclosure allow the targeting of CatchER to SR membrane to investigate calcium dynamics in the plasma/SR membrane junction.

TABLE 2

Data summary of CatchER with different tags in calcium imaging

| | C2C12 myoblast | | | |
|---|---|---|---|---|
| Tagged CatchER | 4-cmc %\|Time-to peak(sec) | $k_{off}$ $(s^{-1})$ | Digitonin % | Brightness % |
| CatchER | 30\|60 | 0.022 | 10 | Saturated[a] |
| Cat-cyt | 10\|60 | 0.034 | 100 | Saturated[a] |
| CatFKBP | 25\|75 | 0.050 | 90 | >150 [b] |
| CatZ5 | 20\|90 | 0.034 | 40 | 39 |
| CateZ5 | 0\|0 | NA | 0 | 20 |
| CatLeZ5 | 7\|70 | 0.024 | 50 | 55 |
| Z10Cat | 4\|80 | 0.035 | 10 | 100 |

| | Differentiated C2C12 myoblast | | | |
|---|---|---|---|---|
| Tagged CatchER | 4-cmc %\|Time-to-peak (sec) | $k_{off}$ $(s^{-1})$ | Digitonin % | Brightness % |
| CatchER | NA\|NA | NA | NA | NA |
| Cat-cyt | NA\|NA | NA | NA | NA |
| CatFKBP | 8\|15 | 0.024 | 50 | 40 |
| CatZ5 | 5\|110 | 0.014 | 40 | 44 |
| CateZ5 | 0\|0 | NA | 60 | 53 |
| CatLeZ5 | 10\|40 | 0.032 | 10 | 95 |
| Z10Cat | 6\|120 | 0.044 | 30 | 112 |

[a] Intensity reached the maximum of the detection range at the same setting as tagged CatchER.
[b] Exposure time for CatFKBP was shorter than other tagged CatchERs, 0.13 sec and 0.20 sec, respectively.

The brightness was sacrificed when any sequence was fused to CatchER. CatZ5 and CateZ5 suffered the problem of low basal intensity, which was estimated only 10% of CatchER. With a low starting intensity, it is advantageous to use the linker to improve the brightness. Compared with CateZ10 and Z10Cat, the Kozak consensus sequence did help for expression.

Accordingly, the embodiments of the calcium sensors of the disclosure were useful to measure the spatial-temporal calcium change in the cleft between the SR cisternae and transverse tubule in the skeletal muscle, a series of targeting sequences was designed to anchor the calcium indicator to SR membrane. To avoid the interference of over-expressed intrinsic SR membrane proteins, fragments of RyR1 membrane domains were selected to be candidates. Four RyR1 transmembrane fragments and FKBP were fused to CatchER. The cellular protein localization was observed by immunofluorescence staining and the result showed CatchER was successfully anchored in the ER membrane in C2C12 cells. The performance of calcium sensing evaluated by calcium imaging suggested CatchER was present in both ER lumen and cytosol.

It was further unexpectedly found that the calcium sensors designated as CatchER-T (having the amino acid sequence SEQ ID NO: 71 and variants thereof (SEQ ID NOs: 71 and 72) and having the mutations L22V, S175G, and 1218M exhibited fluorescence brightness levels advantageously greater than that emitted by the sensor CatchER (SEQ ID NO: 37) as shown in FIGS. 27 and 28. Such sensor variants have been found to provide a greater detectable fluorescent signal at 37° C., thereby allowing them to more advantageous for detecting calcium levels in cultured cells or in vivo in an animal.

One aspect of the disclosure encompasses embodiments of a polypeptide metal ion sensor comprising an engineered red fluorescent polypeptide (RFP) having a heterologous metal ion binding site comprising a plurality of negatively charged residues that in the presence of a metal ion bound thereto comprise a plurality of carboxyl oxygens orientated in a pentagonal bipyrimdal geometry, and wherein the metal ion binding site is in cooperative interaction with a chromophore region of the engineered RFP such that when the sensor does not have a metal ion bound thereto it emits a first fluorescent signal and when the sensor does have a metal ion bound thereto it emits a second fluorescent signal, wherein the first and the second fluorescent signals are distinguishably detectable, and wherein the metal ion sensor has a $k_{off}$ value for the metal ion of at least 10 s$^{-1}$.

In some embodiments of the polypeptide metal ion sensor of this aspect of the disclosure, the red fluorescent polypeptide (RFP) can have at least 95% similarity to the amino acid sequence SEQ ID NO: 40.

In some embodiments of the polypeptide metal ion sensor of this aspect of the disclosure, the engineered red fluorescent polypeptide (RFP) can have a heterologous negatively charged amino acid substitution in at least one of the amino acid positions 152, 203, 205, 207, 221, 223, and 227 of the amino acid sequence SEQ ID NO: 40.

In some embodiments of the polypeptide metal ion sensor of this aspect of the disclosure, the sensor can be conjugated to at least one targeting polypeptide motif that specifically recognizes a structural feature of a cell. In some embodiments of the polypeptide metal ion sensor of this aspect of the disclosure, the at least one targeting polypeptide motif can specifically recognize a target component of an endoplasmic reticulum or a sarcoplasmic reticulum of a cell.

In some embodiments of the polypeptide metal ion sensor of this aspect of the disclosure, the targeting polypeptide motif can have at least 90% sequence identity with the amino acid sequences selected from SEQ ID NOs: 64, 76-78, and the sequence KDEL (SEQ ID NO: 83).

In some embodiments of the polypeptide metal ion sensor of this aspect of the disclosure, the metal ion binding site can specifically bind to a metal ion selected from the group consisting of: calcium, lead, gadolinium, lanthanum, terbium, antimony, strontium, magnesium, mercury, and cadmium.

In some embodiments of the polypeptide metal ion sensor of this aspect of the disclosure, the first and second fluorescent signals can differ in at least one of intensity, wavelength, and lifetime.

In some embodiments of the polypeptide metal ion sensor of this aspect of the disclosure, the amino acid sequence of said sensor can have at least 90% similarity to a sequence selected from the group consisting of SEQ ID NOs: 41-63.

In some embodiments of the polypeptide metal ion sensor of this aspect of the disclosure, the amino acid sequence of said sensor can have at least 95% similarity to a sequence selected from the group consisting of SEQ ID NOs: 41-63.

In some embodiments of the polypeptide metal ion sensor of this aspect of the disclosure, the amino acid sequence of said sensor can have at least 95% similarity to a sequence selected from the group consisting of SEQ ID NOs: 41-45.

Another aspect of the disclosure encompasses embodiments of a recombinant nucleic acid having a nucleotide sequence having at least 95% similarity to a sequence selected from the group consisting of SEQ ID NOs: 7-36 or encoding a polypeptide metal ion sensor to an amino acid sequence selected from the group consisting of SEQ ID NOs: 41-63.

In some embodiments of the polypeptide metal ion sensor of this aspect of the disclosure, recombinant nucleic acid can be operably inserted into an expression vector nucleic acid sequence.

In some embodiments of the polypeptide metal ion sensor of this aspect of the disclosure, the recombinant nucleic acid is within a cell.

Another aspect of the disclosure encompasses embodiments of a polypeptide metal ion sensor comprising an engineered green fluorescent polypeptide (GFP) having a heterologous metal ion binding site, wherein said engineered GFP is a variant having at least 90% similarity to the amino acid sequence SEQ ID NO: 37 and having at least one amino acid substitution in sequence SEQ ID NO: 37 and selected from the group consisting of L22V, S175G, and I218M and, when having a metal ion species bound thereto, has an elevated fluorescence output compared to the polypeptide SEQ ID NO: 37 binding to the same metal ion species at 37° C.

In some embodiments of the polypeptide metal ion sensor of this aspect of the disclosure, the sensor can be conjugated to at least one targeting polypeptide motif that specifically recognizes a structural feature of a cell.

In some embodiments of the polypeptide metal ion sensor of this aspect of the disclosure, the at least one targeting polypeptide motif can specifically recognize a target component of an endoplasmic reticulum or a sarcoplasmic reticulum of a cell.

In some embodiments of the polypeptide metal ion sensor of this aspect of the disclosure, the targeting polypeptide motif can have at least 90% sequence identity with an amino acid sequence selected from the group consisting of the sequences SEQ ID NOs: 64, 76, 77, 78, and the sequence KDEL (SEQ ID NO: 83).

In some embodiments of the polypeptide metal ion sensor of this aspect of the disclosure, the metal ion binding site specifically binds to a metal ion selected from the group consisting of: calcium, lead, gadolinium, lanthanum, terbium, antimony, strontium, magnesium, mercury, and cadmium.

In some embodiments of the polypeptide metal ion sensor of this aspect of the disclosure, the amino acid sequence of said sensor can have at least 90% similarity to a sequence selected from SEQ ID NOs: 65-75 and 79-82.

In some embodiments of the polypeptide metal ion sensor of this aspect of the disclosure, the amino acid sequence of said sensor can have at least 95% similarity to a sequence selected from SEQ ID NOs: 65-75 and 79-82.

In some embodiments of the polypeptide metal ion sensor of this aspect of the disclosure, the amino acid sequence of said sensor can have sequence selected from SEQ ID NOs: 65-75 and 79-82.

Still another aspect of the disclosure encompasses embodiments of a recombinant nucleic acid can have a nucleotide sequence having at least 95% similarity to a sequence encoding a polypeptide metal ion sensor having an amino acid sequence selected from SEQ ID NOs: 65-75 and 79-82.

In some embodiments of the polypeptide metal ion sensor of this aspect of the disclosure, the recombinant nucleic acid can be operably inserted into an expression vector nucleic acid sequence.

In some embodiments of the polypeptide metal ion sensor of this aspect of the disclosure, the recombinant nucleic acid can be within a cell.

Still another aspect of the disclosure encompasses embodiments of a method of detecting metal ion in a biological sample, comprising: (i) providing a polypeptide metal ion sensor selected from: (a) an engineered red fluorescent polypeptide (RFP) having a heterologous metal ion binding site comprising a plurality of negatively charged residues that in the presence of a metal ion bound thereto comprise a plurality of carboxyl oxygens orientated in a pentagonal bipyrimdal geometry, and wherein the metal ion binding site is in cooperative interaction with a chromophore region of the engineered RFP such that when the sensor does not have a metal ion bound thereto it emits a first fluorescent signal and when the sensor does have a metal ion bound thereto it emits a second fluorescent signal, wherein the first and the second fluorescent signals are distinguishably detectable, and wherein the metal ion sensor has a $k_{off}$ value for the metal ion of at least 10 $s^{-1}$, and (b) an engineered green fluorescent polypeptide (GFP) having a heterologous metal ion binding site, wherein said engineered GFP is a variant having at least 90% similarity to the amino acid sequence SEQ ID NO: 37 and having at least one amino acid substitution in sequence SEQ ID NO: 37 and selected from the group consisting of L22V, S175G, and I218M and, when having a metal ion species bound thereto, has an elevated fluorescence output compared to the polypeptide SEQ ID NO: 37 binding to the same metal ion species at 37° C.; (ii) delivering the polypeptide metal ion sensor or an expression vector having an nucleic acid sequence encoding said metal sensor to a biological sample; (iii) detecting a first fluorescent signal emitted by said sensor; (iii) generating a physiological or cellular change in the biological sample; (iv) detecting a second fluorescent signal emitted by said sensor after step (iii); and (v) comparing the first and second fluorescent signals, wherein a ratiometric change in at least one of a wavelength or an intensity between the first and second fluorescent signals indicates a change in the rate of release or intracellular concentration of a metal ion in the sample.

In some embodiments of the polypeptide metal ion sensor of this aspect of the disclosure, the ratiometric change in the signal intensity can provide an quantitative measurement of the metal ion in the sample.

In some embodiments of the polypeptide metal ion sensor of this aspect of the disclosure, the biological sample can be a cell or tissue of an animal or human subject, or a cell or tissue isolated from an animal or human subject.

In some embodiments of the polypeptide metal ion sensor of this aspect of the disclosure, the fluorescence signal generated when a metal ion is bound to said sensor can be used to generate an image.

Still another aspect of the disclosure encompasses embodiments of a genetically modified cell comprising a recombinant nucleic acid according to the disclosure.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Design Strategy of the Red Fluorescent Calcium-Binding Protein

Figure 1A:
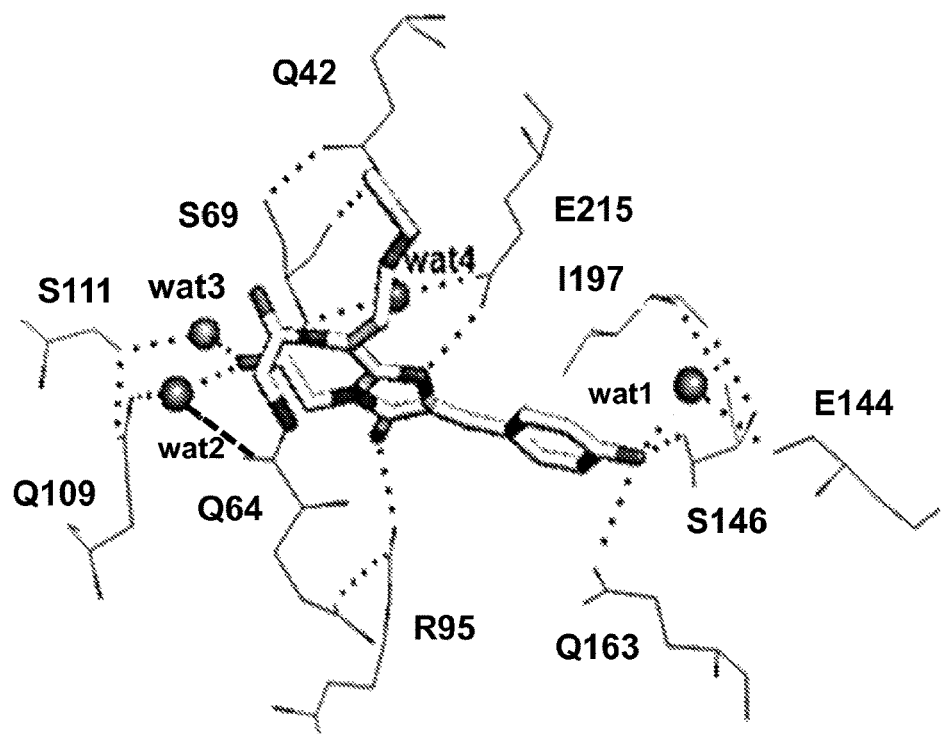
FIG. 1A illustrates a structure analysis of mCherry (SEQ ID NO: 40) showing the chromophore environment of mCherry (PDB ID 2H5Q).

FIG. 1A shows the modeled structure of a calcium-binding site formed by residues E145, D196, D198, E216 and E218 designed into the red fluorescent protein mCherry (SEQ ID NO: 40) (also denoted as RapidER (MCD1)). mCherry was chosen because it displays photo-stability, a fast chromophore maturation-rate, and low $pK_a$ (as described in Shaner et al. (2008) Nat. Methods 5: 545-551). Based on considerations for advantageous fast kinetics and calcium-induced florescence changes, this calcium-binding site was constructed based on features of calcium-binding geometry and charged residue preference obtained from statistical analysis of different classes of calcium-binding proteins, as described by Tang et al. (2011) Proc Natl Acad Sci U.S.A. 108: 16265-16270; Kirberger et al. (2008) J. Biol. Inorg. Chem. 13: 1169-1181; and Yang et al. (2003) J. Am. Chem. Soc. 125: 6165-6171.

Differing from the classic calcium-binding pocket that consists of 6-7 oxygen atoms, and which forms a bipyrimidal shape with high calcium-binding affinity and selectivity, the "half shell" with reduced coordination number was used to create a calcium-binding site on the surface of the beta barrel that allows easy entry and release of the calcium without a spatial barrier from the calcium-binding site itself. With this half shell calcium-binding site having Asp and Glu as the predominant calcium-binding ligand residues, the calcium-binding affinity was expected to be lower than is found with classic EF-hand motifs. To obtain a faster calcium association-rate than is seen with CatchER (SEQ ID NO.: 37), the negatively-charged area around the designed calcium-binding site was enlarged, based on the kinetic study of the electrostatically-driven interaction between protein and ligands, as described in Schreiber & Fersht (1996) Nat. Struct. Biol. 3: 427-431; Radic et al., (1997) J. Biol. Chem. 272: 23265-23277; and Scott et al., (2013) J. Biol. Chem. 288: 16905-16915.

To couple the calcium-binding process with the optical property change while allowing chromophore formation, the calcium-binding site was mounted in the pocket 1 according to the chromophore hydrogen-bonding network (as shown in FIG. 1A). In the pocket 1, the residue 145 was involved, flanking with E144 and S146. The main-chain oxygen of E144 forms a hydrogen bond with the chromophore tyrosyl through a bridging water molecule, and the side chain hydroxyl group of S146 has double conformer, serving directly as the hydrogen bond donor for the chromophore tyrosyl. This site was also seen at the corresponding position in CatchER (SEQ ID NO.: 37). A nucleotide sequence encoding RapidER (MCD1) (MCD1; SEQ ID NO.: 43) was codon optimized for the mammalian expression condition, the dynamic range in situ was enhanced, and designated MCD15 (E145, D196, E198, E216, E218, E220) (SEQ ID NO: 45).

Example 2

Clone Construction and PCR

Pfu DNA polymerase and the E. coli strain XL-10 Gold were from Stratagene. The KOD hot start PCR kit (Novagen) was from EMD Millipore. E. coli strain DH5α, and plasmid vector pCDNA3.1(+) were from Invitrogen. All the restriction enzymes, T4 DNA ligase, and T4 polynucleotide kinase (PNK) were from New England Biolabs. The rapid DNA ligase kit was from Roche. Primers were from Integrated DNA Technologies. DNA sequencing for all clones was carried out by GENEWIZ Inc.

mCherry or cp-mKate variants with designed binding sites were created by site-specific mutagenesis using Pfu DNA polymerase. A grafting method was used to insert a $Ca^{2+}$-binding motif or to replace a segment of DNA, for example, to substitute an original loop with a $Ca^{2+}$-binding motif. The primers were designed by limiting the melting temperature Tm of the annealed fragments in the range of 55-65° C., not longer than 45 base pairs (bps) and the GC content of less than 70%. The $T_m$ was calculated using the salt-adjusted equation:

$$Tm=81.5+16.6\times(\log_{10}([Na^+]+[K^+])+0.41\times(\% \text{ GC})-675/N$$

mCherry subcloned to pRSETb included a His-tag, a T7 phage gene 10 leader enhancing the expression of foreign DNA in *E. coli*, the enterokinase (EK) cleavage site and the mCherry gene in order from 5' to 3' end. The BamHI restriction site was inserted right after the EK cleavage site and EcoRI site was located after the stop codon. For mammalian expression, the DNA encoding the designed proteins was subcloned to pCDNA3.1(+) vector by inserting the BamHI/EcoRI double digested DNA from the pRSETb vector. The mCherry DNA was subcloned to pET28a for bacterial expression using the same double digestion method. To target the proteins in endoplasmic reticulum (ER) lumen, ER retention sequence "KDEL" (SEQ ID NO: 83) was fused to the C-terminal before the stop codon and the ER targeting sequence of calreticulin MLLSVPLLL-GLLGLAAAD (SEQ ID NO: 64) was inserted to the N-terminal after the SacI recognition site of pCDNA3.1(+) and before the BamHI site.

Example 3

Bacterial Expression and Purification

The proteins were expressed from the vector pet28a (EMD Biosciences) with a 6× His-tag using *E. coli* BL21 (DE3) in LB-kanamycin (30 µg/mL). Expression was induced at an $O.D_{600}$ of 0.6 with 0.2 mM IPTG and expression was allowed to continue for 21 hrs before the cells were harvested by centrifugation. For these studies, the temperature was controlled at both 30° C. and 37° C. after induction. The expression of EGFP and its variants was monitored with the fluorescence intensity at 510 nm with a Fluostar instrument and an excitation wavelength of 488 nm.

Protein purification was with an Amersham-Pharmacia 5 mL HiTrap chelating HP column charged with nickel. The cell pellets were resuspended in 20 mM Tris, 10 mM NaCl, 0.1% Triton X-100, pH 8.8 and sonicated. The cellular debris was removed by centrifugation and the protein was loaded onto the prepared HiTrap column connected to an Amersham-Pharmacia AktaPrime FPLC. After washing to remove contaminant proteins, the protein of interest was eluted with an imidazole gradient. Contaminant imidazole was removed by dialysis, and the protein was further purified using a HiTrap Q ion-exchange column (Amersham) with a NaCl gradient at pH 8.0. Protein purity was verified by SDS-PAGE.

Example 4

Protein Expression and Purification

The granulated LB broth miller media, yeast extract, tryptone, and agar were from EMD Millipore. The *E. coli*. strains BL21(DE3), BL21 (DE3) PlysS and Rosetta gami DE3 PlysS for protein expression were from Novagen. The polyclonal anti-DsRed antibody was from Clontech. The isotopically labeled $^{15}NH_4Cl$ was from Cambridge Isotope Laboratories Inc. The FPLC system (AKTA prime and AKTA FPLC), Ni-chelating Hi-Trap column, ion exchange Q and SP columns, tgel filtration Superdex-75 column, and the hydrophobic interaction HIC column, were from GE Healthcare.

For 1 liter media, 25 g LB broth medium was pH adjusted to 7.0 and autoclaved at 121° C., 15 MPa for 15 min. *E. coli* BL21(DE3) was screened to express wild type EGFP and its variants, wild type mCherry, and MCD1 and its derivatives, while BL21(DE3) PlysS was selected to express MCD2 and its derivatives.

mCherry and its variants were fused into pRSETb with associated ampicillin resistance; EGFP and its variants were fused to pET28b with associated kanamycin resistance. Bacteria with the desired plasmid were pre-cultured in 10 ml LB media containing 100 µg/ml ampicillin or 30 µg/ml kanamycin overnight at 37° C. The pre-culture was mixed with 1 L fresh LB media containing antibiotics and incubated at 37° C. to an $OD_{600}$ 0.5-0.6. IPTG (200 µl, 1 M stock) was then added to induce expression and the temperature was lowered to 25° C. overnight. To express proteins in Rosetta gami (DE3) PlysS, the temperature was adjusted to be 30° C. after mixing the 10 ml pre-culture to the 1 L media pre-warmed at 37° C., allowing the bacteria to adopt the temperature change before IPTG induction.

The cell pellets were harvested by centrifugation at 5,000 g at 4° C. for 10 min. Extraction buffer (20 mM Tris, 100 mM NaCl, 0.1% Triton X-100, pH 8.0) was added to resuspend the pellets. Both French Press (1240 CELL DIS) and sonication (Brenson Sonifier 450) were used to break the cells. For French Press, 20 mL extraction buffer was used for 1 L culture and 1000 psi applied. For sonication, 10 ml extraction buffer was used for 1 L culture and the instrument was set as output control at 6, duty cycle at 80% and 30 pulses for one cycle. 6 cycles were applied with 5 min between each cycle. Extracts were centrifuged at 17,000 rpm at 4° C. for 30 min, filtered using 0.45 µm membrane (Millipore), and applied to 5 ml Hi-Trap columns charged with $Ni^{2+}$.

FPLC was used to purify the protein of interest using AKTA prime. Before loading the protein, the column was charged with 0.1 M $NiSO_4$ and equilibrated with Buffer A (50 mM phosphate, 250 mM NaCl, pH 7.4) and washed by Buffer B (50 mM phosphate, 250 mM NaCl, 0.5 M imidazol, pH 7.4). Non-bound fragments were removed by 300 ml Buffer A. An additional wash step was done with 10 ml 10% Buffer B. A gradient of 10-100% Buffer B was used to elute bound protein. The purity of fractions was determined by SDS-PAGE.

Additional Mono-Q and gel filtration Superdex-75 columns were used to remove impurities. Purified fractions were collected, dialyzed in 2 L buffer of 10 mM Tris (pH 7.4) three times, and then concentrated and stored at −20° C. or used immediately.

Example 5

Cell Culture and Transfection

Both BHK-21 and HeLa cells were grown on 100 mm culture dishes or glass coverslips ($0.5-1.0\times10^6$ cells/dish) in 35 mm culture dishes in Dulbecco's Modified Eagles Medium (DMEM, Sigma Chemical Co., St. Louis, Mo.) with 44 mM $NaHCO_3$, pH 7.2 and supplemented with 10% (v/v) Fetal Bovine Serum (FBS), 100 U/ml penicillin and 0.1 mg/ml streptomycin (Pen/Strep) at 37° C. with 5% $CO_2$ in a humidified incubation chamber. The cells were seeded and grown overnight before transient transfection with $Ca^{2+}$ sensor plasmid constructs.

Plasmid DNA used for transfection was harvested from transformed *E. coli* (DH5α) using a QIAGEN Miniprep protocol (Qiagen). Each of the GFP variants was individually and transiently transfected into BHK-21 and HeLa cells with Lipofectamine-2000 (Invitrogen Life Technologies) and serum-free Opti-MEMI (Gibco Invitrogen Corporation) per the manufacturer's instructions. The plasmid DNA (2 μg) with a ratio of DNA to Lipofectamine between 1:1 and 1:3 (μg/μl) was generally used in a typical transfection. Following incubation at 37° C. for 4 hrs, the medium containing the DNA-Lipofectamine complex was removed and replaced with DMEM enriched with FBS and Pen/Strep. The cells were then grown for 1 to 3 days in a humidified chamber with 5% $CO_2$ at 30 or 37° C. before fluorescence or confocal microscope imaging.

Example 6

Variant Constructs

Amino acid sequences and nucleotide sequences encoding said amino acid sequences of embodiments of the metal ion sensors of the disclosure, and examples of the target-specific tag motifs are listed in Table 3.

TABLE 3

| SEQ ID NO. | | |
|---|---|---|
| 1 | CatchER-T with ER Tag | Nucleotide |
| 2 | Z10Cat | Nucleotide |
| 3 | CatZ5 | Nucleotide |
| 4 | CateZ5 | Nucleotide |
| 5 | CatLeZ5 | Nucleotide |
| 6 | CatFKBP | Nucleotide |
| 7 | MCD1 with ER Tag | Nucleotide |
| 8 | MCD15 with ER Tag | Nucleotide |
| 9 | MCD14 without Tag | Nucleotide |
| 10 | MCD14Y with His Tag | Nucleotide |
| 11 | MCD14YS with His Tag | Nucleotide |
| 12 | MCD16 with ER Tag | Nucleotide |
| 13 | MCD17 with ER Tag | Nucleotide |
| 14 | MCD18 with ER Tag | Nucleotide |
| 15 | MCD19 with ER Tag | Nucleotide |
| 16 | MCD110 with ER Tag | Nucleotide |
| 17 | MCD111 with His Tag | Nucleotide |
| 18 | MCD111 with ER Tag | Nucleotide |
| 19 | MCD112 with ER Tag | Nucleotide |
| 20 | MCD2 with His Tag | Nucleotide |
| 21 | MCD22 with His Tag | Nucleotide |
| 22 | MCD23 with His Tag | Nucleotide |
| 23 | MCD24 with His Tag | Nucleotide |
| 24 | MCD25 with His Tag | Nucleotide |
| 25 | MCD26 with His Tag | Nucleotide |
| 26 | mcEE with His Tag | Nucleotide |
| 27 | mcP4 with ER Tag | Nucleotide |
| 28 | mcP4 with His Tag | Nucleotide |
| 29 | mcP5 with ER Tag | Nucleotide |
| 30 | mcP5 with His Tag | Nucleotide |
| 31 | mcP6 with His Tag | Nucleotide |
| 32 | MCIN1 with His Tag | Nucleotide |
| 33 | MCIN2 with His Tag | Nucleotide |
| 34 | MCIN3 with His Tag | Nucleotide |
| 35 | MCIN3 with ER Tag | Nucleotide |
| 36 | MCIN4 with His Tag | Nucleotide |
| 37 | CatchER | Amino Acid |
| 38 | Catch-ER Tag | Amino Acid |
| 39 | CatchER-T | Amino Acid |
| 40 | MCherry | Amino Acid |
| 41 | MCD1er | Amino Acid |
| 42 | MCD15er | Amino Acid |
| 43 | MCD1 | Amino Acid |
| 44 | MCD14 | Amino Acid |
| 45 | MCD15 | Amino Acid |
| 46 | MCD2 | Amino Acid |
| 47 | MCP5 | Amino Acid |
| 48 | MCP6 | Amino Acid |
| 49 | MCD14Y | Amino Acid |
| 50 | MCD14YS | Amino Acid |
| 51 | MCD16 | Amino Acid |
| 52 | MCD17 | Amino Acid |
| 53 | MCD18 | Amino Acid |
| 54 | MCD19 | Amino Acid |
| 55 | MCD110 | Amino Acid |
| 56 | MCD111 | Amino Acid |
| 57 | MCD112 | Amino Acid |
| 58 | MCD22 | Amino Acid |
| 59 | MCD23 | Amino Acid |
| 60 | MCD24 | Amino Acid |
| 61 | MCD25 | Amino Acid |
| 62 | MCD26 | Amino Acid |
| 63 | MCP4 | Amino Acid |
| 64 | Calreticulin ER-specific tag | Amino Acid |
| 65 | CatchER-T | Nucleotide |
| 66 | CatchER-T Y39NN149E | Nucleotide |
| 67 | CatchER-T Y39N (CatchER-T1) | Nucleotide |
| 68 | CatchER-T S30R (CatchER-T2) | Nucleotide |
| 69 | CatchER-T S30R Y39N (CatchER-T') | Nucleotide |
| 70 | CatchER-JP45 | Nucleotide |
| 71 | CatchER-T Y39NN149E | Amino Acid |
| 72 | CatchER-T Y39N (CatchER-T1) | Amino Acid |
| 73 | CatchER-T S30R (CatchER-T2) | Amino Acid |
| 74 | CatchER-T S30R Y39N (CatchER-T') | Amino Acid |
| 75 | CatchER-JP45 | Amino Acid |
| 76 | eZ5 from ryanodine receptor 4551-597 (Genbank x15209) | Amino Acid |
| 77 | Z10 from ryanodine receptor 4907-943 (Genbank x15209) | Amino Acid |
| 78 | Z5 from ryanodine receptor 4551-4597 (Genbank x15209) | Amino Acid |
| 79 | Z10Cat | Amino Acid |
| 80 | CatZ5 | Amino Acid |
| 81 | CateZ5 | Amino Acid |
| 82 | CatLeZ5 | Amino Acid |

The variant DNA was verified by automated sequencing. The cDNA encoding the EGFP variants with BamH I and EcoR I restriction enzyme sites between the N and C terminals were subcloned into mammalian expression vector pcDNA3.1+ that uses the CMV promoter.

Example 7

Measurement of Fluorescent Intensity

Three 1 ml samples were collected at time points throughout the expression, and centrifuged at 14 K rpm for 3 min. The cell pellets were resuspended in 1 ml of Tris buffer at pH 7.4, and 200 μl was analyzed using a FLUOstar OPTIMA (BMG Labtech) plate reader with excitation filters of 390 and/or 460 nm and an emission filter at 510 nm.

Fluorescence Microscopy/Imaging and its Quantifications:

An inverted epifluorescence microscope (Zeiss Axiovert 200) was utilized for fluorescence intensity screening in vivo. The microscope was equipped with a xenon arc Lamp, filters for Sapphire GFP with 398 nm excitation and 510 nm emission, with standard DAPI, FITC, and Texas Red filters, and transmitted light. An Axiocam 5 CCD camera was connected to the microscope at a right angle to the stage, and Zeiss Axiovision Rel 4.3 software was used for data collection and analysis. For fluorescence intensity measurements a 40× dry objective was used with Sapphire GFP and FITC filters and exposure times from 50 to 2000 ms. The images with exposure allowing for fluorescence intensity within the dynamic range were utilized for data analysis. The fluorescence intensity measured in this time range was a linear function of the exposure time.

Both the area and mean fluorescence intensity of transfected cells (n>20 cells per image) were measured and the total mean fluorescence intensity of cells in each imaged field was obtained with the following equation $$F = \frac{\sum_{i=1}^{n} S_i F_i}{\sum_{i=1}^{n} S_i}$$

in which, F is the total mean fluorescence intensity excited at 398 nm or 480 nm of cells in each image, and n is the number of fluorescent cells. $S_i$ is the area of $i^{th}$ fluorescent cell and $F_i$ is the mea fluorescent intensity excited at 398 nm or 480 nm of $i^{th}$ fluorescent cell.

The total mea fluorescent intensity excited at 398 nm or 480 nm of the HeLa cells three days after transfection with EGFP-G1-C3 was used as a reference, and the fluorescence intensity excited at different wavelengths of the HeLa cells grown for different times with other GFP variants was expressed as a percentage of EGFP-G1-C3 fluorescence according to the following equation:

$$F' = \frac{F}{F_0} \times 100$$

in which, the F' is the relative fluorescent intensity excited at 398 nm or 480 nm of the HeLa cells, F is the total mean fluorescence intensity excited at 398 nm or 480 nm of the HeLa cells, and $F_0$ is the total mean fluorescent intensity excited at 398 nm or 480 nm of the HeLa cells.

Example 8

To measure the chromophore pKa of mCherry variants, separate samples were made at each pH to be measured and the absorbance and fluorescence of the samples examined.

The protein concentration was approximately 10 μM for each mutant. Samples were equilibrated overnight at 4° C. For UV-vis spectra, a baseline for each pH with the appropriate buffer was determined before that of the sample. The absorbance was measured from 220 nm to 700 nm. Fluorescence was measured with the excitation at 587 nm, and the emission spectra were collected from 595 to 700 nm while the excitation scan was done by fixing emission maxima at 610 nm and spectra was from 450 to 600 nm. The sample at pH 9 was measured first so the slit widths could be set for optimal intensity, and the samples were measured with decreasing pH. The pH was calculated after the spectra were acquired using the following equation.

$$Y = \frac{Y_{min} \times 10^{-pH} + Y_{max} \times 10^{-pKa}}{10^{-pH} + 10^{-pka}}$$

To calculate the extinction coefficient of the chromophore, the extinction coefficient of alkali denatured chromophore was used as a reference. The chromophore at pH 13 had the same extinction coefficient and the absorbance maxima shifted to around 455 nm as long as the chromophore is the same. 10 M NaOH was added to the sample to reach pH 13 and the spectrum was taken immediately. The following equation was used to calculate the extinction coefficient.

$$\varepsilon_{587nm} = \varepsilon_{455nm}\left(\frac{A_{587nm}}{A_{455nm}}\right)$$

where ε is the extinction coefficient; A is the absorbance. ε587 nm and $A_{587}$ nm were obtained from the mCherry and its variants at pH 7.4, while $\varepsilon_{455}$ nm and $A_{455}$ nm were from the proteins at pH 13.0.

Example 9

The quantum yield (φ) of a protein is defined as the number of photons emitted as fluorescence divided by the number of excited states produced in the excitation, i.e. the fluorescent light emitted by the protein divided by the absorbance of light of the protein. A quantum yield ratio of zero means no fluorescence and a quantum yield ratio of 1 means 100% fluorescence. The quantum yield for mCherry proteins was determined by measuring the emitted fluorescent intensities at 610 nm and the absorbance of the chromophore at 586 nm at different protein concentrations. mCherry WT was used as a control to calculate quantum yield of other variants.

By calculating both the molar extinction coefficient and quantum yield of a specific variant, the brightness of that protein, defined as a visual perception in which a source appears to emit or reflect a given amount of light, i.e. it is the perception elicited by the luminance of a visual target, was determined from the following equation.

$$\varphi_P = \varphi_r\left(\frac{F_P}{A_P}\right)/\left(\frac{F_r}{A_r}\right)$$

$$B = \varphi \times \varepsilon$$

φ is the quantum yield of the protein of interest; F/A is the slope of the fluorescence intensity as a function of the absorbance; subscript P indicates the protein of interest; r indicates the reference protein wild type mCherry.

Fluorescence emission spectra were collected between 595-750 nm when excited at 587 nm; excitation spectra were measured between 400-600 nm when emitted at 610 nm.

Example 10

Metal Binding Assays for Designed Calcium Binding Proteins

Dissociation constant ($K_d$) determination: Calcium was titrated to the protein sample to trigger an increase of fluorescence until a maximum was attained. Calcium chloride (100 mM) was used for titration. All titrations were triplicated. For CatchER, protein samples of concentration of 2 μM, 10 μM and 20 μM were tested to verify that $K_d$ is protein concentration independent. For mCherry, 5 μM and 10 μM protein was used. The $K_d$ was calculated using:

$$f = \frac{F - F_{min}}{F_{max} - F_{min}} = \frac{[P]_T + [Ca^{2+}]_T + K_d - \sqrt{([P]_T + [Ca^{2+}]_T + K_d)^2 - 4[P]_T[Ca^{2+}]_T}}{2[P]_T}$$

$$\frac{\Delta F}{F_{min}} = \frac{F - F_{min}}{F_{min}} = \frac{a \times [Ca^{2+}]}{(K_d + [Ca^{2+}])}$$

F is the fluorescence intensity read from the fluorimeter; $F_{max}$ and $F_{min}$ are the highest and lowest fluorescence intensity reading in an individual experiment; $[P]_T$ and $[Ca^{2+}]_T$ are the total concentration of protein and calcium; a is the dynamic range of fluorescence change.

Calcium Binding Using $Tb^{3+}$ as a Probe:

To further show calcium binding to mCherry-based calcium sensors, $Tb^{3+}$-FRET was applied. Titration was monitored by fluorescence spectrophotometer with excitation at 282 nm and emission in the range of 500-570 nm. To avoid precipitation due to the formation of $Tb(OH)_3$, pH was maintained at 6.5 using 20 mM PIPES. KCl (final concentration of 10 mM) was added to minimize non-specific metal binding. $Tb^{3+}$ stock was in the same buffer with a final concentration of 10 mM and 100 mM. Protein concentration was approximately 6 μM to ensure the amount of the donor for FRET, and to minimize precipitation.

Metal Selectivity:

Selectivity of a calcium sensor against other physiological metals and small molecules is an important criterion. Physiological metals such as $Mg^{2+}$, $Zn^{2+}$, $Cu^{2+}$, $Na^+$ and $K^+$, and small molecules such as ATP, GTP, ADP and GDP were added to the sensor pre-loaded with 1 mM $Ca^{2+}$. Optical properties was monitored by both UV-vis and fluorescence spectrophotometer. Concentrations of each competitor were as least 5 times as much as those of the free form in the physiological conditions.

Example 11

Equilibrium Dialysis Assay

Simulation of Equilibrium-Dialysis Assay:

Dialysis equilibration was used to verify the direct binding of calcium to the protein. The following scheme shows the typical 1:1 binding reaction:

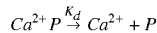

In the equilibrium state:

$$P_{free} = P_t - Ca^{2+}P$$

$$Ca^{2+}P = Ca^{2+}_{it} - Ca^{2+}_{free}$$

$$K_d = \frac{Ca^{2+}_{free} \times P_{free}}{Ca^{2+}P}$$

$$P_{free} = \frac{K_d \times P_t}{K_d + Ca^{2+}_{free}}$$

$$\frac{Ca^{2+}_{it}}{Ca^{2+}_{free}} = \frac{Ca^{2+}_{free} + P_t - \frac{K_d \times P_t}{K_d + Ca^{2+}_{free}}}{Ca^{2+}_{free}}$$

Total Metal Measurement Using ICP-OES:

Positive (α-lactalbumin) and negative (w.t.-mCherry and buffer) controls was used. To obtain the large ratio of $[Ca^{2+}]$bag to $[Ca^{2+}]$ out, high-concentrations of protein and small concentrations of calcium were used. Protein (5 mls, 30 μM in 10 mM Tris, pH 7.4) was dialyzed against 1.6 L buffer containing 15 μM $Ca^{2+}$, 10 mM Tris, pH 7.4 for 48 h at 4° C. Samples from inside and outside the dialysis bag were analyzed using ICP-OES. To obtain "well-folded" mCherry variants, the concentration was determined by UV at 587 nm, and total protein concentration was determined using extinction coefficient at 280 nm.

Calcium concentrations were monitored at the following wavelengths (nm): 396.847, 317.933, 219.779, 370.602, 643.907, 220.861 and 373.690. The $[Y^{3+}]$ was monitored at 360.074 and 371.029 nm.

Example 12

Kinetics Study of Calcium Binding

Stopped-flow kinetic measurements were performed on a Hi-Tech SF-61 stopped-flow spectrofluorimeter equipped with the mercury-Xe lamp (10 mm path length, dead time of 2 ms) with a 1:1 (v/v) ratio of the protein sensor and calcium at 20° C. Fluorescence emission changes associated with binding of calcium to the protein were determined by mixing with calcium in the range of $0.2 \times K_d$ to $5 \times K_d$ and 10 mM Tris buffer, pH 7.4 with excitation at 587 nm and a long-pass 600 nm filter.

Florescence changes associated with dissociation of calcium from the protein were measured by mixing the protein, pre-loaded with calcium at a concentration equal to $K_d$, and EGTA at a 10-fold equivalent protein concentration in the same buffer. Six duplicate measurements were carried out for each point, and the last three were fitted to obtain the observed rate, $k_{obs}$, by fitting of the stopped-flow traces according to the single-exponential function shown in the following:

$$F = F_0 + amp[1 - \exp(-k_{obs} \times t)]$$

$$F = F_\infty - amp \times \exp(-k_{obs} \times t)$$

$$amp = F_\infty - F_0$$

$$k_{obs} = k_{on} \times [Ca^{2+}] + k_{off}$$

$$K_d = \frac{k_{off}}{k_{on}}$$

$$k_{obs} \times \tau = \ln 2$$

For variant MCD15, which has a $K_d$ at 0.5 mM, the final $Ca^{2+}$ concentrations were: 100, 200, 300, 500, 900, 1300, 2500 μM. Calcium solutions were prepared as: 200, 400, 600, 1000, 1800, 2600, 5000 μM. To obtain a high S/N ratio, the fluorescence intensity was high. The lowest calcium concentration was at least 5 times higher than the protein concentration to fulfill the assumption that [$Ca^{2+}$]>>[Protein]. As a result, the final protein concentrations were 10 and 20 μM.

MCD15 purified from pET28α in *E. coli.* BL21 (DE3) was used for the kinetics study. The lowest (buffer) and highest signal (protein mixed with calcium of the highest concentration) were taken first to figure out the dynamic range, and the instrument setting adjusted to enhance the dynamic range.

F is the fluorescence intensity reading from the fluorimeter; $F_0$ is the initial fluorescence intensity, which is the lowest one as well; $F_\infty$ is the fluorescence maximum; amp is the amplitude of the fluorescence; $k_{obs}$ is the observed rate constant, which is obtained by exponential fitting the fluorescence time course; $k_{on}$ and $k_{off}$ are the on and off rate of calcium binding; τ is the observed lifetime of calcium dissociation.

Example 13

Fluorescence Lifetime Measurement

Sample Preparation:

Proteins used for the lifetime measurement were expressed by *E. coli.* BL21 (DE3) Gold and purified using the $Ni^{2+}$-charged pre-packed Hi-Trap column and the size exclusion column packed with Superdex-75 (GE Healthcare). The concentrated pure proteins in 10 mM Tris, pH 7.4, were lyophilized and dissolved by in $H_2O$ and $D_2O$ (95% D). The final pH and pD were checked and adjusted to 7.4 and 7.8, respectively.

To obtain the optimal signal in lifetime measurements, the absorbance spectra were collected and the protein concentration was adjusted to get the peak height maximum at 395 nm in the range of 0.2-0.3.

Lifetime Measurements:

The fluorimeter was equipped with lasers of 372 nm and 467 nm. Both wavelengths were applied to excite the neutral and anionic forms of the protein. The monitored emission wavelengths are 440 nm for the neutral form, 510 nm for the anionic form. The 1024 data points were collected for the set of excitation at 372 nm and emission at 440 nm in 5 ns and 20 ns separately, with steps of 0.004883 ns and 0.019531 ns, respectively. For the sets of emission at 510 nm, 1024 data points were collected in 20 ns and 50 ns, with steps of 0.019531 ns and 0.04883 ns, respectively. All measurements were carried out at 25° C.

Data Analysis:

The instrument response function was taken into account and deconvoluted using Equation 2.10. The time course of fluorescence decay was fitted using exponential equation (2.11. The artificial components were ignored, which was recognized as the negative amplitude reflecting the initial fluorescence rise prior to decay, the component with lifetime smaller than 10 ps and greater than 15 ns. The valid fitting fulfilled the conditions of chi-square in the range of 0.9-1.3 and the residuals in the range of ±4. The average lifetime was calculated by the following:

$$F_i(t) = \int I(x+t+s_i)f_i(x)dx$$

$$f_i(t) = A_{i0} + \sum A_{ij}\exp(-t/\tau_j)$$

-continued $$\tau_{ave} = \sum \left(\frac{A_i}{\sum A_i}\tau_i\right)$$

Fi(t) is the fluorescence intensity at any given time t; I is the instrumental response function; fi(x) is the real fluorescence of the chromophore/protein at the time x; A is the amplitude of the background fluorescence; $\tau_i$ is the lifetime of the component i.

Example 14

Calcium Response Monitored by Designed Calcium Binding Proteins In Situ

Materials and Supplies:

Dulbecco's modified Eagle's medium (DMEM) and Hank's balanced salt solution (HBSS) were from Sigma Chemical Co. Fetal bovine serum (FBS), Opti-MEM reduced serum media, and lipofectamine 2000 were from Invitrogen. FuGENE HD Transfection reagent was from Roche. The SERCA pump inhibitor Cyclopiazonic acid (CPA) and Thapsigargin, the cell membrane permeabilizer digitonin, the IP3R agonist Histamine and IP3, the Ryanodine receptor agonists 4-Chloro-m-cresol (4-cmc) and caffeine, the calcium ionophore ionomycin, as well as the solvent DMSO, were from Sigma.

Cell Culture and DNA Transfection:

HEK293 and C2C12 cells were grown on 100 mm culture dishes or glass cover slips (0.5-1.0×10⁶ cells/dish) in 35 mm culture dishes in DMEM with high glucose for HEK293 and C2C12 with 44 mM $NaHCO_3$ (pH 7.2) and supplemented with 10% (v/v) fetal bovine serum (FBS), 100 units/mL penicillin, and 0.1 mg/ml streptomycin (Pen/Strep) at 37° C. with 5% $CO_2$ in a humidified incubation chamber. The cells were seeded and grown overnight before transient transfection with $Ca^{2+}$-sensor plasmid constructs.

Plasmid DNA used for transfection was harvested from transformed *E. coli* (DH5α) using a QIAGEN Miniprep protocol (Qiagen). Each of the mCherry variants was individually and transiently transfected into cells with FuGENE HD Transfection reagent or lipofectamine 2000 and serum-free Opti-MEM per the manufacturer's instructions. The plasmid DNA (1.5 μg) with a ratio of DNA to transfection reagent at 1:2-1:3 (μg/μl) was generally used in a typical transfection. The cells were then grown for 2 days in a humidified chamber with 5% $CO_2$ at 37° C. before fluorescence microscope imaging. For C2C12 cell line, incubation at 30° C. was favored.

Example 15

Cell Imaging of Calcium Calibration and Response

A calibration protocol (Hofer A M (2006) *Methods Mol. Biol.* 312: 229-247) was used for the mCherry-based calcium sensors targeted to ER lumen. Mag-Fura-2 AM that accumulates in ER, was used for comparison. The drugs, 4-Chloro-m-cresol (4cmc), Cyclopiazonic acid (CPA), Inositol-1,4,5-triphosphate (IP3), Thapsigargin and Adenosine-5'-triphosphate (ATP), were used to activate the calcium channels such as ryanodine receptor (RyR) and inositol trisphosphate receptor (IP3R) to release ER calcium or to inhibit sarcoplasmic reticulum $Ca^{2+}$-ATPase (SERCA) pump to reload calcium into ER.

TABLE 4

Agonists and antagonists used for induce calcium change

| Agents | Stock Conc. | Buffer | Target | Anticipated effect $[Ca^{2+}]_{ER}$ | $[Ca^{2+}]_{cyt}$ |
|---|---|---|---|---|---|
| ATP | 100 mM | Sterile H$_2$O | IP$_3$R | Decrease | Increase |
| Caffeine | 40 mM | Sterile H$_2$O | RyR | Decrease | Increase |
| Histamine | 50 mM | Sterile H$_2$O | IP$_3$R | Decrease | Increase |
| Thapsigargin | 1 mM | DMSO | SERCA | Decrease | Increase |
| Ionomycin | 5 mM | DMSO | IP$_3$R and Membrane | Decrease and cell death | Increase |
| Digitonin | 25 mg/ml | Sterile H$_2$O | Membrane | Cell death | |
| 4cmc | 20 mM | Sterile H$_2$O | RyR | Decrease | Increase |
| CPA | 50 mM | DMSO | SERCA | Decrease | Increase |
| IP$_3$ | 10 mM | DMSO | IP$_3$R | Decrease | Increase |

Standard Ringer's buffer and supplemented with 10 mM glucose before use. The intracellular buffer was prepared as 125 mM KCl, 25 mM NaCl, 10 mM HEPES, 0.2 mM MgCl$_2$, 200 µM CaCl$_2$, 500 µM EGTA to give a final free [Ca$^{2+}$] of approximately 100 nM and the addition of 0.5 mM Na$_2$ATP before use; pH was adjusted to be 7.25. KCl solution was prepared as 125 mM KCl, 25 mM NaCl, 10 mM HEPES, 0.2 mM MgCl$_2$, pH 7.25, which was used for calibration together with the calcium stock (1 M CaCl$_2$) and Nitrilotriacetic acid (NTA) stock (1 M).

To calibrate calcium indicators targeted in the ER, the membrane is necessary to be permeabilized by digitonin at a final concentration of 25 µg/mL in the intracellular buffer. Calcium buffers were prepared to obtain the low calcium concentration in micromolar level.

Example 16

Confocal Microscope Imaging

BHK-21 and HeLa cells were transferred from DMEM to Hank's Balanced Salt Solution without divalent cations (HBSS(−), Sigma Chemical Co., St. Louis, Mo.) media with 10 mM HEPES, 5 mM NaHCO$_3$, 1 mM EGTA, and pH 7.2 for live imaging experiments on a LSM 510 laser confocal microscope (Carl Zeiss Inc., Thornwood, N.Y.) using a 100× oil-immersion objective (Zeiss, Fluar, 1.30 n.a.). Prior to imaging, cells and buffers were brought to ambient temperature and allowed to equilibrate to room air. The localization of EGFP-based Ca$^{2+}$ sensors was visualized by excitation of EGFP with the 488 nm line of an Argon laser and the narrowest bandpass filter (505-530 nm) was employed for emission. DsRed2-ER was excited with the 543 nm line of a He—Ne laser, and emission was detected through a long-pass filter (emission above 560 nm). Zeiss LSM 510 software (Carl Zeiss, Inc.) was used to control the image acquisition parameters. All images were acquired at high resolution (1024×1024).

Example 17

Fluorescence Microscope Imaging and its Quantification

BHK-21 cells were imaged 1-3 days following transfection with GFP variants. A Nikon TE200 microscope running Metafluor software (Universal Imaging) with dual excitation capability was used for the cell imaging experiments. The ratio of fluorescence emission of EGFP-based Ca$^{2+}$ sensors (measured at 510 nm) in response to excitation wavelengths of 385 nm and 480 nm was measured to monitor changes in [Ca$^{2+}$]$_{ER}$ in time series experiments. The [Ca$^{2+}$]$_{ER}$ in BHK-21 cells was quantified according to the following equation:

$$[Ca^{2+}] = K_d \times \left(\frac{R - R_{min}}{R_{max} - R}\right)^{\frac{1}{n}}$$

in which R is the fluorescent emission ratio (measured at 510 nm) for 385 nm/480 nm excitation at the initial state, $R_{min}$ is the minimum of the emission ratio determined at the Ca$^{2+}$-free state, $R_{max}$ is the maximum of the emission ratio at the Ca$^{2+}$-saturated state, $K_d$ is the apparent dissociation constant (mM) and n is the Hill coefficient (n=1). Ca$^{2+}$-free and Ca$^{2+}$-saturated states were obtained on cells treated with 5 µM ionomycin and exposed to 1.0 mM EGTA and 1.0 mM Ca$^{2+}$, respectively.

Example 18

Kinetics Study of Calcium-Binding to RapidER (MCD1)

The amino acid sequences designated RapidER (MCD1) (SEQ ID NO: 43) and MCD15 (SEQ ID NO: 45) were expressed in bacteria and purified as described in Shu et al., (2006) *Biochemistry* 45: 9639-9647, incorporated herein by reference in its entirety.

Figure 1B:
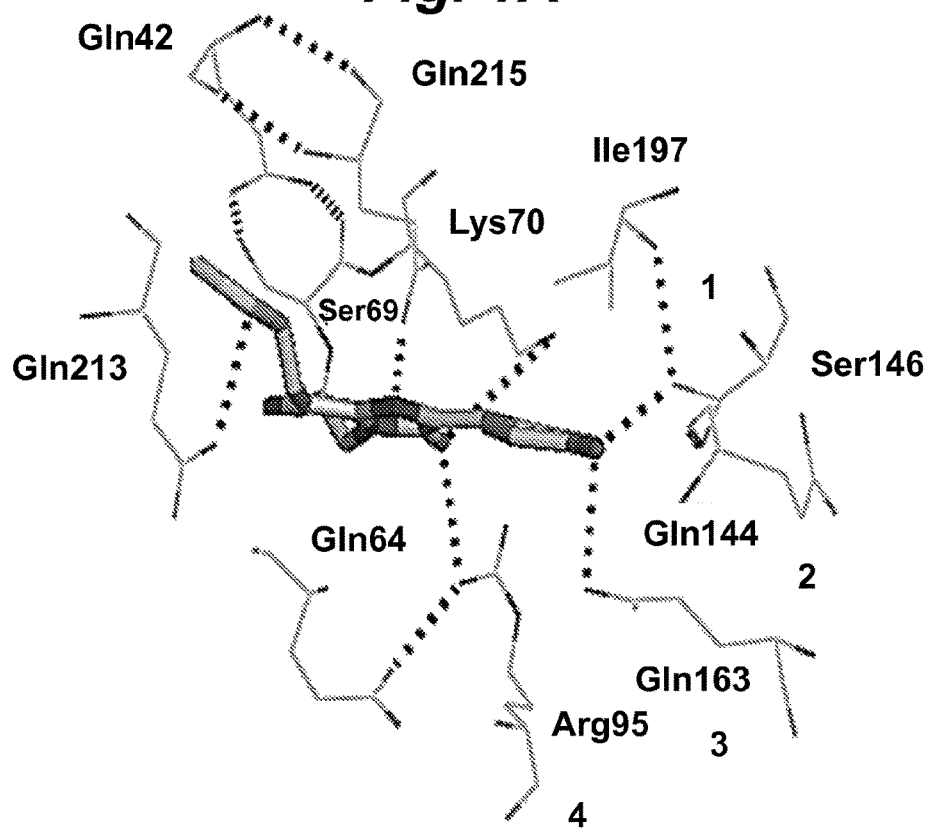
FIG. 1C illustrates the electrostatic density map from the wild type mCherry (SEQ ID NO: 40) to the mutant RapidER (MCD1) (SEQ ID NO: 43). The electrostatic potential was calculated by Delphi using Amber force field ff99SB and visualized by PyMol.
FIG. 1D illustrates the $Ca^{2+}$-coordinating oxygen (top) and carbon-alpha (bottom) geometry in RapidER (MCD1) (SEQ ID NO: 43) model. The $Ca^{2+}$ was docked by AUTODOCK-VINA® and MUG®.
FIG. 1E illustrates a kinetics analysis of association of $Ca^{2+}$ with RapidER (MCD1) (SEQ ID NO: 43). (Top) The amplitude of the fluorescence increase is a function of calcium concentration. Inset shows the stopped-flow traces of fluorescence increase upon rapid mixing of RapidER (MCD1) (SEQ ID NO: 43) at a final concentration of 10 μM at different calcium concentrations; (Bottom) The stopped-flow traces of the fluorescence change upon (a) mixing 20 μM RapidER (MCD1) (SEQ ID NO: 43) with 0.6 mM $Ca^{2+}$, (b) mixing of 20 μM MCD1 (SEQ ID NO: 43) preloaded with 0.6 mM $Ca^{2+}$ with 10 mM EGTA and (c) mixing of 20 μM RapidER (MCD1) (SEQ ID NO: 43) (SEQ ID NO: 43) with buffer.

FIG. 1B (Panels a and b) shows the absorbance and florescence spectra of RapidER (MCD1) (SEQ ID NO: 43) in the absence and presence of calcium, which was similar to the spectral property of MCD15 (SEQ ID NO: 45). A Ca$^{2+}$-induced fluorescence increase was seen and the dissociation constant $K_d$ was fitted by Eq. 1 using the calcium titration data (FIG. 5) was 0.10±0.03 mM.

Figure 2B:
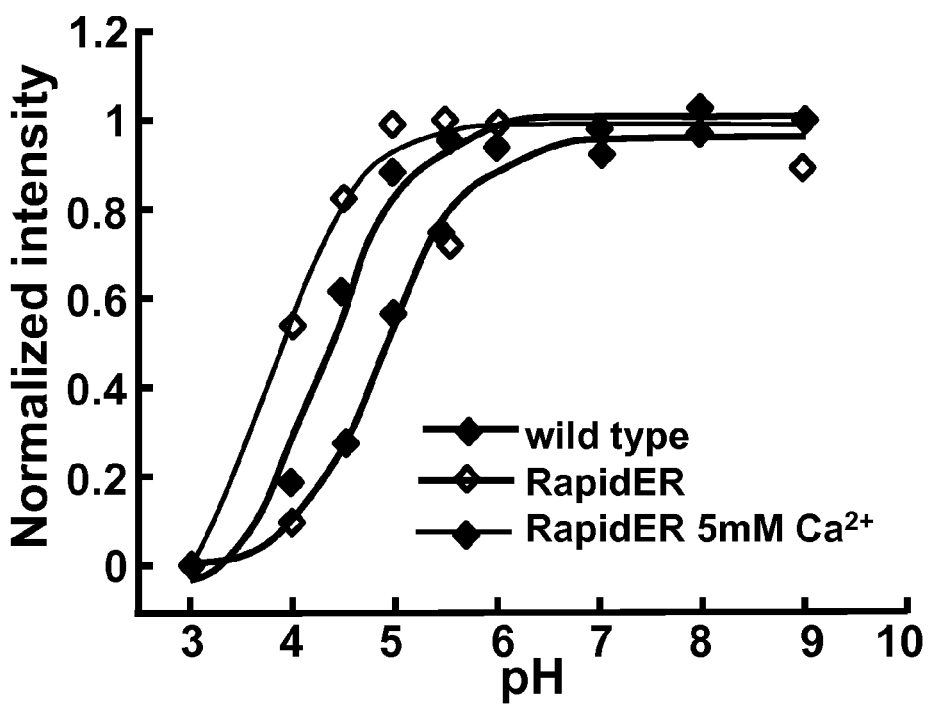
FIG. 2B illustrates a structure analysis of mCherry (SEQ ID NO: 40) showing the chromophore environment of mCherry (PDB ID 2H5Q).
Figure 3A:
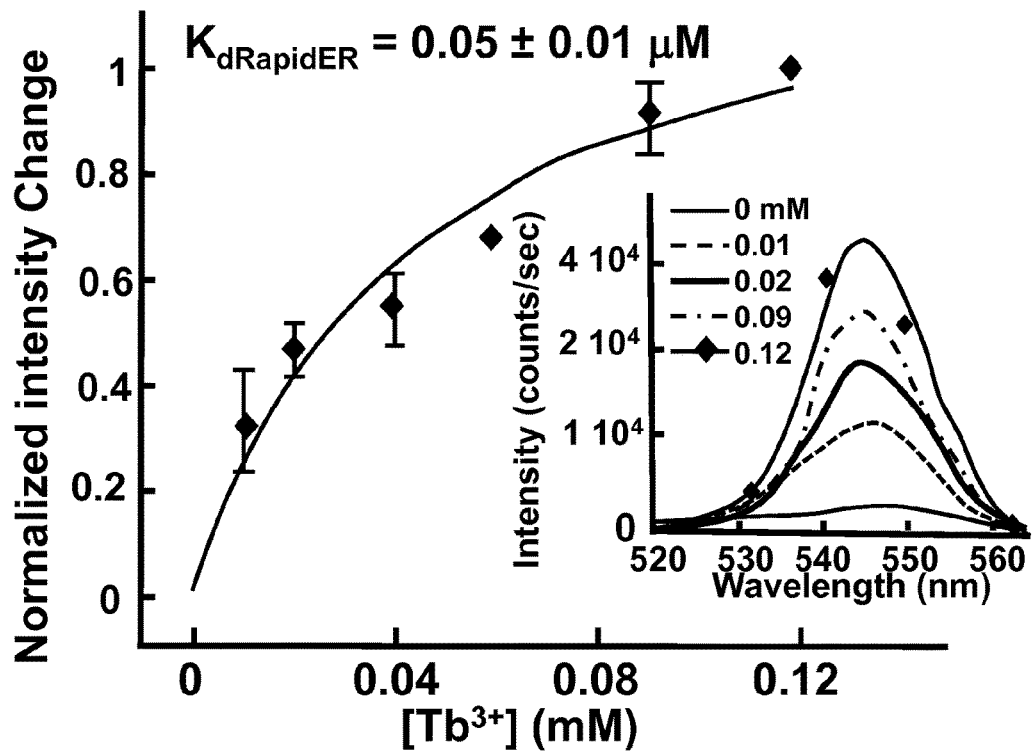
FIG. 3A illustrates the use of $Tb^{3+}$ as a probe to determine calcium-binding to RapidER (MCD1) (SEQ ID NO: 43). The dissociation constant was 0.05±0.01 mM. The inset shows the fluorescence spectra at different concentrations of $Tb^{3+}$, which were recorded from 500 to 570 nm by fluorescence spectrophotometer with excitation at 282 nm.
Figure 3B:
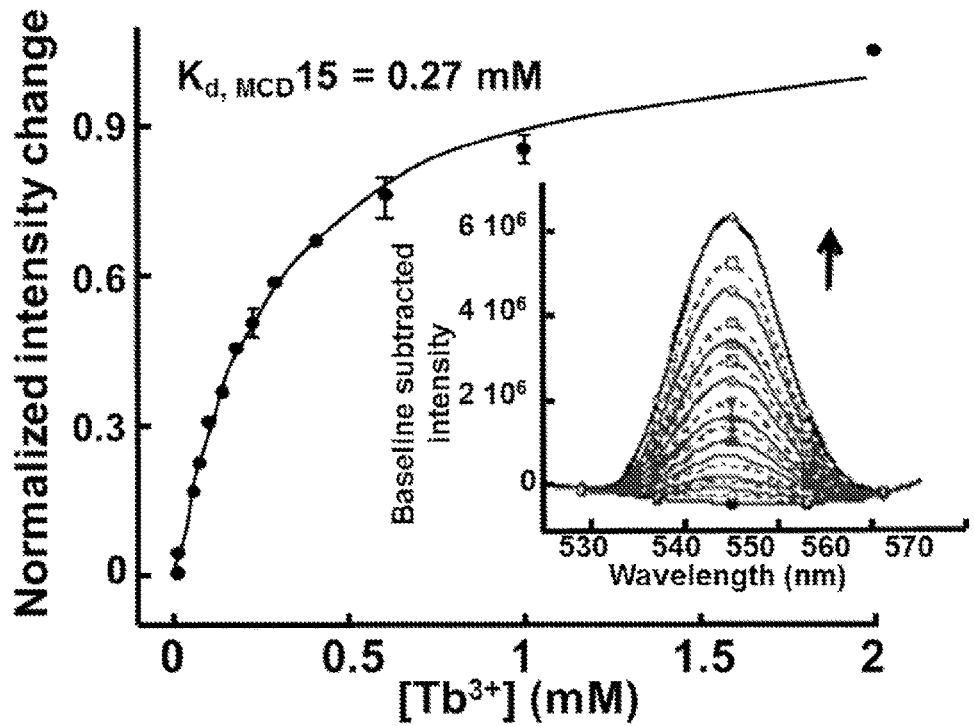
FIG. 3B illustrates using the $Tb^{3+}$-RapidER (MCD1) (SEQ ID NO: 43) chromophore FRET to obtain the distance between $Ca^{2+}$ and the chromophore. The fluorescence lifetime was recorded at 265 nm and emission at 545 nm. The double exponential and triple exponential equations were used to fit the lifetime of Rapidggg and Rapid, respectively.

The calcium-binding kinetics were studied by the stopped-flow fluorometer (FIG. 3). Thus, mixing RapidER (MCD1) (SEQ ID NO: 43) with different concentrations of calcium resulted in the immediate rise of the fluorescence. However, the binding process was totally lost in the dead time. Accordingly, there was less likelihood to fit k$_{obs}$ at even the lowest calcium concentration applied. Similarly, the off-rate was too fast to be captured. As shown in FIG. 2B, the overlay of stopped-flow traces indicated that the fluorescence signal fell back to the basal level upon EGTA chelating Ca$^{2+}$. Considering that 99% fluorescence was lost in the 2 ms dead time of the measuring instrument, k$_{off}$ could be estimated to be at least 1.9×10$^3$ s$^{-1}$ based on the assumption that 4× half lifetime was finished in the instrument dead time. Assuming calcium-binding to RapidER (MCD1) (SEQ ID NO: 43) followed the simple 1:1 binding mode, k$_{on}$ could be estimated as at least 2.7×10$^7$ M$^{-1}$ s$^{-1}$.

Figure 5B:
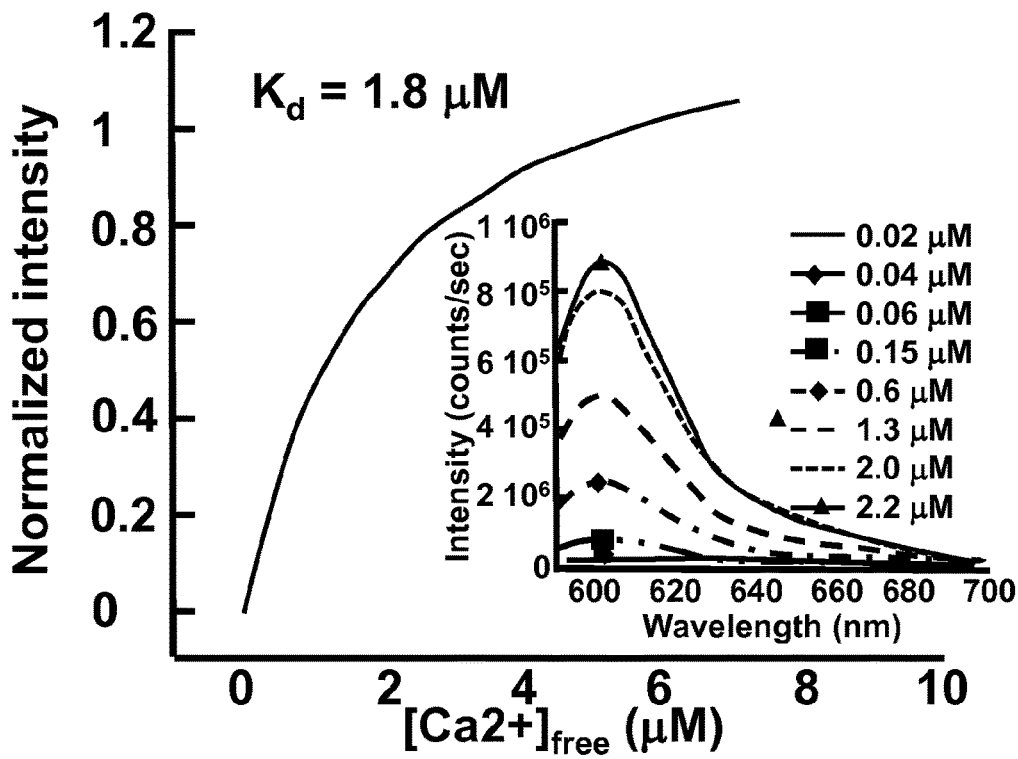
FIG. 5B illustrates the calcium titration for x-Rhod-5F in 10 mM MOPS, 100 mM KCl, pH 7.2. The calcium concentrations were obtained by mixing 10 mM $Ca^{2+}$-EGTA and 10 mM EGTA buffer.
Figure 5C:
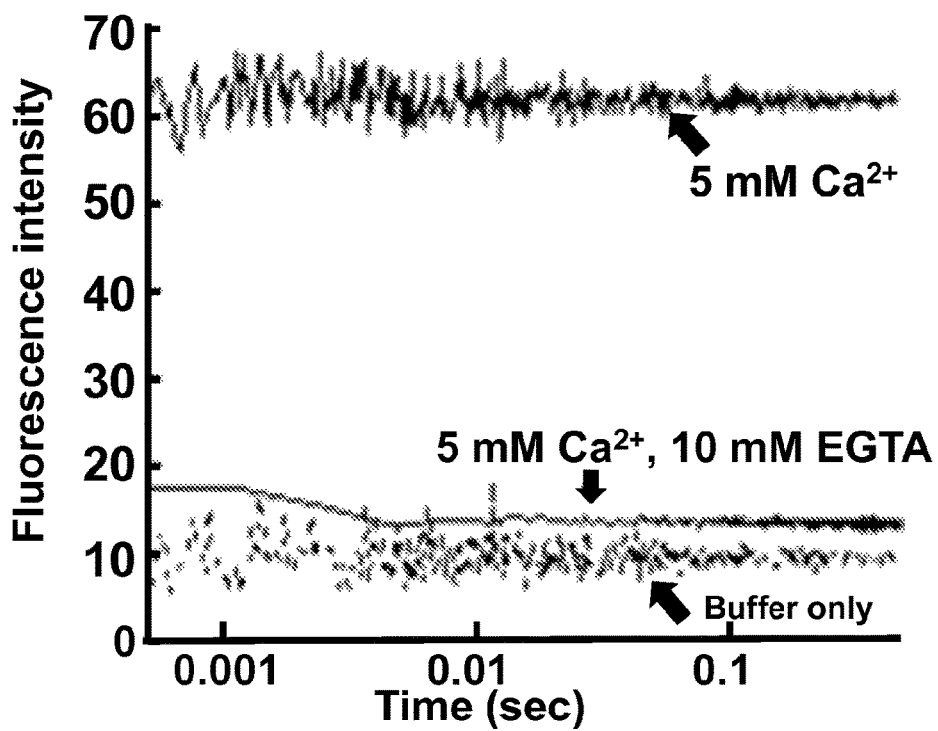
FIG. 5C illustrates the calcium dissociation-rate studied by stopped-flow fluorescence spectroscopy. By chelating calcium with EGTA, the fluorescence of x-Rhod-5F decreased and only the plateau was observed.

The dissociation constant was fitted using the plateau of the amplitudes of the fluorescence increase (0.07±0.01 mM), which was consistent with the $K_d$ value independently determined by the calcium titration monitored by a spectrofluorometer with the error in an acceptable range. The similar fast calcium dissociation-rate was observed for x-Rhod-5F (Invitrogen). The $k_{off}$ was determined by mixing x-Rhod-5F pre-loaded with calcium or with EGTA. The process of calcium dissociation from the dye was also lost in the dead time and only the plateau was observed, as shown in FIG. 5.

Compared to the earlier CatchER protein (SEQ ID NO: 37), RapidER (MCD1) (SEQ ID NO: 43) showed stronger calcium-binding affinity and faster kinetics. The calculated electrostatic binding energy change of RapidER (MCD1) (SEQ ID NO: 43) was greater than that of CatchER (SEQ ID NO: 37), as shown in Table 5, in agreement with the $K_d$ obtained by stopped-flow fluorescence spectroscopy.

TABLE 5

The electrostatic binding energy calculation

| Proteins | $\Delta G_{elec\_binding}$ (kT) | Negatively charged SAA (Å$^2$) |
|---|---|---|
| RapidER (MCD1) (SEQ ID NO: 43) | −73.03 | 655 |
| CatchER (SEQ ID NO: 37) | −59.48 | 589 |

The calculated negatively-charged solvent accessible surface area (SASA) in the designed calcium-binding site was also larger in RapidER (MCD1) (SEQ ID NO: 43) than in CatchER (SEQ ID NO: 37). One more negatively charged residue Asp200 in RapidER (MCD1) (SEQ ID NO: 43) may help to orient the $Ca^{2+}$ ion to the binding site and thus increase the on-rate. The off-rate was also increased as a consequence of both equilibrium dissociation constant $K_d$ and the association-rate $k_{on}$.

Example 19

Determination of Biophysical Properties of the Designed RapidER (MCD1) (SEQ ID NO 43)

The biophysical properties of mCherry (SEQ ID NO: 40), RapidER (MCD1) (SEQ ID NO: 43), and MCD15 (SEQ ID NO: 45) are summarized in Table 6.

The pH profile, as shown in FIG. 2B, panel c, indicated that the fluorescence change was calcium independent at pH values greater than about 6.0. When the pH was lower than about 6.0, calcium-binding affected the equilibrium of the chromophore protonation/deprotonation and led to a higher $pK_a$, opposite to the calcium effect on CatchER. Introduction of four negatively-charged residues decreased the quantum yield, which was rescued in the presence of the calcium ion. In agreement with the optical spectra, the extinction coefficient was not calcium dependent. Thus, without calcium, the resulting brightness was lower than the wild type, and calcium-binding recovered it back to the original level.

Example 20

Metal Binding Assays for Verification of $Ca^{2+}$-RapidER (MCD1) Interaction

Figure 6A:
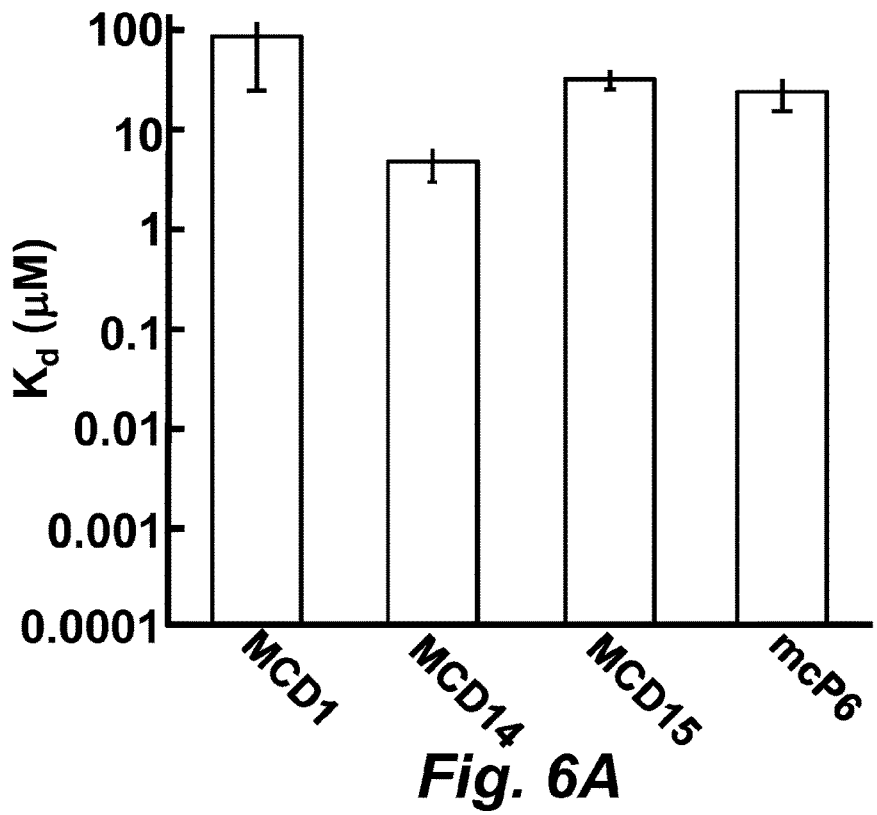
FIGS. 6A and 6B illustrate an equilibrium-dialysis assay for calcium dissociation constant determination.
Figure 6B:
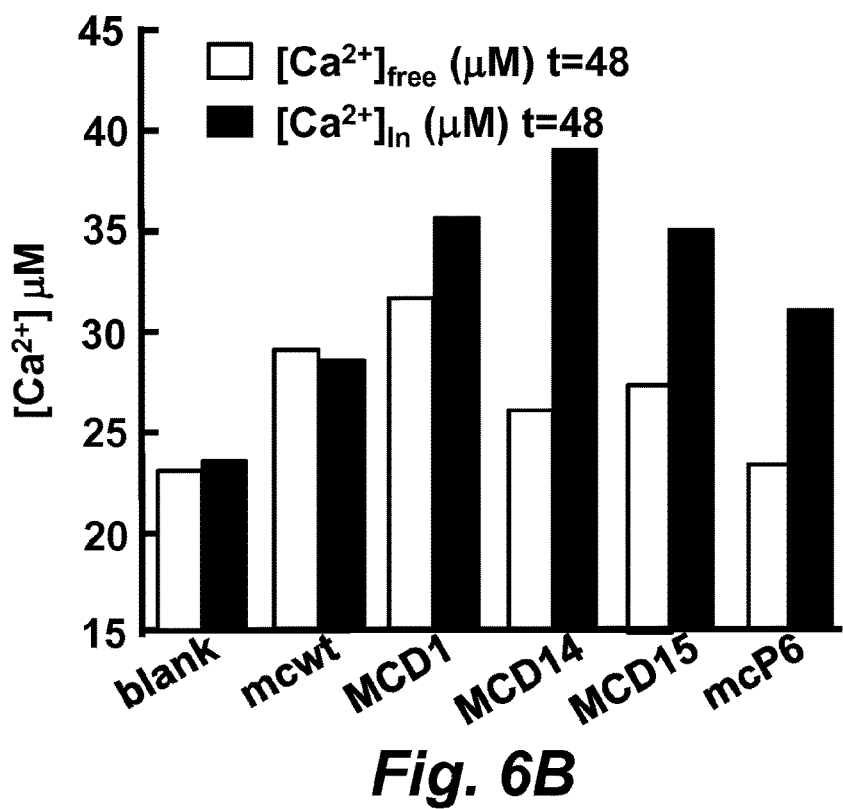

Fluorescence titration showed a calcium-dependent fluorescence intensity increase with RapidER (MCD1). To further verify calcium-binding to RapidER (MCD1) (SEQ ID NO: 43), the equilibrium-dialysis equilibrium assay was used. At equilibrium, the calcium concentration of the buffer and the protein was determined by ICP-OES. The α-lactalbumin and the wild type mCherry (SEQ ID NO: 40) served as the positive and negative controls, respectively, as shown in (FIG. 6).

A sample with only Tris buffer was used to correct the influence of the non-specific sticking of calcium ion to the dialysis bag. The corrected RapidER (MCD1) (SEQ ID NO: 43) $K_d$ obtained from the dialysis-equilibrium assay was 0.07±0.04 mM, which was consistent with that measured by the fluorescence. The dissociation constant of MCD15 (SEQ ID 45) was insignificantly lower than that of RapidER (MCD1) (SEQ ID NO: 43). However, the $K_d$ fitted using the calcium titration monitored by fluorescence was approximately 10-fold higher, suggesting that the fluorescence of MCD15 was less sensitive to calcium-binding than RapidER (MCD1) (SEQ ID NO: 43).

While not wishing to be bound by any one theory, the binding site in MCD15 (SEQ ID NO: 45) with six negative charges may shift the calcium-binding center away from the chromophore tyrosyl which plays an important role in the chromophore hydrogen bonding network. The local conformational change close to the chromophore sensitive region requires a larger amount of $Ca^{2+}$ accumulation and the threshold was increased. Therefore, the apparent dissociation constant determined by the calcium titration only

TABLE 6

Biophysical properties of designed calcium-binding proteins

| | pKa | | Quantum Yield | | Lifetime (ns) | | Extinction Coeff. | Brightness | |
|---|---|---|---|---|---|---|---|---|---|
| | Apo | Holo | Apo | Holo | Apo | Holo | (mM$^{-1}$ cm$^{-1}$) | Apo | Holo |
| mCherry (SEQ ID NO: 40) | 4.3 ± 0.1 | | 0.22 | | 1.46$^a$ | | 72 | 0.16 | |
| MCD1 (SEQ ID NO: 43) | 3.6 ± 0.1 | 4.9 ± 0.1 | 0.17 | 0.24 | 1.52 | 1.61 | 64 | 0.11 | 0.15 |
| MCD14 (SEQ ID NO: 44) | | | 0.20 | 0.22 | | | | 0.13 | 0.15 |
| MCD15 (SEQ ID NO: 45) | 4.4 ± 0.1 | 4.6 ± 0.1 | 0.20 | 0.22 | 1.44 | 1.47 | 65 | 0.13 | 0.14 |

$^a$Reported by Seefeldt et al. (2008) *J. Biophotonics* 1: 74-82 reflected the calcium-binding effective for the fluorescence change but not the calcium-binding capability of the protein itself.

The calcium-induced local conformational change was also observed in the tryptophan-$Tb^{3+}$ fluorescence resonance energy transfer (FRET). The lanthanide ions share similar binding properties with calcium (Pidcock & Moore (2001) *J. Biol. Inorg. Chem.* 6: 479-489; Brittain et al., (1976) *J. Am. Chem. Soc.* 98: 8255-8260). Accordingly, the $Tb^{3+}$ ion can mimic $Ca^{2+}$ for the binding assay.

There are three tryptophan residues in mCherry (SEQ ID NO: 40). W143 is the one close to the designed calcium-binding site of RapidER (MCD1) (SEQ ID NO: 43), which is likely the major source of the energy donor. $Tb^{3+}$ served as the energy acceptor when tryptophan was excited at 282 nm. Thus, the readout of Trp-$Tb^{3+}$ FRET can be used to verify the binding of calcium.

Figure 2A:
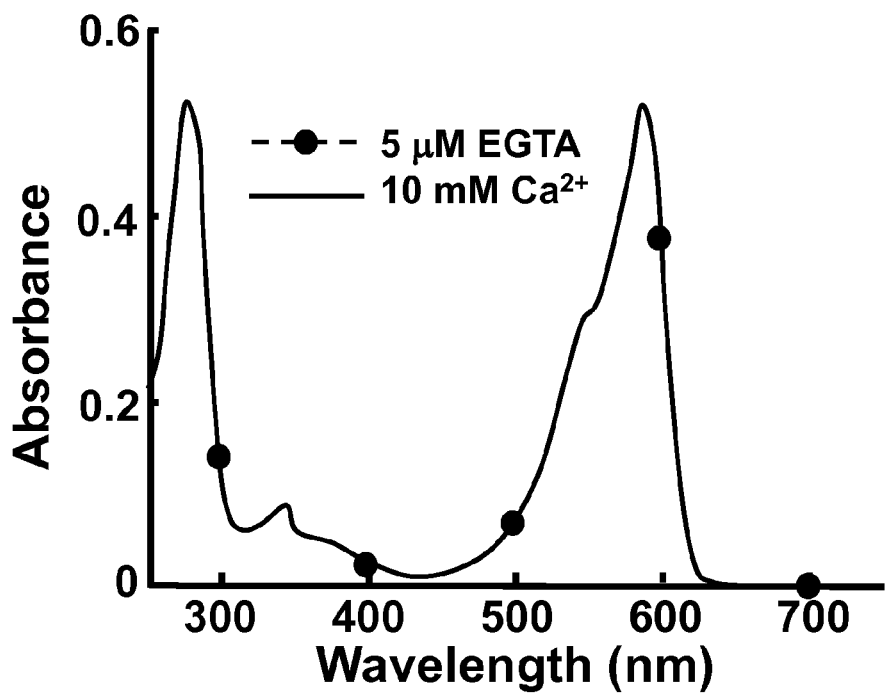
FIG. 2A illustrates the spectral property of RapidER (MCD1) (SEQ ID NO: 43) with the UV/optical spectrum in the absence and presence of calcium.

The fluorescence intensity increase at 545 nm was observed upon the addition of $Tb^{3+}$ (<150 μM) to RapidER (MCD1) (SEQ ID NO: 43), as shown in FIG. 2A, suggesting that the energy transfer from the tryptophan residue to $Tb^{3+}$ occurred. When $Tb^{3+}$ concentration was greater than 150 μM, precipitates were seen with wild type mCherry and RapidER (MCD1). MCD15 was able to tolerate $Tb^{3+}$ to about 2 mM. The binding affinity of $Tb^{3+}$ was stronger than that of $Ca^{2+}$ due to the larger charge to ionic radius ratio. $Tb^{3+}$-FRET indicated that $Tb^{3+}$ can access to the designed calcium-binding site, which induces the energy transfer from a tryptophan nearby to $Tb^{3+}$.

TABLE 7

Dissociation constants of mCherry variants

| Mutants | $Ca^{2+}$ (mM) | | | $Tb^{3+}$ (mM) |
| --- | --- | --- | --- | --- |
| | Titration | Stopped-flow | Equilibrium-dialysis | |
| RapidER (MCD1) (SEQ ID NO: 43) | 0.10 ± 0.03 | 0.07 ± 0.01 | 0.07 ± 0.04 | 0.04 ± 0.01 |
| MCD14 (SEQ ID NO: 44) | 0.08 ± 0.01 | NA | 0.004 ± 0.001 | NA |
| MCD15 (SEQ ID NO: 45) | 0.47 ± 0.12 | NA | 0.03 ± 0.01 | 0.27 ± 0.01 |

<sup>a</sup>The proteins were excited at 587 nm and the maximum fluorescence emission intensity at 610 nm was used for calculation.
<sup>b</sup>The excitation/emission was set as 587/610 nm, respectively. The average fluorescence intensity at the plateau was used for calculation.
<sup>c</sup>The average value was obtained from five Ca2+ signature emission wavelengths: 317.933, 370.602, 373.690, 396.847, 643.907 nm.
<sup>d</sup>The experiment was carried out at 10 mM PIPES, pH 6.5, 10 mM KCl. The excitation was at 350 nm and the emission was collected from 420-600 nm. The $Tb^{3+}$ fluorescence was used to determine the distance between the chromophore and bound $Tb^{3+}$. Here, the FRET pair was composed of $Tb^{3+}$ and RapidER (MCD1) (SEQ ID NO: 43) due to the overlap between the emission spectrum of $Tb^{3+}$ and excitation spectrum of RapidER (MCD1) (SEQ ID NO: 43) at 545 nm. The distance between the FRET donor and acceptor is related to the lifetime ratio of the donor in the absence and presence of the acceptor. RapidER (MCD1)ggg, wherein the chromophore MYG was mutated to GGG, was folded the same as RapidER (MCD1) (SEQ ID NO: 43) but was not fluorescent. The lifetime of $Tb^{3+}$-RapidER (MCD1)ggg is that of FRET donor in the absence of the acceptor.

Figure 2C:
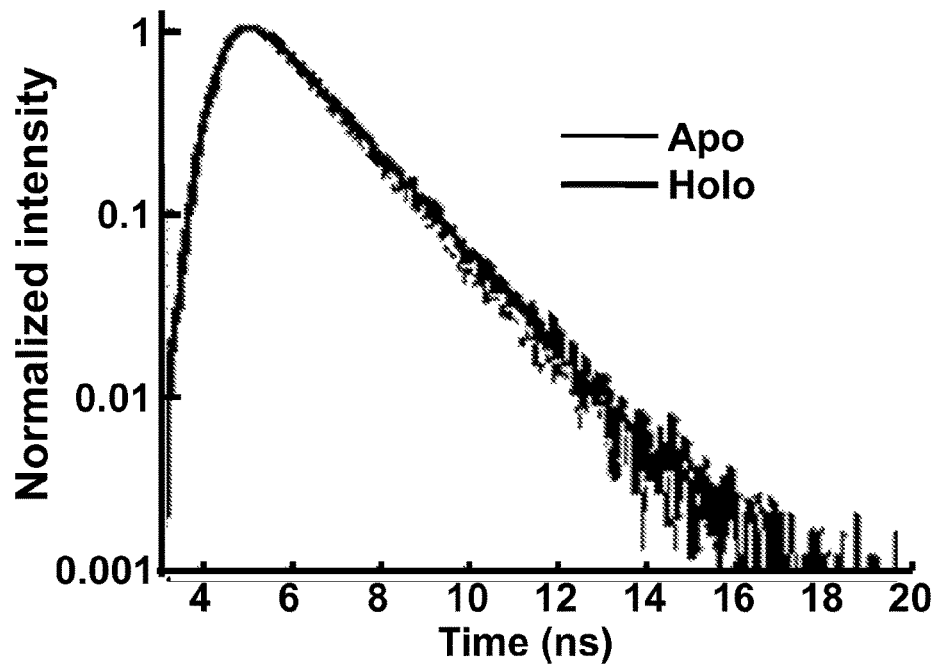
FIG. 2C illustrates the measurement of RapidER (MCD1) (SEQ ID NO: 43) fluorescence lifetime. The apo form was in the presence of 5 μM EGTA and the holo form was in the presence of 5 mM $Ca^{2+}$. 10 μM protein sample was prepared in 10 mM Tris, pH 7.4.
Figure 2D:
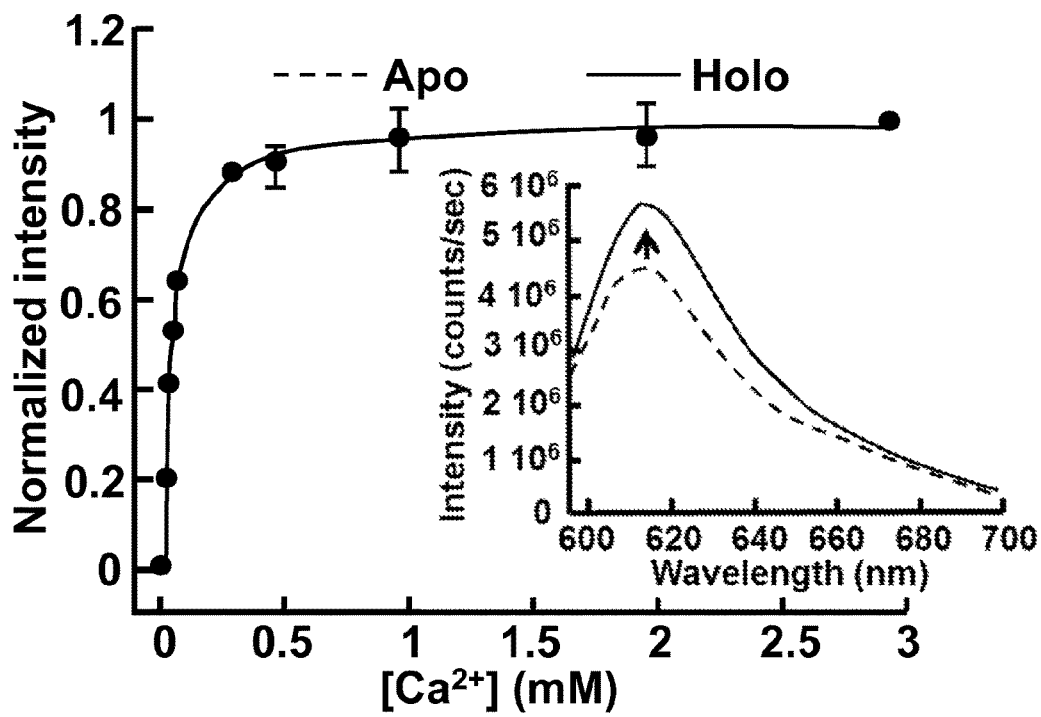
FIG. 2D illustrates calcium titration monitored by fluorescence. The inset shows the emission spectrum (excited at 587 nm) in the presence of 5 μM EGTA and 5 mM $Ca^{2+}$. Fluorescence in all measurement was excited at 587 nm and emission was monitored at 610 nm.

FIG. 2B illustrates that the fluorescence decay of $Tb^{3+}$ was faster when binding to RapidER (MCD1) (SEQ ID NO: 43). The FRET efficiency was 94% and the ratio $r/R_0$ was 0.6. The critical distance was determined by the protocol by Hink et al., (2003) *J. Fluoresc.* 13: 185-188. The calculated critical distance and the distance between the chromophore and $Tb^{3+}$ ion were 29 Å and 17 Å, respectively. The measured distance in the RapidER (MCD1) (SEQ ID NO: 43) model from $Ca^{2+}$ to the chromophore was in the range of 11-17 Å, in agreement with the calculated one and the crystal structure of $Ca^{2+}$-CatchER, confirming the location of calcium ion site in mCherry (SEQ ID NO: 43), as shown in FIG. 2C.

Example 21

Evaluation of the Red Fluorescent Calcium-Binding Protein In Situ

To evaluate the designed calcium-binding proteins in high calcium environment in situ, the proteins were fused with the calreticulin endoplasmic reticulum (ER) tag at the N-terminal and the ER-retention peptide sequence KDEL (SEQ ID NO: 83) at the C-terminal.

An agonist of the ryanodine receptor (4-cmc), an antagonist of the SERCA pump (CPA) and the calcium ionophore ionomycin were applied and calcium response was monitored by designed proteins. The application of these drugs to cells results in calcium release from the ER. Accordingly, the signals from ER-targeted calcium sensors were expected to be reduced upon adding these drugs.

Figure 4:
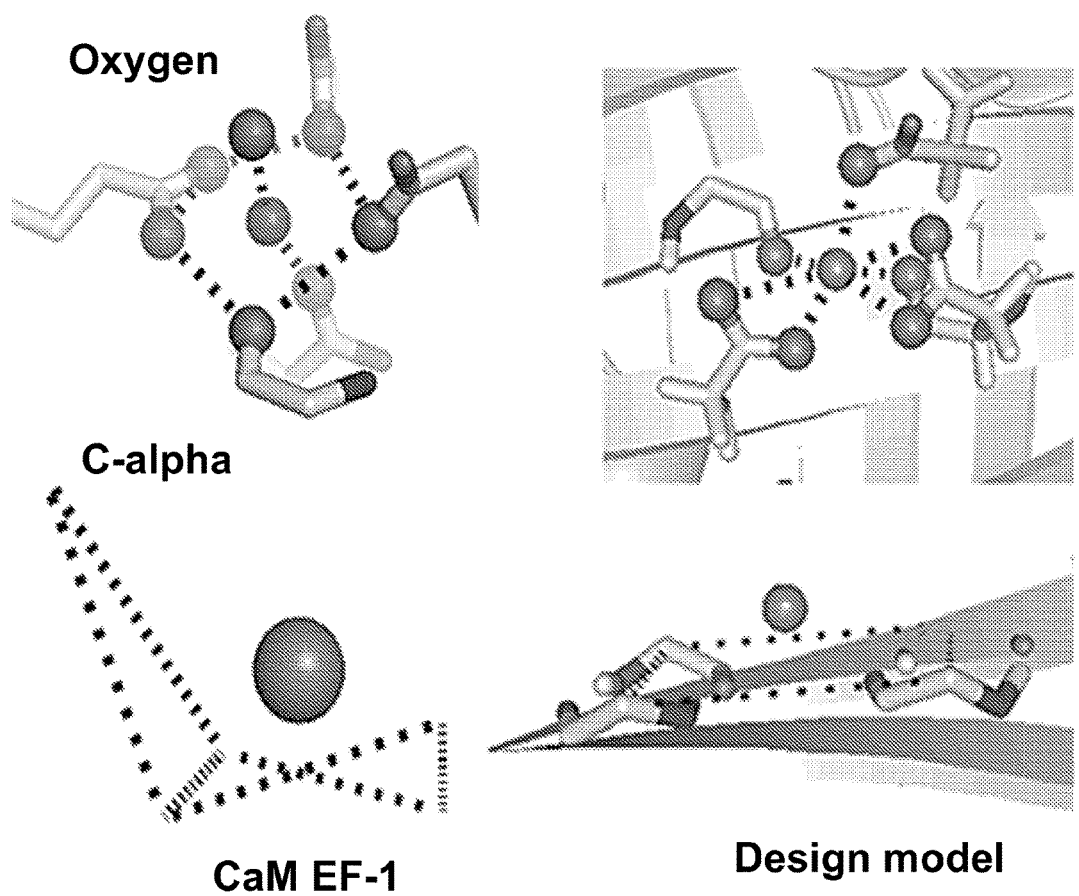
FIG. 4 illustrates a comparison of $Ca^{2+}$-coordinating oxygen and Ca geometry between the first EF-hand motif in CaM and engineered model of RapidER (MCD1) (SEQ ID NO: 43).
Figure 7A:
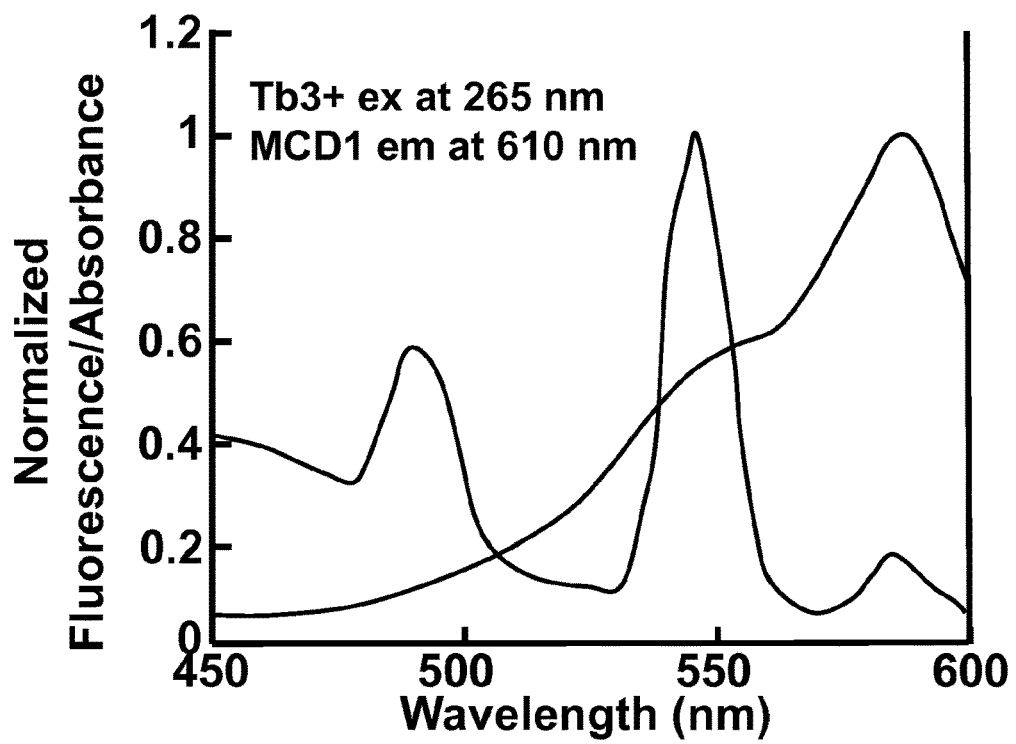
FIGS. 7A and 7B illustrate the calculated distance between ion and the chromophore.
Figure 7B:
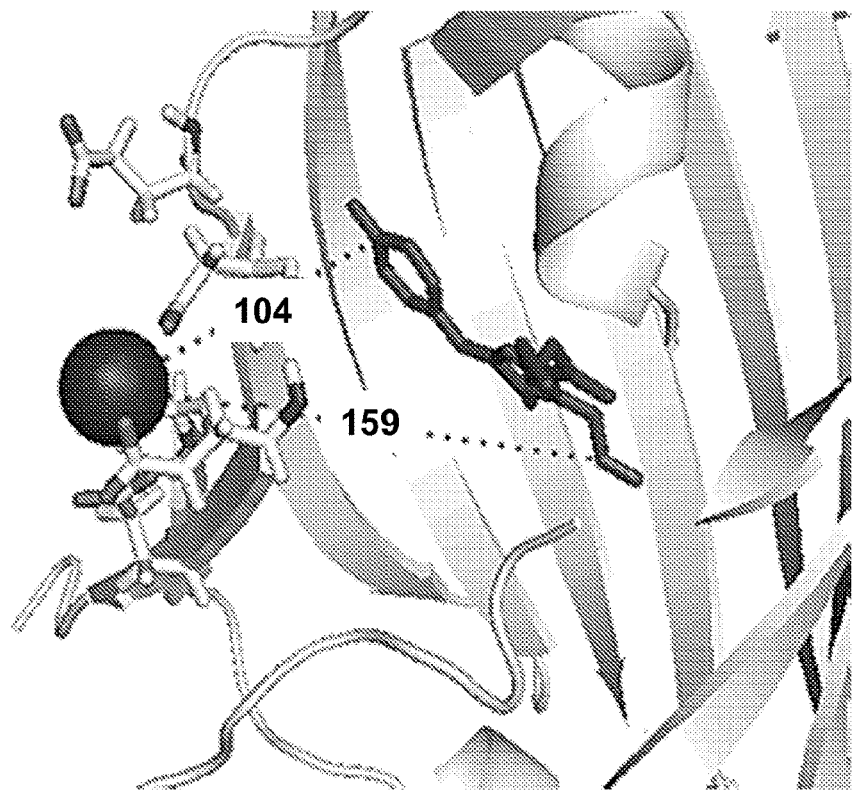
Figure 8A:
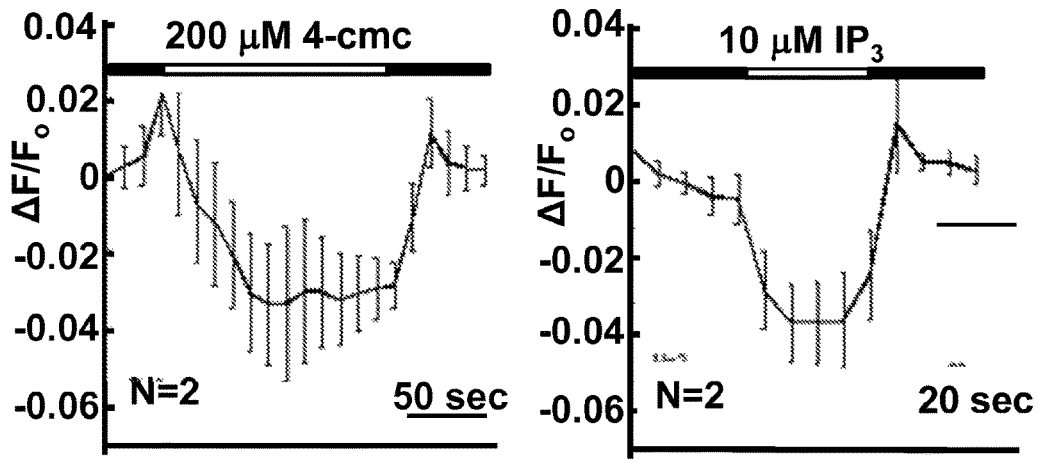
FIGS. 8A-8D illustrate the MCD15er (SEQ ID NO: 42) fluorescence change in response to drugs in transiently transfected BHK, HeLa, and C2C12 cell lines. The black bar indicates cells were applied in the standard Ringer's solution and the white one indicates the treatment of drugs in the standard Ringer's solution. The fluorescence traces $\Delta F/F_0$ were the average one from N cells.
Figure 8B:
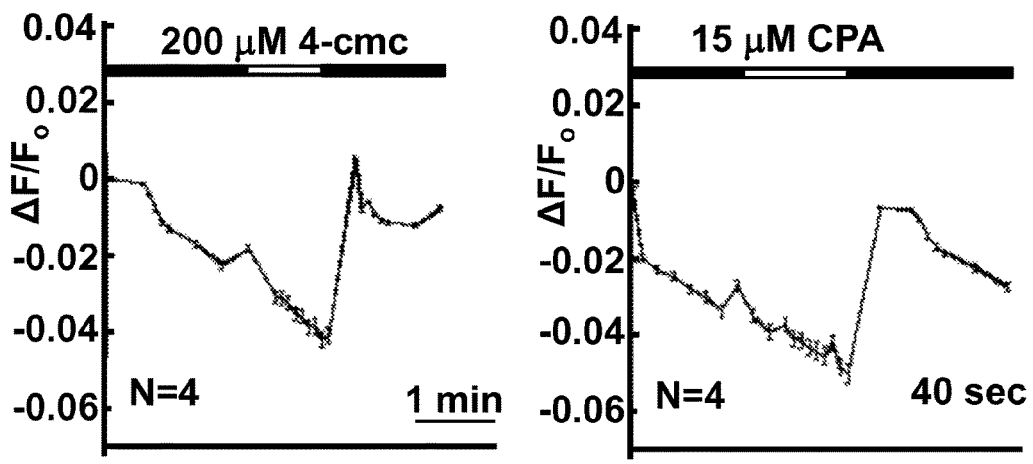
Figure 8C:
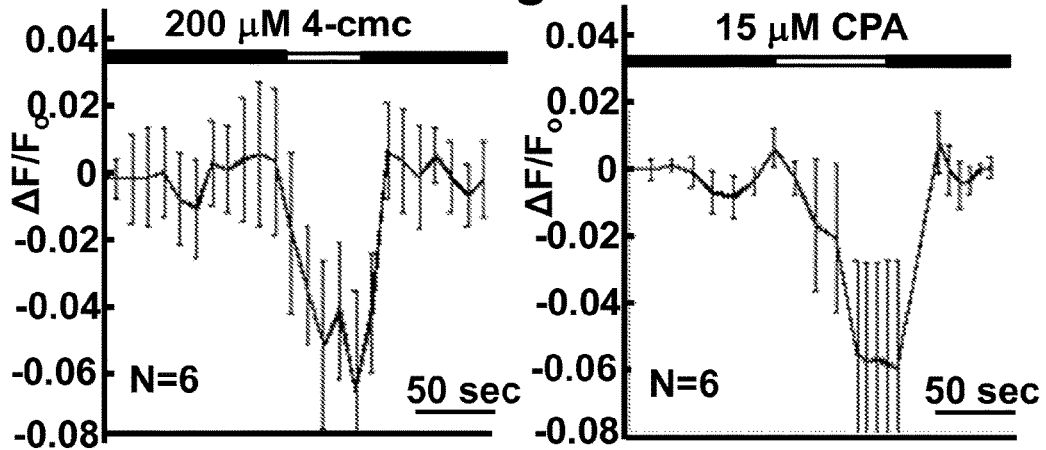
Figure 8D:
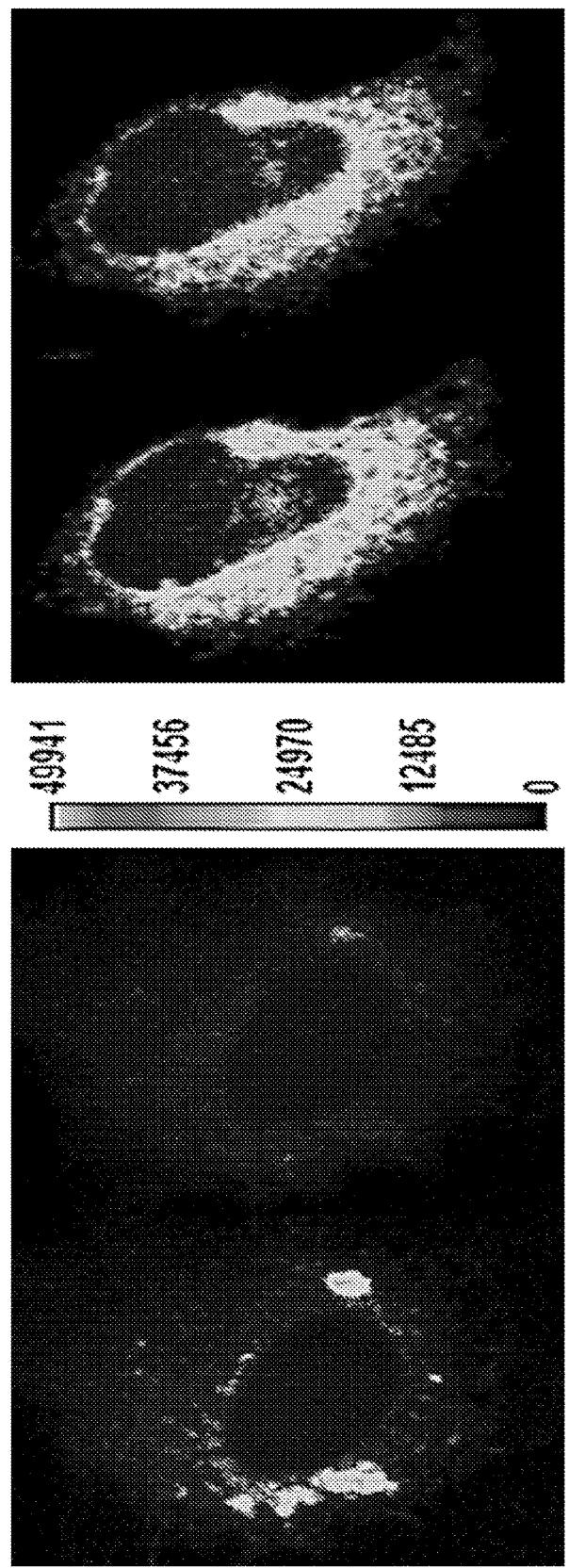
Figure 9B:
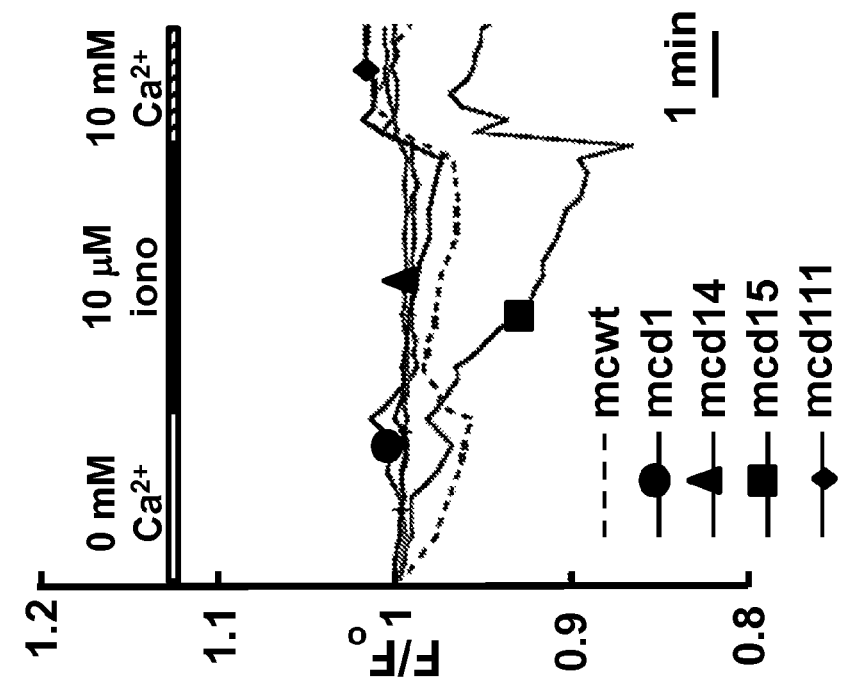
FIGS. 9A and 9B illustrate monitoring calcium ion concentration change in situ.
Figure 9A:
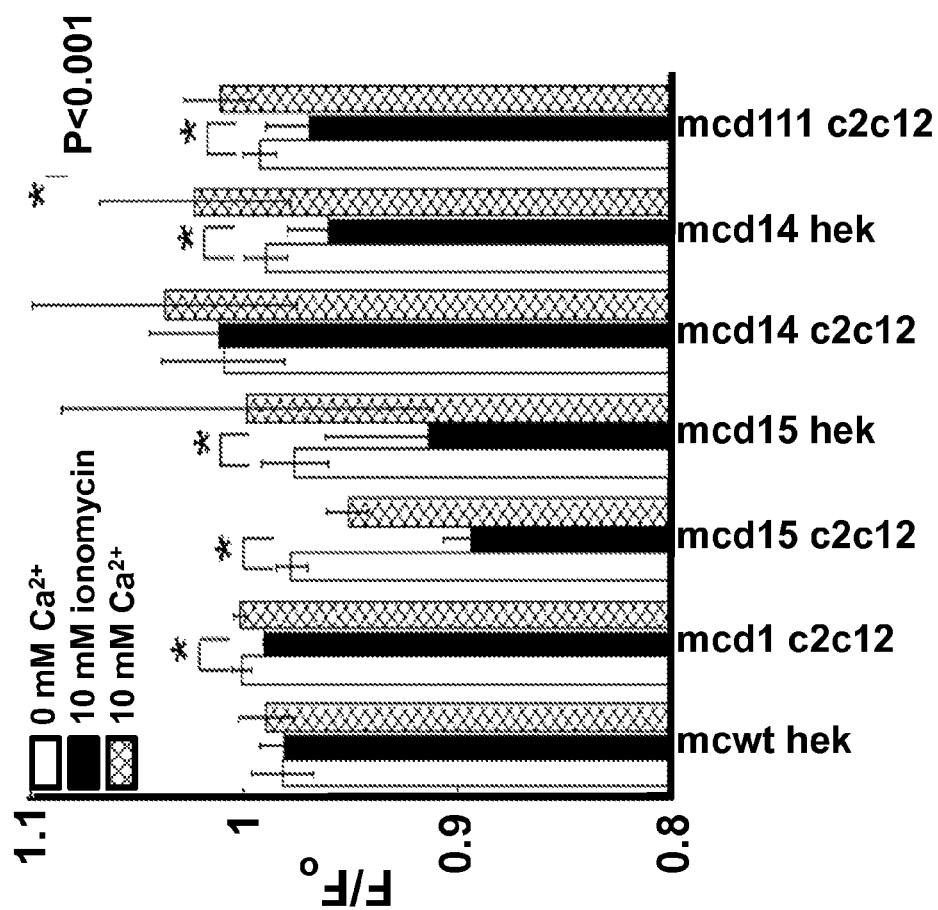
Figure 10A:
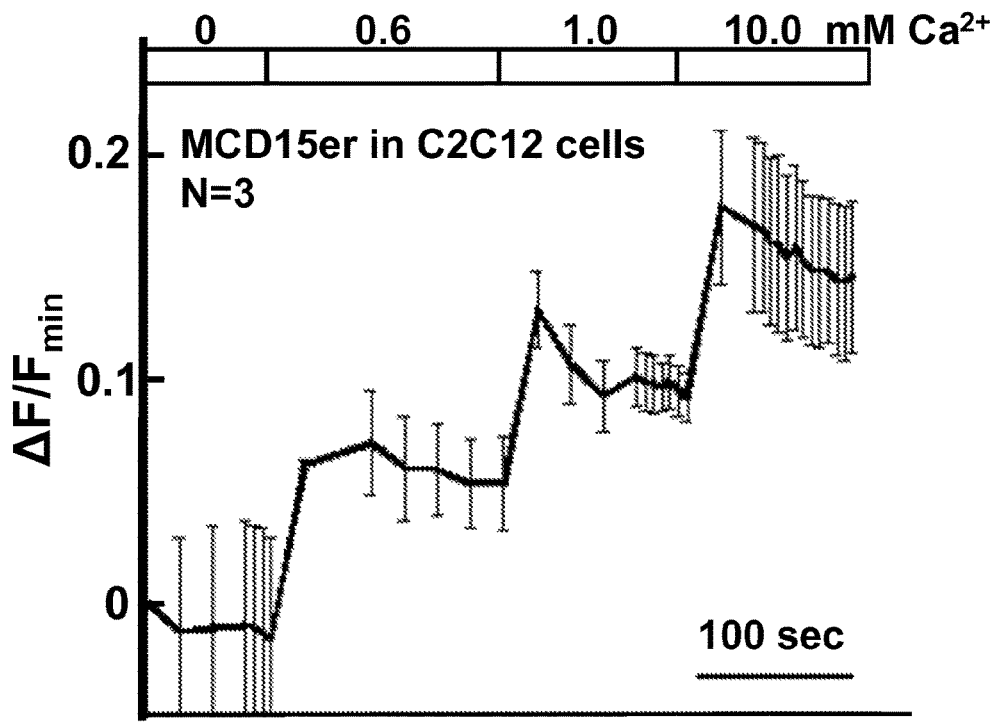
FIG. 10A is a graph illustrating calcium ion concentration calibration to MCD15 (SEQ ID NO: 45) expressed in C2C12 cells.
Figure 10B:
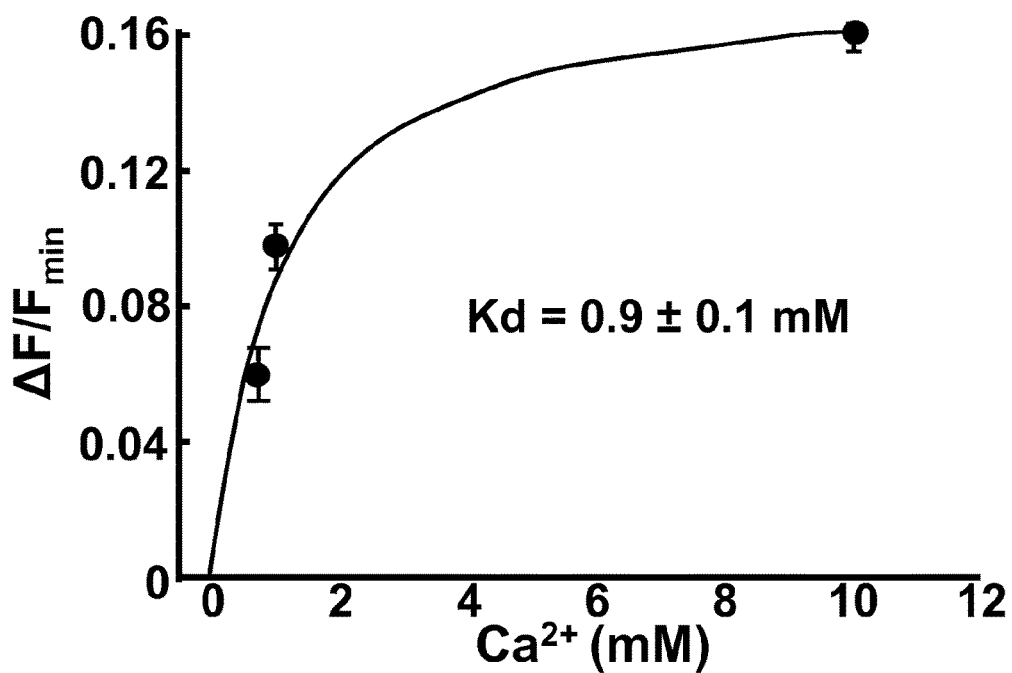
FIG. 10B is a graph illustrating calcium ion concentration calibration to MCD15 (SEQ ID NO: 45) expressed in C2C12 cells.
Figure 11A:
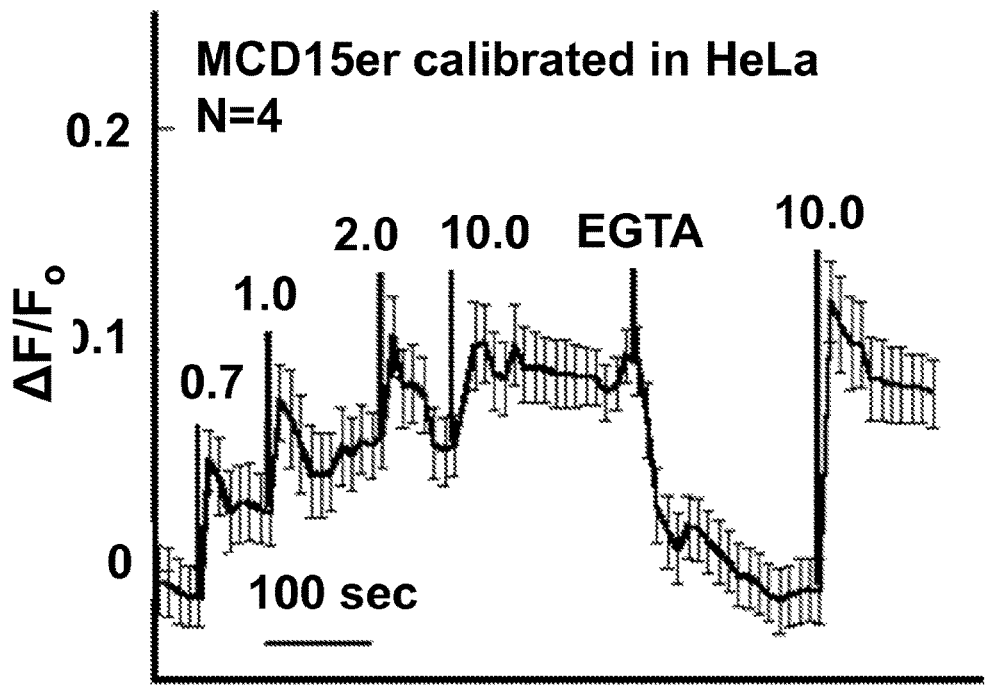
FIG. 11A is a graph illustrating calcium ion concentration calibration to MCD15 (SEQ ID NO: 45) expressed in HeLa cells.
Figure 11B:
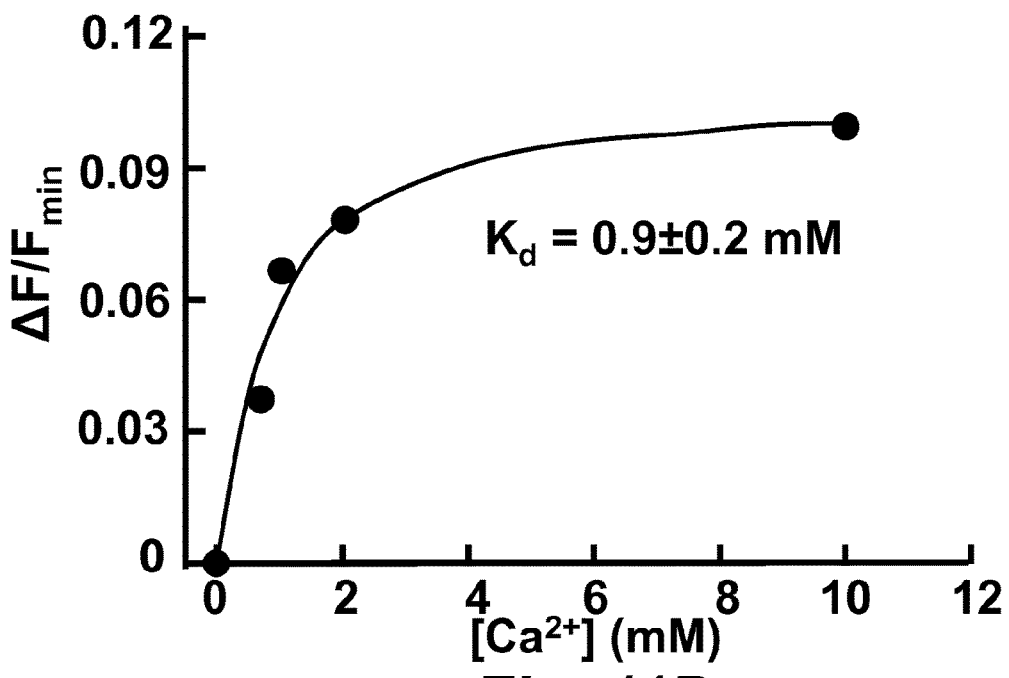
FIG. 11B is a graph illustrating calcium on concentration calibration to MCD15 (SEQ ID NO: 45) expressed in HeLa cells.
Figure 12A:
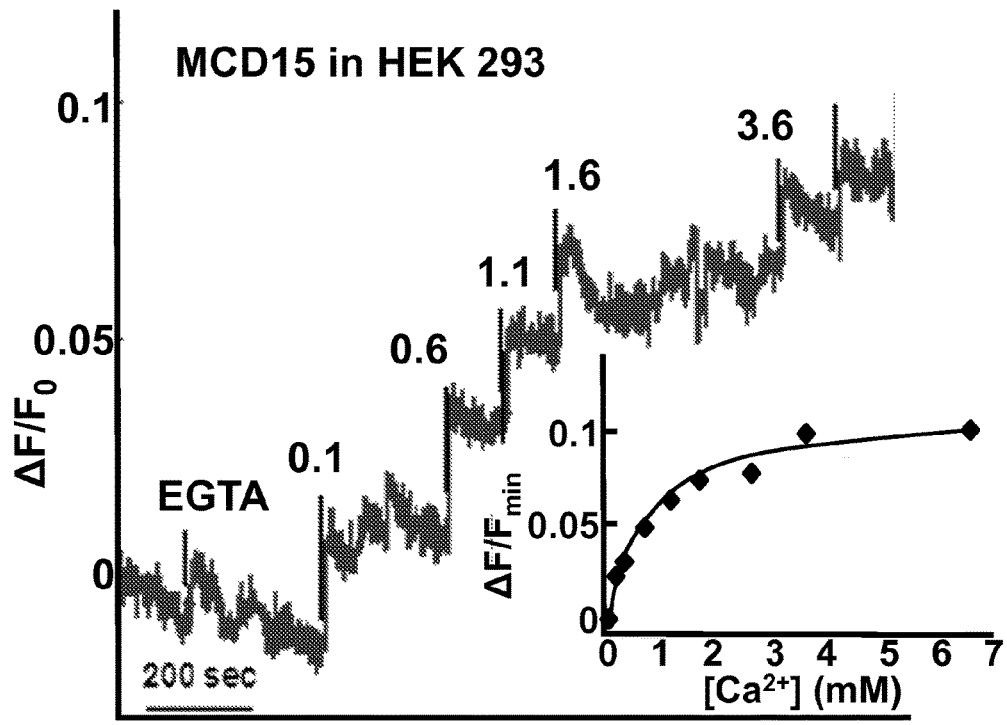
FIG. 12A is a graph illustrating calcium ion concentration calibration to MCD15 (SEQ ID NO: 45) expressed in HEK 293 cells. The apparent $K_d$ of MCD15 (SEQ ID NO: 45) expressed in HEK 293 cells is 2-folder greater than MCD15 (SEQ ID NO: 45) expressed in E. coli. in the crude total soluble protein extract.
Figure 12B:
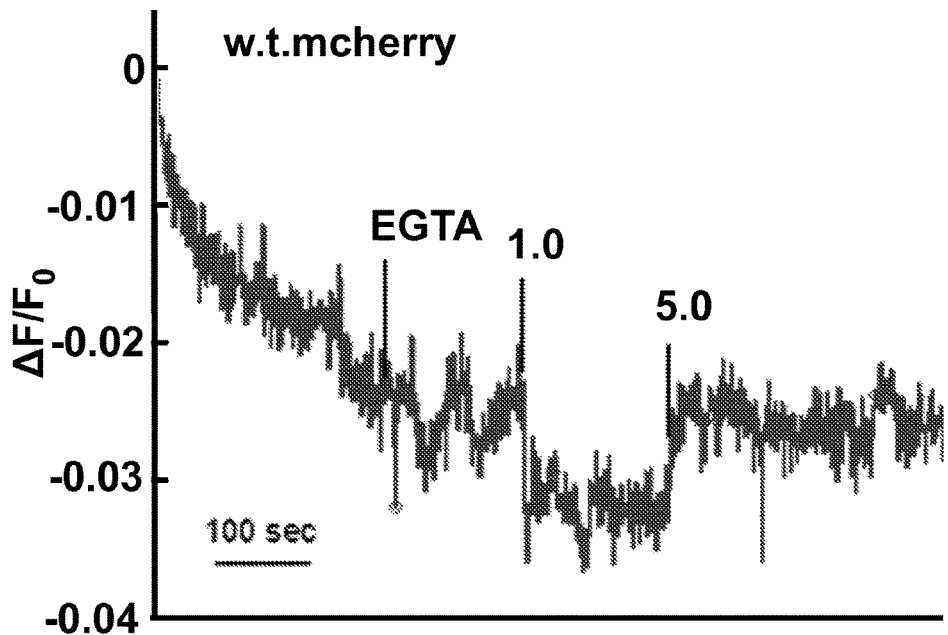
FIG. 12B is a graph illustrating calcium ion concentration calibration to wild-type mCherry (SEQ ID NO: 40) expressed in HEK 293 cells.
Figure 13:
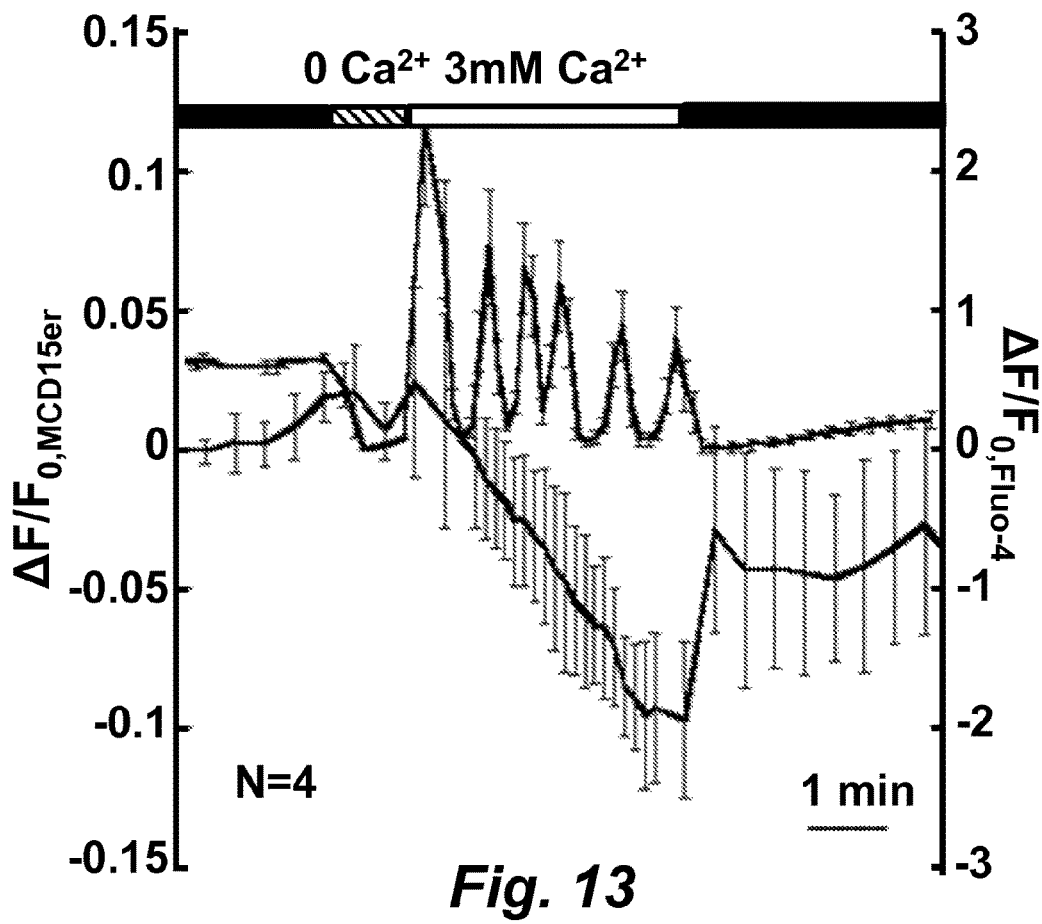
FIG. 13 is a graph illustrating measurement of calcium released from endoplasmic reticulum during intracellular calcium ion oscillation as measured by MCD15er (SEQ ID NO: 40).
Figure 14:
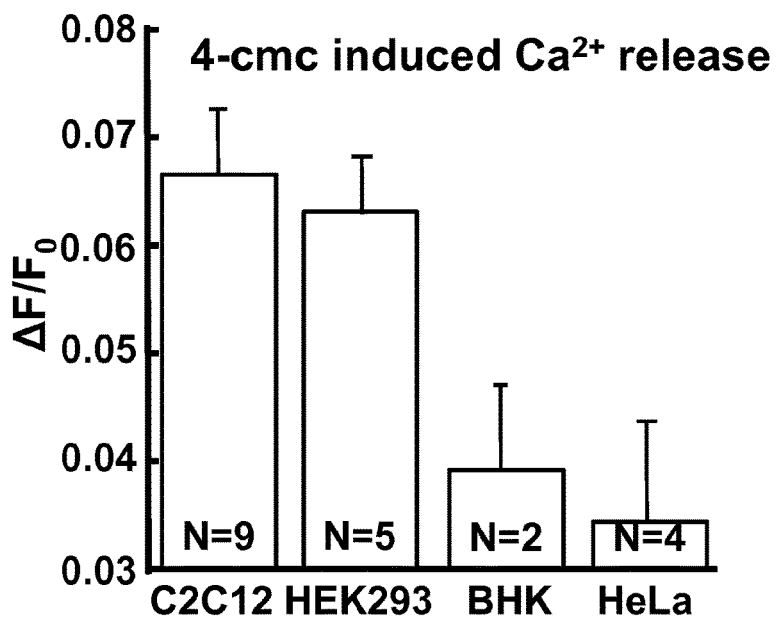
FIG. 14 is a graph illustrating 4-cmc induced calcium ion release in a variety of mammalian cells as determined with MCD15er (SEQ ID NO: 40).
Figure 16:
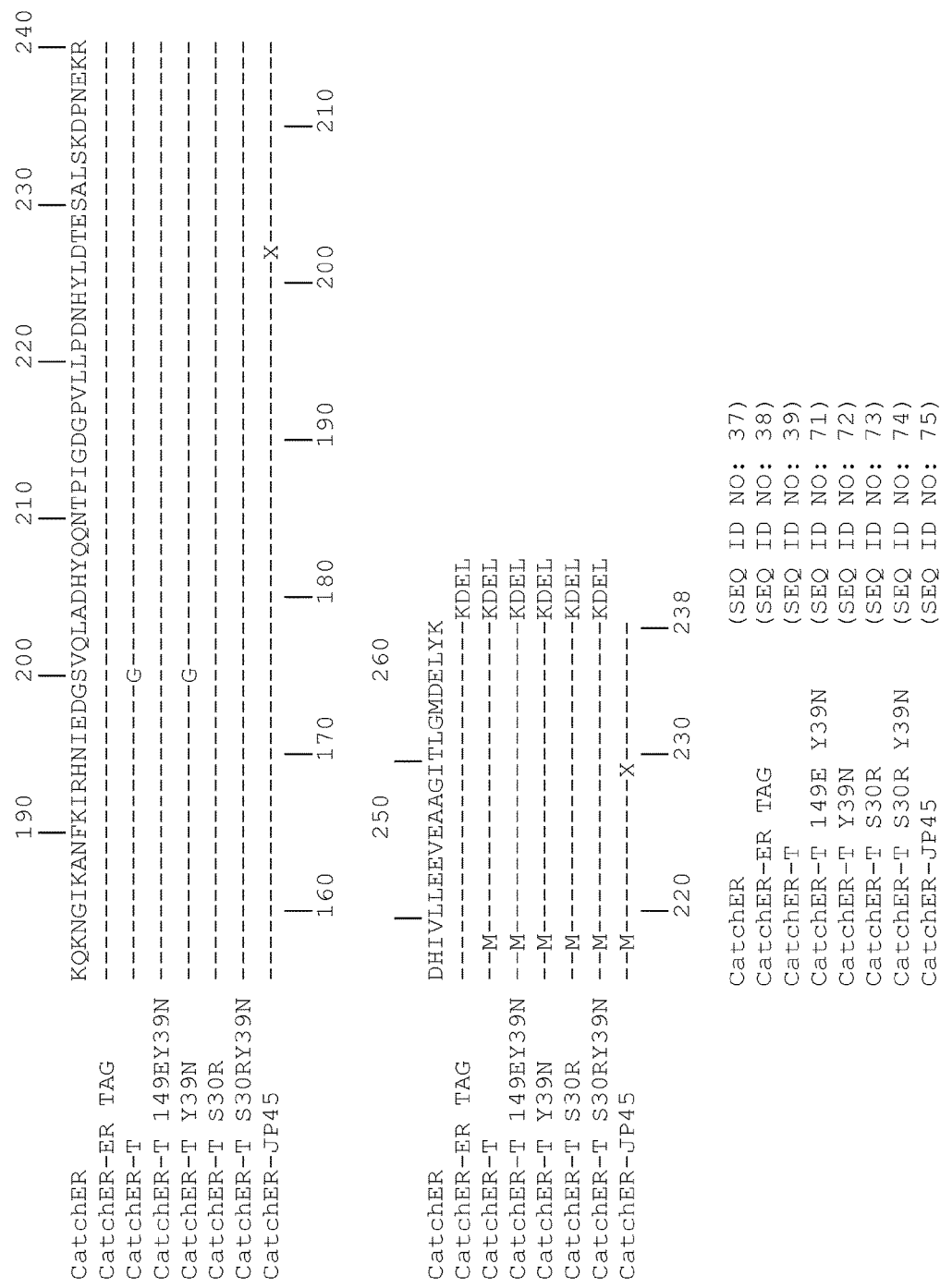
FIG. 16 illustrates the amino acid sequence alignments for the variants of the CatchER metal ion sensors of the disclosure. The chromophore is indicated in bold. Dashes indicate identical amino acids and blanks indicate deleted or absent residues.

Four cell lines, HEK-293, BHK, HeLa, and C2C12 were used to validate these sensors. Treatments of ionomycin, 4-cmc and CPA for all cell lines resulted in reductions in the degree of fluorescence intensity, as shown in FIG. 7). FIG. 4 shows the calcium release from ER triggered by ionomycin as monitored by MCD15ER (MCD15 with the ER Tag) (SEQ ID NO: 42) and Fura-2 simultaneously.

The concentration of endoplasmic reticulum calcium ($[Ca^{2+}]ER$) decreased upon addition of ionomycin, while that of cytoplasmic calcium ($[Ca^{2+}]cyt$) increased. Since no extracellular calcium was supplied, calcium was pumped out after the early stage of calcium accumulation in cytoplasma. When calcium was supplemented, the concentration of both cytoplasmic and ER [Ca2+] increased. Unlike cytosolic calcium, even if extracellular calcium was about 10 mM, calcium in ER was only recovered to its resting level.

Example 22

Metal Selectivity

Selectivity of a calcium sensor against other physiological metals and small molecules is an important criterion. The physiological metals such as $Mg^{2+}$, $Zn^{2+}$, $Cu^{2+}$, $Na^+$ and $K^+$, and small molecules such as ATP, GTP, ADP and GDP were added to the sensor pre-loaded with 1 mM $Ca^{2+}$. The optical properties was monitored by both UV-vis and fluorescence spectrophotometer. The concentrations of each competitor were as least 5 times as much as those of the free form in the physiological conditions.

What is claimed is:

1. A polypeptide metal ion sensor comprising an engineered green fluorescent polypeptide (GFP) having a heterologous metal ion binding site, wherein said engineered GFP is a variant amino acid sequence of SEQ ID NO: 37 having the mutations corresponding to L22V and I218M and, when having a metal ion species bound thereto, has an elevated fluorescence output compared to the polypeptide SEQ ID NO: 37 binding to the same metal ion species at 37° C., wherein the amino acid sequence of said engineered GFP comprises any one of the amino acid sequences selected from the group consisting of sequences having 95% similarity to any one of SEQ ID NOs: 71, 72, 73, 74, 79, 81, and 82, or wherein said engineered GFP has 100% similarity to SEQ ID NO: 80 or said engineered GFP consists of SEQ ID NO: 75.

2. The polypeptide metal ion sensor of claim 1, wherein said sensor is conjugated to at least one targeting polypeptide motif that specifically recognizes a structural feature of a cell.

3. The polypeptide metal ion sensor of claim 2, wherein said at least one targeting polypeptide motif specifically recognizes a target component of an endoplasmic reticulum or a sarcoplasmic reticulum of a cell.

4. The polypeptide metal ion sensor of claim 3, wherein said targeting polypeptide motif has at least 90% sequence identity with an amino acid sequence selected from the group consisting of the sequences SEQ ID NOs: 64, 76-78, and the sequence KDEL (SEQ ID NO. 83).

5. The polypeptide metal ion sensor of claim 1, wherein said metal ion binding site specifically binds to a metal ion selected from the group consisting of: calcium, lead, gadolinium, lanthanum, terbium, antimony, strontium, magnesium, mercury, and cadmium.

6. A method of detecting metal ions in a biological sample, comprising: (i) providing a polypeptide metal ion sensor comprising an engineered green fluorescent polypeptide (GFP) having a heterologous metal ion binding site, wherein said engineered GFP is a variant of amino acid sequence SEQ ID NO: 37 and having the amino acid substitutions corresponding to L22V and I218M and, when having a metal ion species bound thereto, has an elevated fluorescence output compared to the polypeptide SEQ ID NO: 37 binding to the same metal ion species at 37° C., wherein the amino acid sequence of said engineered GFP comprises any one of the amino acid sequences selected from the group consisting of sequences having 95% similarity to any one of SEQ ID NOs: 71, 72, 73, 74, 79, 81, and 82, or wherein said engineered GFP has 100% similarity to SEQ ID NO: 80 or said engineered GFP consists of SEQ ID NO: 75; (ii) delivering the polypeptide metal ion sensor or an expression vector having an nucleic acid sequence encoding said metal sensor to a biological sample; (iii) detecting a first fluorescent signal emitted by said sensor; (iii) generating a physiological or cellular change in the biological sample; (iv) detecting a second fluorescent signal emitted by said sensor after step (iii); and (v) comparing the first and second fluorescent signals, wherein a ratiometric change in at least one of a wavelength, an intensity, and lifetime between the first and second fluorescent signals indicates a change in the rate of release or intracellular concentration of a metal ion in the sample.

7. The method of claim 6, wherein the ratiometric change in the signal intensity provides an quantitative measurement of the metal ion in the sample.

8. The method of claim 6, wherein the biological sample is a cell or tissue of an animal or human subject, or a cell or tissue isolated from an animal or human subject.

9. The method of claim 6, wherein the fluorescence signal generated when a metal ion is bound to said sensor is used to generate an image.

* * * * *

SEQUENCE LISTING

<160> NUMBER OF SEQ ID NOS: 86

<210> SEQ ID NO 1
<211> LENGTH: 804
<212> TYPE: DNA
<213> ORGANISM: Artificial Sequence

```
<220> FEATURE:
<223> OTHER INFORMATION: CatchER-T with ER Tag

<400> SEQUENCE: 1
atgctgctat ccgtgccgtt gctgctcggc ctcctcggcc tggccgctgc agacggatcc     60 gggcccctcta gaatggtgag caagggcgag gagctgttca ccggggtggt gcccatcctg    120
gtcgagctgg acggcgacgt aaacggccac aagttcagcg tgtccggcga gggcgagggc    180
gatgccacct acggcaagct gaccctgaag ttcatctgca ccaccggcaa gctgcccgtg    240
ccctggccca ccctcgtgac caccctgacc tacggcgtgc agtgcttcag ccgctacccc    300
gaccacatga gcagcacga cttcttcaag tccgccatgc ccgaaggcta cgtccaggag    360
cgcaccatct tcttcaagga cgacggcaac tacaagaccc gcgccgaggt gaagttcgag    420
ggcgacaccc tggtgaaccg catcgagctg aagggcatcg acttcaagga ggacggcaac    480
atcctggggc acaagctgga gtacaactac aacgagcaca cgtctatat cacggccgac    540 aagcagaaga acggcatcaa ggcgaacttc aagatccgcc acaacatcga ggacggcggc    600
gtgcagctcg ccgaccacta ccagcagaac ccccccatcg gcgacggccc cgtgctgctg    660
cccgacaacc actacctgga caccgaatcc gccctgagca aagacccaa cgagaagcgc    720 gatcacatgg tcctgctgga ggaggtggag gccgccggga tcactctcgg catggacgag    780
ctgtacaaga aggacgagct gtaa                                          804

<210> SEQ ID NO 2
<211> LENGTH: 996
<212> TYPE: DNA
<213> ORGANISM: Artificial Sequence
<220> FEATURE:
<223> OTHER INFORMATION: Z10Cat
<220> FEATURE:
<221> NAME/KEY: misc_feature
<222> LOCATION: (699)..(699)
<223> OTHER INFORMATION: n is a, c, g, or t

<400> SEQUENCE: 2
atggatgaat acgagctcta ccgggtggtc ttcgacatca ccttcttctt cttcgtcatt     60
gtcatcctgc tggccatcat ccagggtctg attatcgacg ccttcggcga gctcccagcc    120
accatggtga gcaagggcga ggagctgttc accggggtgg tgcccatcct ggtcgagctg    180
gacggcgacg taaacggcca aagttcagc gtgtccggcg agggcgaggg cgatgccacc    240
tacggcaagc tgaccctgaa gttcatctgc accaccggca agctgcccgt gccctggccc    300
accctcgtga ccaccctgac ctacggcgtg cagtgcttca gccgctaccc cgaccacatg    360 agcagcacg acttcttcaa gtccgccatg cccgaaggct acgtccagga gcgcaccatc    420
ttcttcaagg acgacggcaa ctacaagacc cgcgccgagg tgaagttcga gggcgacacc    480
ctggtgaacc gcatcgagct gaagggcatc gacttcaagg aggacggcaa catcctgggg    540 cacaagctg agtacaacta caacgagcac acgtctata tcacggccga caagcagaag    600
aacggcatca aggcgaactt caagatccgc cacaacatcg aggacggcag cgtgcagctc    660
gccgaccact accagcagaa ccccccatc ggcgacggnc cgtgctgct gcccgacaac    720 cactacctgg acaccgaatc cgccctgagc aaagacccca cgagaagcg cgatcacatg    780 gtcctgctgg aggaggtgga ggccgccggg atcactctcg gcatggacga gctgtacaag    840
tcgcttccag cattcttgaa ctacctctcc cggaacttct acaccctgcg cttccttgcc    900
ctcttcttgg cgtttgccat caacttcatc ctgctgtttt ataaggtctc agactctcca    960
```

```
ccaggggagg atgacatgga gggctcggca gcataa                              996
```

<210> SEQ ID NO 3
<211> LENGTH: 789
<212> TYPE: DNA
<213> ORGANISM: Artificial Sequence
<220> FEATURE:
<223> OTHER INFORMATION: CatZ5

<400> SEQUENCE: 3

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cgagcacaac gtctatatca cggccgacaa gcagaagaac   480
ggcatcaagg cgaacttcaa gatccgccac aacatcgagg acggcagcgt gcagctcgcc   540
gaccactacc agcagaacac ccccatcggc gacggccccg tgctgctgcc cgacaaccac   600
tacctggaca ccgaatccgc cctgagcaaa gaccccaacg agaagcgcga tcacatggtc   660
ctgctggagg aggtggaggc cgccgggatc actctcggca tggacgagct gtacaagacc   720
ctgcgcttcc ttgccctctt cttggcgttt gccatcaact tcatcctgct gttttataag   780
gtctcctaa                                                          789
```

<210> SEQ ID NO 4
<211> LENGTH: 861
<212> TYPE: DNA
<213> ORGANISM: Artificial Sequence
<220> FEATURE:
<223> OTHER INFORMATION: CateZ5

<400> SEQUENCE: 4

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cgagcacaac gtctatatca cggccgacaa gcagaagaac   480
ggcatcaagg cgaacttcaa gatccgccac aacatcgagg acggcagcgt gcagctcgcc   540
gaccactacc agcagaacac ccccatcggc gacggccccg tgctgctgcc cgacaaccac   600
tacctggaca ccgaatccgc cctgagcaaa gaccccaacg agaagcgcga tcacatggtc   660
ctgctggagg aggtggaggc cgccgggatc actctcggca tggacgagct gtacaagttc   720
ttgaactacc tctcccggaa cttctacacc ctgcgcttcc ttgccctctt cttggcgttt   780
gccatcaact tcatcctgct gttttataag gtctccgact ctccaccagg ggaggatgac   840
atggagggct cggcagcata a                                            861
```

<210> SEQ ID NO 5
<211> LENGTH: 873
<212> TYPE: DNA
<213> ORGANISM: Artificial Sequence
<220> FEATURE:
<223> OTHER INFORMATION: CatLeZ5

<400> SEQUENCE: 5

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cgagcacaac gtctatatca cggccgacaa gcagaagaac     480
ggcatcaagg cgaacttcaa gatccgccac aacatcgagg acggcagcgt gcagctcgcc     540
gaccactacc agcagaacac ccccatcggc gacggccccg tgctgctgcc cgacaaccac     600
tacctggaca ccgaatccgc cctgagcaaa gaccccaacg agaagcgcga tcacatggtc     660
ctgctggagg aggtggaggc cgccgggatc actctcggca tggacgagct gtacaagtcg     720
cttccagcat tcttgaacta cctctcccgg aacttctaca ccctgcgctt ccttgccctc     780
ttcttggcgt ttgccatcaa cttcatcctg ctgtttata aggtctccga ctctccacca     840
ggggaggatg acatggaggg ctcggcagca taa                                  873
```

<210> SEQ ID NO 6
<211> LENGTH: 1065
<212> TYPE: DNA
<213> ORGANISM: Artificial Sequence
<220> FEATURE:
<223> OTHER INFORMATION: CatFKBP

<400> SEQUENCE: 6

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cgagcacaac gtctatatca cggccgacaa gcagaagaac     480
ggcatcaagg cgaacttcaa gatccgccac aacatcgagg acggcagcgt gcagctcgcc     540
gaccactacc agcagaacac ccccatcggc gacggccccg tgctgctgcc cgacaaccac     600
tacctggaca ccgaatccgc cctgagcaaa gaccccaacg agaagcgcga tcacatggtc     660
ctgctggagg aggtggaggc cgccgggatc actctcggca tggacgagct gtacaaggga     720
ggttcaggtg gaatcgatat gggagtggaa attgaaacca ctcccccagg agacgggcgc     780
accttcccca agaaaggcca gaccgcggtg gtgcactaca ccgggatgct tcagaacgga     840
```

| | |
|---|---|
| aagaaatttg attcctcccg ggacagaaac aagcccttta agtttcgcat cggcaagcag | 900 |
| gaggtgatca aaggctttga agaaggggcg gcccagatga gtctgggtca gagagccaaa | 960 |
| ctgactataa ccccagatgt ggcctatggt gccactgggc acccaggcgt gatcccacca | 1020 |
| aacgccactc tcattttcga gtgtggagctt ctaaacctgg aataa | 1065 |

<210> SEQ ID NO 7
<211> LENGTH: 792
<212> TYPE: DNA
<213> ORGANISM: Artificial Sequence
<220> FEATURE:
<223> OTHER INFORMATION: MCD1 with ER Tag

<400> SEQUENCE: 7

| | |
|---|---|
| atgctgctat ccgtgccgtt gctgctcggc ctcctcggcc tggccgctgc agacggggat | 60 |
| cccgccacca tggtgagcaa gggcgaggag gataacatgg ccatcatcaa ggagttcatg | 120 |
| cgcttcaagg tgcacatgga gggctccgtg aacggccacg agttcgagat cgagggcgag | 180 |
| ggcgagggcc gcccctacga gggcacccag accgccaagc tgaaggtgac caagggtggc | 240 |
| cccctgccct cgcctggga catcctgtcc cctcagttca gtacggctc caaggcctac | 300 |
| gtgaagcacc ccgccgacat ccccgactac ttgaagctgt ccttccccga gggcttcaag | 360 |
| tgggagcgcg tgatgaactt cgaggacggc ggcgtggtga ccgtgaccca ggactcctcc | 420 |
| ctgcaggacg gcgagttcat ctacaaggtg aagctgcgcg gcaccaactt ccctccgac | 480 |
| ggccccgtaa tgcagaagaa gaccatgggc tgggaggagt cctccgagcg gatgtacccc | 540 |
| gaggacggcg ccctgaaggg cgagatcaag cagaggctga agctgaagga cggcggccac | 600 |
| tacgacgctg aggtcaagac cacctacaag gccaagaagc ccgtgcagct gcccggcgcc | 660 |
| tacaacgtcg acatcgactt ggacatcacc tcccacaacg aggactacac catcgtggaa | 720 |
| cagtacgaag aggccgaggg ccgccactcc accggcggca tggacgagct gtacaagaag | 780 |
| gacgagctgt aa | 792 |

<210> SEQ ID NO 8
<211> LENGTH: 792
<212> TYPE: DNA
<213> ORGANISM: Artificial Sequence
<220> FEATURE:
<223> OTHER INFORMATION: MCD15 with ER Tag

<400> SEQUENCE: 8

| | |
|---|---|
| atgctgctat ccgtgccgtt gctgctcggc ctcctcggcc tggccgctgc agacggggat | 60 |
| cccgccacca tggtgagcaa gggcgaggag gataacatgg ccatcatcaa ggagttcatg | 120 |
| cgcttcaagg tgcacatgga gggctccgtg aacggccacg agttcgagat cgagggcgag | 180 |
| ggcgagggcc gcccctacga gggcacccag accgccaagc tgaaggtgac caagggtggc | 240 |
| cccctgccct cgcctggga catcctgtcc cctcagttca gtacggctc caaggcctac | 300 |
| gtgaagcacc ccgccgacat ccccgactac ttgaagctgt ccttccccga gggcttcaag | 360 |
| tgggagcgcg tgatgaactt cgaggacggc ggcgtggtga ccgtgaccca ggactcctcc | 420 |
| ctgcaggacg gcgagttcat ctacaaggtg aagctgcgcg gcaccaactt ccctccgac | 480 |
| ggccccgtaa tgcagaagaa gaccatgggc tgggaggagt cctccgagcg gatgtacccc | 540 |
| gaggacggcg ccctgaaggg cgagatcaag cagaggctga agctgaagga cggcggccac | 600 |
| tacgacgctg aggtcaagac cacctacaag gccaagaagc ccgtgcagct gcccggcgcc | 660 |
| tacaacgtcg acatcgagtt ggacatcacc tcccacaacg aggactacac catcgtggaa | 720 |

```
cagtacgaag aggccgaggg cgagcactcc accggcggca tggacgagct gtacaagaag    780
gacgagctgt aa                                                        792

<210> SEQ ID NO 9
<211> LENGTH: 711
<212> TYPE: DNA
<213> ORGANISM: Artificial Sequence
<220> FEATURE:
<223> OTHER INFORMATION: MCD14 without Tag

<400> SEQUENCE: 9
atggtgagca agggcgagga ggataacatg gccatcatca aggagttcat gcgcttcaag     60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
ggcgagttca tctacaaggt gaagctgcgc ggcaccaact tcccctccga cggccccgta    420
atgcagaaga gaccatgggc ctgggaggag tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
gacatcgact gggacatcac ctcccacaac gaggactaca ccatcgtgga acagtacgaa    660
gaggccgagg gcgagcactc caccggcggc atggacgagc tgtacaagta a             711

<210> SEQ ID NO 10
<211> LENGTH: 816
<212> TYPE: DNA
<213> ORGANISM: Artificial Sequence
<220> FEATURE:
<223> OTHER INFORMATION: MCD14Y with His Tag

<400> SEQUENCE: 10
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg ccacgagtt cgagatcgag gcgagggcg agggccgccc ctacgagggc    240
acccagaccg ccaagctgaa ggtgaccaag ggtggccccc tgcccttcgc ctgggacatc    300
ctgtcccctc agttcatgta cggctccaag gcctacgtga agcaccccgc cgacatcccc    360
gactacttga gctgtccctt ccccgagggc ttcaagtggg agcgcgtgat gaacttcgag    420
gacggcggcg tggtgaccgt gacccaggac tcctccctgc aggacggcga gttcatctac    480
aaggtgaagc tgcgcggcac caacttcccc tccgacggcc ccgtaatgca gaagaagacc    540
atgggctggg aggagtcctc cgagcggatg taccccgagg acggcgccct gaagggcgag    600
atcaagcaga ggctgaagct gaaggacggc ggccactacg acgctgaggt caagaccacc    660
tacaaggcca gaagcccgt gcagctgccc ggcgcctaca cgtcgacta tgacttggac    720 atcacctccc acaacgagga ctacaccatc gtggaacagt acgaagaggc cgagggcgag    780
cactccaccg gcggcatgga cgagctgtac aagtaa                              816

<210> SEQ ID NO 11
```

```
<211> LENGTH: 816
<212> TYPE: DNA
<213> ORGANISM: Artificial Sequence
<220> FEATURE:
<223> OTHER INFORMATION: MCD14YS with His Tag

<400> SEQUENCE: 11
atgcggggtt ctcatcatca tcatcatcat ggtatggcta gcatgactgg tggacagcaa      60
atgggtcggg atctgtacga cgatgacgat aaggatcccg ccaccatggt gagcaagggc     120
gaggaggata acatggccat catcaaggag ttcatgcgct tcaaggtgca catggagggc     180
tccgtgaacg gccacgagtt cgagatcgag ggcgagggcg agggccgccc ctacgagggc     240
acccagaccg ccaagctgaa ggtgaccaag ggtggccccc tgcccttcgc ctgggacatc     300
ctgtcccctc agttcatgta cggctccaag gcctacgtga agcacccgc cgacatcccc      360 gactacttga agctgtcctt ccccgagggc ttcaagtggg agcgcgtgat gaacttcgag     420
gacggcggcg tggtgaccgt gacccaggac tcctccctgc aggacggcga gttcatctac     480
aaggtgaagc tgcgcggcac caacttcccc tccgacggcc ccgtaatgca gaagaagacc     540
atgggctggg aggagtcctc cgagcggatg taccccgagg acggcgccct gaagggcgag     600
atcaagcaga ggctgaagct gaaggacggc ggccactacg acgctgaggt caagaccacc     660
tacaaggcca agaagcccgt gcagctgccc ggcgcctaca cgtcgacta tgactcggac      720 atcacctccc acaacgagga ctacaccatc gtggaacagt acgaagaggc cgagggcgag     780
cactccaccg gcggcatgga cgagctgtac aagtaa                              816

<210> SEQ ID NO 12
<211> LENGTH: 792
<212> TYPE: DNA
<213> ORGANISM: Artificial Sequence
<220> FEATURE:
<223> OTHER INFORMATION: MCD16 with ER Tag

<400> SEQUENCE: 12
atgctgctat ccgtgccgtt gctgctcggc ctcctcggcc tggccgctgc agacggggat      60
cccgccacca tggtgagcaa gggcgaggag ataacatgg ccatcatcaa ggagttcatg     120
cgcttcaagg tgcacatgga gggctccgtg aacggccacg agttcgagat cgaggcgag    180 ggcgagggcc gcccctacga gggcacccag accgccaagc tgaaggtgac caagggtggc     240
cccctgccct tcgcctggga catcctgtcc cctcagttca tgtacggctc caaggcctac     300
gtgaagcacc ccgccgacat ccccgactac ttgaagctgt ccttccccga gggcttcaag     360
tgggagcgcg tgatgaactt cgaggacggc ggcgtggtga ccgtgaccca ggactcctcc     420
ctgcaggacg cgagttcat ctacaaggtg aagctgcgcg gcaccaactt ccctccgac      480 ggccccgtaa tgcagaagaa gaccatgggc tgggaggagt ccgacgagcg gatgtacccc     540
gaggacggcg ccctgaaggg cgagatcaag cagaggctga agctgaagga cggcggccac     600
tacgacgctg aggtcaagac cacctacaag gccaagaagc ccgtgcagct gcccggcgcc     660
tacaacgtcg acatcgactt ggacatcacc tcccacaacg aggactacac catcgtggaa     720
cagtacgaag aggccgaggg cgagcactcc accggcggca tggacgagct gtacaagaag     780
gacgagctgt aa                                                         792

<210> SEQ ID NO 13
<211> LENGTH: 792
<212> TYPE: DNA
<213> ORGANISM: Artificial Sequence
```

<220> FEATURE:
<223> OTHER INFORMATION: MCD17 with ER Tag

<400> SEQUENCE: 13

```
atgctgctat ccgtgccgtt gctgctcggc ctcctcggcc tggccgctgc agacggggat      60
cccgccacca tggtgagcaa gggcgaggag ataacatgg ccatcatcaa ggagttcatg     120
cgcttcaagg tgcacatgga gggctccgtg aacggccacg agttcgagat cgagggcgag     180
ggcgagggcc gccccctacga gggcacccag accgccaagc tgaaggtgac caagggtggc     240
cccctgccct cgcctgggca catcctgtcc cctcagttca tgtacggctc caaggcctac     300
gtgaagcacc ccgccgacat ccccgactac ttgaagctgt ccttccccga gggcttcaag     360
tgggagcgcg tgatgaactt cgaggacggc ggcgtggtga ccgtgaccca ggactcctcc     420
ctgcaggacg gcgagttcat ctacaaggtg aagctgcgcg gcaccaactt ccctccgac       480
ggccccgtaa tgcagaagaa gaccatgggc tgggaggagt cctccgagcg gatgtacccc     540
gaggacggcg ccctgaaggg cgagatcaag cagaggctga agctgaagga cggcggccac     600
tacgacgctg aggtcaagac cacctacaag gccaagaagc ccgtgcagct gcccggcgcc     660
tacaacgtcg acaccgagtc cgccatcacc tcccacaacg aggactacac catcgtggaa     720
cagtacgaag aggccgaggg cgagcactcc accggcggca tggacgagct gtacaagaag     780
gacgagctgt aa                                                          792
```

<210> SEQ ID NO 14
<211> LENGTH: 792
<212> TYPE: DNA
<213> ORGANISM: Artificial Sequence
<220> FEATURE:
<223> OTHER INFORMATION: MCD18 with ER Tag

<400> SEQUENCE: 14

```
atgctgctat ccgtgccgtt gctgctcggc ctcctcggcc tggccgctgc agacggggat      60
cccgccacca tggtgagcaa gggcgaggag ataacatgg ccatcatcaa ggagttcatg     120
cgcttcaagg tgcacatgga gggctccgtg aacggccacg agttcgagat cgagggcgag     180
ggcgagggcc gccccctacga gggcacccag accgccaagc tgaaggtgac caagggtggc     240
cccctgccct cgcctgggca catcctgtcc cctcagttca tgtacggctc caaggcctac     300
gtgaagcacc ccgccgacat ccccgactac ttgaagctgt ccttccccga gggcttcaag     360
tgggagcgcg tgatgaactt cgaggacggc ggcgtggtga ccgtgaccca ggactcctcc     420
ctgcaggacg gcgagttcat ctacaaggtg aagctgcgcg gcaccaactt ccctccgac       480
ggccccgtaa tgcagaagaa gaccatgggc tgggaggagt cctccgagcg gatgtacccc     540
gaggacggcg ccctgaaggg cgagatcaag cagaggctga agctgaagga cggcggccac     600
tacgacgctg aggtcaagac cacctacaag gccaagaagc ccgtgcagct gcccggcgcc     660
tacaacgtcg acatcgagtt ggccatcacc tcccacaacg aggactacac catcgtggaa     720
cagtacgaag aggccgaggg cgagcactcc accggcggca tggacgagct gtacaagaag     780
gacgagctgt aa                                                          792
```

<210> SEQ ID NO 15
<211> LENGTH: 792
<212> TYPE: DNA
<213> ORGANISM: Artificial Sequence
<220> FEATURE:
<223> OTHER INFORMATION: MCD19 with ER Tag

<400> SEQUENCE: 15

```
atgctgctat ccgtgccgtt gctgctcggc ctcctcggcc tggccgctgc agacggggat    60
cccgccacca tggtgagcaa gggcgaggag ataacatgg ccatcatcaa ggagttcatg   120
cgcttcaagg tgcacatgga gggctccgtg aacggcacg agttcgagat cgagggcgag   180
ggcgagggcc gcccctacga gggcacccag accgccaagc tgaaggtgac caagggtggc   240
cccctgccct cgcctggga catcctgtcc cctcagttca gtacggctc caaggcctac   300
gtgaagcacc ccgccgacat ccccgactac ttgaagctgt ccttcccga gggcttcaag   360
tgggagcgcg tgatgaactt cgaggacggc ggcgtggtga ccgtgaccca ggactcctcc   420
ctgcaggacg gcgagttcat ctacaaggtg aagctgcgcg gcaccaactt cccctccgac   480
ggccccgtaa tgcagaagaa gaccatgggc tgggaggagt cctccgagcg gatgtacccc   540
gaggacggcg ccctgaaggg cgagatcaag cagaggctga agctgaagga cggcggccac   600
tacgacgctg aggtcaagac cacctacaag gccaagaagc ccgtgcagct gcccggcgcc   660
tacaacgtcg acatcgagtt ggacatcacc tcccacaacg aggactacac catcgtggaa   720
cagtacgaag aggccgaggg ccgccactcc accggcggca tggacgagct gtacaagaag   780
gacgagctgt aa                                                        792
```

<210> SEQ ID NO 16
<211> LENGTH: 792
<212> TYPE: DNA
<213> ORGANISM: Artificial Sequence
<220> FEATURE:
<223> OTHER INFORMATION: MCD110 with ER Tag

<400> SEQUENCE: 16

```
atgctgctat ccgtgccgtt gctgctcggc ctcctcggcc tggccgctgc agacggggat    60
cccgccacca tggtgagcaa gggcgaggag ataacatgg ccatcatcaa ggagttcatg   120
cgcttcaagg tgcacatgga gggctccgtg aacggcacg agttcgagat cgagggcgag   180
ggcgagggcc gcccctacga gggcacccag accgccaagc tgaaggtgac caagggtggc   240
cccctgccct cgcctggga catcctgtcc cctcagttca gtacggctc caaggcctac   300
gtgaagcacc ccgccgacat ccccgactac ttgaagctgt ccttcccga gggcttcaag   360
tgggagcgcg tgatgaactt cgaggacggc ggcgtggtga ccgtgaccca ggactcctcc   420
ctgcaggacg gcgagttcat ctacaaggtg aagctgcgcg gcaccaactt cccctccgac   480
ggccccgtaa tgcagaagaa gaccatgggc tgggaggagt cctccgagcg gatgtacccc   540
gaggacggcg ccctgaaggg cgagatcaag cagaggctga agctgaagga cggcggccac   600
tacgacgctg aggtcaagac cacctacaag gccaagaagc ccgtgcagct gcccggcgcc   660
tacaacgtcg acatcgagtc ggacatcacc tcccacaacg aggactacac catcgtggaa   720
cagtacgaag aggccgaggg cgagcactcc accggcggca tggacgagct gtacaagaag   780
gacgagctgt aa                                                        792
```

<210> SEQ ID NO 17
<211> LENGTH: 816
<212> TYPE: DNA
<213> ORGANISM: Artificial Sequence
<220> FEATURE:
<223> OTHER INFORMATION: MCD111 with His Tag

<400> SEQUENCE: 17

```
atgcggggtt ctcatcatca tcatcatcat ggtatggcta gcatgactgg tggacagcaa    60
```

```
atgggtcggg atctgtacga cgatgacgat aaggatcccg ccaccatggt gagcaagggc      120
gaggaggata catggccat catcaaggag ttcatgcgct tcaaggtgca catggagggc       180
tccgtgaacg gccacgagtt cgagatcgag ggcgagggcg agggccgccc ctacgagggc      240
acccagaccg ccaagctgaa ggtgaccaag ggtggcccc tgcccttcgc ctgggacatc       300
ctgtcccctc agttcatgta cggctccaag gcctacgtga agcaccccgc cgacatcccc      360
gactacttga agctgtcctt ccccgagggc ttcaagtggg agcgcgtgat gaacttcgag      420
gacggcggcg tggtgaccgt gacccaggac tcctccctgc aggacggcga gttcatctac      480
aaggtgaagc tgcgcggcac caacttcccc tccgacggcc ccgtaatgca gaagaagacc      540
atgggctggg aggagtcctc cgagcggatg taccccgagg acggcgccct gaagggcgag      600
atcaagcaga ggctgaagct gaaggacggc ggccactacg acgctgaggt caagaccacc      660
tacaaggcca agaagcccgt gcagctgccc ggcgcctaca acgtcgagat cgagttggac      720
atcacctccc acaacgagga ctacaccatc gtggaacagt acgaagaggc cgagggcgag      780
cactccaccg gcggcatgga cgagctgtac aagtaa                               816

<210> SEQ ID NO 18
<211> LENGTH: 792
<212> TYPE: DNA
<213> ORGANISM: Artificial Sequence
<220> FEATURE:
<223> OTHER INFORMATION: MCD111 with ER Tag

<400> SEQUENCE: 18
atgctgctat ccgtgccgtt gctgctcggc ctcctcggcc tggccgctgc agacggggat       60
cccgccacca tggtgagcaa gggcgaggag ataacatgg ccatcatcaa ggagttcatg      120
cgcttcaagg tgcacatgga gggctccgtg aacggccacg agttcgagat cgagggcgag      180
ggcgagggcc gccctacga gggcacccag accgccaagc tgaaggtgac caagggtggc      240
cccctgccct cgcctggga catcctgtcc cctcagttca gtacggctc caaggcctac      300 gtgaagcacc ccgccgacat ccccgactac ttgaagctgt ccttccccga gggcttcaag      360
tgggagcgcg tgatgaactt cgaggacggc ggcgtggtga ccgtgaccca ggactcctcc      420
ctgcaggacg gcgagttcat ctacaaggtg aagctgcgcg gcaccaactt ccccctccgac     480 ggcccccgtaa tgcagaagaa gaccatgggc tgggaggagt cctccgagcg gatgtacccc     540
gaggacggcg ccctgaaggg cgagatcaag cagaggctga agctgaagga cggcggccac      600
tacgacgctg aggtcaagac cacctacaag gccaagaagc ccgtgcagct gcccggcgcc      660
tacaacgtcg agatcgagtt ggacatcacc tcccacaacg aggactacac catcgtggaa      720
cagtacgaag aggccgaggg cgagcactcc accggcggca tggacgagct gtacaagaag      780
gacgagctgt aa                                                          792

<210> SEQ ID NO 19
<211> LENGTH: 792
<212> TYPE: DNA
<213> ORGANISM: Artificial Sequence
<220> FEATURE:
<223> OTHER INFORMATION: MCD112 with ER Tag

<400> SEQUENCE: 19
atgctgctat ccgtgccgtt gctgctcggc ctcctcggcc tggccgctgc agacggggat       60
cccgccacca tggtgagcaa gggcgaggag ataacatgg ccatcatcaa ggagttcatg      120
```

| | |
|---|---|
| cgcttcaagg tgcacatgga gggctccgtg aacggccacg agttcgagat cgagggcgag | 180 |
| ggcgagggcc gcccctacga gggcacccag accgccaagc tgaaggtgac caagggtggc | 240 |
| cccctgccct cgcctggga catcctgtcc cctcagttca tgtacggctc caaggcctac | 300 |
| gtgaagcacc ccgccgacat ccccgactac ttgaagctgt ccttccccga gggcttcaag | 360 |
| tgggagcgcg tgatgaactt cgaggacggc ggcgtggtga ccgtgaccca ggactcctcc | 420 |
| ctgcaggacg gcgagttcat ctacaaggtg aagctgcgcg gcaccaactt ccctccgac | 480 |
| ggccccgtaa tgcagaagaa gaccatgggc tgggaggagt cctccgagcg gatgtacccc | 540 |
| gaggacggcg ccctgaaggg cgagatcaag cagaggctga agctgaagga cggcggccac | 600 |
| tacgacgctg aggtcaagac cacctacaag gccaagaagc ccgtgcagct gcccggcgcc | 660 |
| tacaacgtcg acatcgactt ggacatcacc tcccacaacg aggactacac catcgtggaa | 720 |
| cagtacgaag aggccgaggg ccagcactcc accggcggca tggacgagct gtacaagaag | 780 |
| gacgagctgt aa | 792 |

<210> SEQ ID NO 20
<211> LENGTH: 816
<212> TYPE: DNA
<213> ORGANISM: Artificial Sequence
<220> FEATURE:
<223> OTHER INFORMATION: MCD2 with His Tag

<400> SEQUENCE: 20

| | |
|---|---|
| atgcggggtt ctcatcatca tcatcatcat ggtatggcta gcatgactgg tggacagcaa | 60 |
| atgggtcggg atctgtacga cgatgacgat aaggatcccg ccaccatggt gagcaagggc | 120 |
| gaggaggata acatggccat catcaaggag ttcatgcgct tcaaggtgca catggagggc | 180 |
| tccgtgaacg gccacgagtt cgagatcgag ggcgagggcg agggccgccc ctacgagggc | 240 |
| acccagaccg ccaagctgaa ggtgaccaag gtggccccc tgcccttcgc ctgggacatc | 300 |
| ctgtcccctc agttcatgta cggctccaag gcctacgtga agcaccccgc cgacatcccc | 360 |
| gactacttga agctgtcctt ccccgagggc ttcaagtggg agcgcgtgat gaacttcgag | 420 |
| gacgcggcg tggtgaccgt gacccaggac tcctccctgc aggacggcga gttcatctac | 480 |
| aaggtgaagc tgcgcggcac caacttcccc tccgacggcc ccgtaatgca gaagaagacc | 540 |
| atgggctggg aggcctcctc cgagcggatg taccccgagg acggcgccct gaagggcgag | 600 |
| atcaagcaga ggctgaagct gaaggacggc ggccactacg acgctgaggt caagaccacc | 660 |
| tacaaggcca gaagcccgt gcagctgccc ggcgcctaca cgtcaacat cgacttggac | 720 |
| atcacctccc acaacgagga ctacaccatc gtggaacagg aggagaggc cgagggccgc | 780 |
| cactccaccg gcggcatgga cgagctgtac aagtaa | 816 |

<210> SEQ ID NO 21
<211> LENGTH: 816
<212> TYPE: DNA
<213> ORGANISM: Artificial Sequence
<220> FEATURE:
<223> OTHER INFORMATION: MCD22 with His Tag

<400> SEQUENCE: 21

| | |
|---|---|
| atgcggggtt ctcatcatca tcatcatcat ggtatggcta gcatgactgg tggacagcaa | 60 |
| atgggtcggg atctgtacga cgatgacgat aaggatcccg ccaccatggt gagcaagggc | 120 |
| gaggaggata acatggccat catcaaggag ttcatgcgct tcaaggtgca catggagggc | 180 |
| tccgtgaacg gccacgagtt cgagatcgag ggcgagggcg agggccgccc ctacgagggc | 240 |

```
acccagaccg ccaagctgaa ggtgaccaag ggtggccccc tgcccttcgc ctgggacatc      300
ctgtcccctc agttcatgta cggctccaag gcctacgtga agcaccccgc cgacatcccc      360
gactacttga agctgtcctt ccccgagggc ttcaagtggg agcgcgtgat gaacttcgag      420
gacggcggcg tggtgaccgt gacccaggac tcctccctgc aggacggcga gttcatctac      480
aaggtgaagc tgcgcggcac caacttcccc tccgacggcc ccgtaatgca gaagaagacc      540
atgggctggg aggcctcctc cgagcggatg taccccgagg acggcgccct gaagggcgag      600
atcaagcaga ggctgaagct gaaggacggc ggccactacg acgctgaggt caagaccacc      660
tacaaggcca gaagcccgt gcagctgccc ggcgcctaca cgtcgagat caagttggac      720 atcacctccc acaacgagga ctacaccatc gtggaacagg aggaagaggc cgagggccgc      780
cactccaccg gcggcatgga cgagctgtac aagtaa                                816

<210> SEQ ID NO 22
<211> LENGTH: 816
<212> TYPE: DNA
<213> ORGANISM: Artificial Sequence
<220> FEATURE:
<223> OTHER INFORMATION: MCD23 with His Tag

<400> SEQUENCE: 22
atgcggggtt ctcatcatca tcatcatcat ggtatggcta gcatgactgg tggacagcaa       60
atgggtcggg atctgtacga cgatgacgat aaggatcccg ccaccatggt gagcaagggc      120
gaggaggata acatggccat catcaaggag ttcatgcgct tcaaggtgca catggagggc      180
tccgtgaacg gccacgagtt cgagatcgag ggcgagggcg agggccgccc ctacgagggc      240
acccagaccg ccaagctgaa ggtgaccaag ggtggccccc tgcccttcgc ctgggacatc      300
ctgtcccctc agttcatgta cggctccaag gcctacgtga agcaccccgc cgacatcccc      360
gactacttga agctgtcctt ccccgagggc ttcaagtggg agcgcgtgat gaacttcgag      420
gacggcggcg tggtgaccgt gacccaggac tcctccctgc aggacggcga gttcatctac      480
aaggtgaagc tgcgcggcac caacttcccc tccgacggcc ccgtaatgca gaagaagacc      540
atgggctggg aggcctcctc cgagcggatg taccccgagg acggcgccct gaagggcgag      600
atcaagcaga ggctgaagct gaaggacggc ggccactacg acgctgaggt caagaccacc      660
tacaaggcca gaagcccgt gcagctgccc ggcgcctaca cgtcaacat cgacttggag      720 atcacctccc acaacgagga ctacaccatc gtggaacagg aggaagaggc cgagggccgc      780
cactccaccg gcggcatgga cgagctgtac aagtaa                                816

<210> SEQ ID NO 23
<211> LENGTH: 816
<212> TYPE: DNA
<213> ORGANISM: Artificial Sequence
<220> FEATURE:
<223> OTHER INFORMATION: MCD24 with His Tag

<400> SEQUENCE: 23
atgcggggtt ctcatcatca tcatcatcat ggtatggcta gcatgactgg tggacagcaa       60
atgggtcggg atctgtacga cgatgacgat aaggatcccg ccaccatggt gagcaagggc      120
gaggaggata acatggccat catcaaggag ttcatgcgct tcaaggtgca catggagggc      180
tccgtgaacg gccacgagtt cgagatcgag ggcgagggcg agggccgccc ctacgagggc      240
acccagaccg ccaagctgaa ggtgaccaag ggtggccccc tgcccttcgc ctgggacatc      300
```

| | |
|---|---|
| ctgtcccctc agttcatgta cggctccaag gcctacgtga agcaccccgc cgacatcccc | 360 |
| gactacttga agctgtcctt ccccgagggc ttcaagtggg agcgcgtgat gaacttcgag | 420 |
| gacggcggcg tggtgaccgt gacccaggac tcctccctgc aggacggcga gttcatctac | 480 |
| aaggtgaagc tgcgcggcac caacttcccc tccgacggcc ccgtaatgca gaagaagacc | 540 |
| atgggctggg aggcctcctc cgagcggatg taccccgagg acggcgccct gaagggcgag | 600 |
| atcaagcaga ggctgaagct gaaggacggc ggccactacg acgctgaggt caagaccacc | 660 |
| tacaaggcca agaagcccgt gcagctgccc ggcgcctaca cgtcaacat cgacttgcag | 720 |
| atcacctccc acaacgagga ctacaccatc gtggaacagg aggaagaggc cgagggccgc | 780 |
| cactccaccg gcggcatgga cgagctgtac aagtaa | 816 |

<210> SEQ ID NO 24
<211> LENGTH: 816
<212> TYPE: DNA
<213> ORGANISM: Artificial Sequence
<220> FEATURE:
<223> OTHER INFORMATION: MCD25 with His Tag

<400> SEQUENCE: 24

| | |
|---|---|
| atgcggggtt ctcatcatca tcatcatcat ggtatggcta gcatgactgg tggacagcaa | 60 |
| atgggtcggg atctgtacga cgatgacgat aaggatcccg ccaccatggt gagcaagggc | 120 |
| gaggaggata acatggccat catcaaggag ttcatgcgct tcaaggtgca catggagggc | 180 |
| tccgtgaacg gccacgagtt cgagatcgag ggcgagggcg agggccgccc ctacgagggc | 240 |
| acccagaccg ccaagctgaa ggtgaccaag gtggccccc tgcccttcgc ctgggacatc | 300 |
| ctgtcccctc agttcatgta cggctccaag gcctacgtga agcaccccgc cgacatcccc | 360 |
| gactacttga agctgtcctt ccccgagggc ttcaagtggg agcgcgtgat gaacttcgag | 420 |
| gacggcggcg tggtgaccgt gacccaggac tcctccctgc aggacggcga gttcatctac | 480 |
| aaggtgaagc tgcgcggcac caacttcccc tccgacggcc ccgtaatgca gaagaagacc | 540 |
| atgggctggg aggcctcctc cgagcggatg taccccgagg acggcgccct gaagggcgag | 600 |
| atcaagcaga ggctgaagct gaaggacggc ggccactacg acgctgaggt caagaccacc | 660 |
| tacaaggcca agaagcccgt gcagctgccc ggcgcctaca cgtcaacat cgacttgaac | 720 |
| atcacctccc acaacgagga ctacaccatc gtggaacagg aggaagaggc cgagggccgc | 780 |
| cactccaccg gcggcatgga cgagctgtac aagtaa | 816 |

<210> SEQ ID NO 25
<211> LENGTH: 816
<212> TYPE: DNA
<213> ORGANISM: Artificial Sequence
<220> FEATURE:
<223> OTHER INFORMATION: MCD26 with His Tag

<400> SEQUENCE: 25

| | |
|---|---|
| atgcggggtt ctcatcatca tcatcatcat ggtatggcta gcatgactgg tggacagcaa | 60 |
| atgggtcggg atctgtacga cgatgacgat aaggatcccg ccaccatggt gagcaagggc | 120 |
| gaggaggata acatggccat catcaaggag ttcatgcgct tcaaggtgca catggagggc | 180 |
| tccgtgaacg gccacgagtt cgagatcgag ggcgagggcg agggccgccc ctacgagggc | 240 |
| acccagaccg ccaagctgaa ggtgaccaag gtggccccc tgcccttcgc ctgggacatc | 300 |
| ctgtcccctc agttcatgta cggctccaag gcctacgtga agcaccccgc cgacatcccc | 360 |
| gactacttga agctgtcctt ccccgagggc ttcaagtggg agcgcgtgat gaacttcgag | 420 |

```
gacggcggcg tggtgaccgt gacccaggac tcctccctgc aggacggcga gttcatctac    480
aaggtgaagc tgcgcggcac caacttcccc tccgacggcc ccgtaatgca agaagaagacc   540 atgggctggg aggcctcctc cgagcggatg taccccgagg acggcgccct gaagggcgag    600
atcaagcaga ggctgaagct gaaggacggc ggccactacg acgctgaggt caagaccacc    660
tacaaggcca agaagcccgt gcagctgccc ggcgcctaca acgtcaacat cgacttggac    720
atcacctccc acaacgagga ctacaccatc gtggaacagg aggaagacgc cgagggccgc    780
cactccaccg gcggcatgga cgagctgtac aagtaa                              816
```

<210> SEQ ID NO 26
<211> LENGTH: 816
<212> TYPE: DNA
<213> ORGANISM: Artificial Sequence
<220> FEATURE:
<223> OTHER INFORMATION: mcEE with His Tag
<400> SEQUENCE: 26

```
atgcggggtt ctcatcatca tcatcatcat ggtatggcta gcatgactgg tggacagcaa    60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg gccacgagtt cgagatcgag ggcgagggcg agggccgccc ctacgagggc    240
acccagaccg ccaagctgaa ggtgaccaag ggtggccccc tgcccttcgc ctgggacatc    300
ctgtcccctc agttcatgta cggctccaag gcctacgtga agcacccgc cgacatcccc    360 gactacttga agctgtcctt ccccgagggc ttcaagtggg agcgcgtgat gaacttcgag    420
gacggcggcg tggtgaccgt gacccaggac tcctccctgc aggacggcga gttcatctac    480
aaggtgaagc tgcgcggcac caacttcccc tccgacggcc ccgtaatgca agaagaagacc   540 atgggctggg aggcctcctc cgagcggatg taccccgagg acggcgccct gaagggcgag    600
atcaagcagg agctggagct gaaggacggc ggccactacg acgctgaggt caagaccacc    660
tacaaggcca agaagcccgt gcagctgccc ggcgcctaca acgtcaacat caagttggac    720
atcacctccc acaacgagga ctacaccatc gtggaacagt acgaacgcgc cgagggccgc    780
cactccaccg gcggcatgga cgagctgtac aagtaa                              816
```

<210> SEQ ID NO 27
<211> LENGTH: 792
<212> TYPE: DNA
<213> ORGANISM: Artificial Sequence
<220> FEATURE:
<223> OTHER INFORMATION: mcP4 with ER Tag
<400> SEQUENCE: 27

```
atgctgctat ccgtgccgtt gctgctcggc ctcctcggcc tggccgctgc agacggggat    60
cccgccacca tggtgagcaa gggcgaggag ataacatgg ccatcatcaa ggagttcatg    120
cgcttcaagg tgcacatgga gggctccgtg aacggccacg agttcgagat cgagggcgag    180
ggcgagggcc gcccctacga gggcacccag accgccaagc tgaaggtgac caagggtggc    240
cccctgccct tcgcctggga catcctgtcc cctcagttca tgtacggctc caaggcctac    300
gtgaagcacc ccgccgacat ccccgactac ttgaagctgt ccttccccga gggcttcaag    360
tgggagcgcg tgatgaactt cgaggacggc ggcgtggtga ccgtgaccca ggactcctcc    420
ctgcaggacg gcgagttcat ctacaaggtg aagctgcgcg gcaccaactt cccctccgac    480
```

| | |
|---|---|
| ggccccgtaa tgcagaagaa gaccatggag tgggaggcct cctccgagcg gatgtacccc | 540 |
| gaggacggcg ccctgaaggg cgagatcaag caggagctgg agctgaagga cggcggccac | 600 |
| tacgacgctg aggtcaagac cacctacaag gccaagaagc ccgtgcagct gcccggcgcc | 660 |
| tacaacgtca acatcaagtt ggacatcacc tcccacaacg aggactacac catcgtggaa | 720 |
| cagtacgaac gcgccgaggg ccgccactcc accggcggca tggacgagct gtacaagaag | 780 |
| gacgagctgt aa | 792 |

<210> SEQ ID NO 28
<211> LENGTH: 816
<212> TYPE: DNA
<213> ORGANISM: Artificial Sequence
<220> FEATURE:
<223> OTHER INFORMATION: mcP4 with His Tag

<400> SEQUENCE: 28

| | |
|---|---|
| atgcggggtt ctcatcatca tcatcatcat ggtatggcta gcatgactgg tggacagcaa | 60 |
| atgggtcggg atctgtacga cgatgacgat aaggatcccg ccaccatggt gagcaagggc | 120 |
| gaggaggata acatggccat catcaaggag ttcatgcgct tcaaggtgca catggagggc | 180 |
| tccgtgaacg gccacgagtt cgagatcgag ggcgagggcg agggccgccc ctacgagggc | 240 |
| acccagaccg ccaagctgaa ggtgaccaag ggtggccccc tgcccttcgc ctgggacatc | 300 |
| ctgtcccctc agttcatgta cggctccaag gcctacgtga agcaccccgc cgacatcccc | 360 |
| gactacttga gctgtccttc cccgagggc ttcaagtggg agcgcgtgat gaacttcgag | 420 |
| gacggcggcg tggtgaccgt gacccaggac tcctccctgc aggacggcga gttcatctac | 480 |
| aaggtgaagc tgcgcggcac caacttcccc tccgacggcc ccgtaatgca gaagaagacc | 540 |
| atggagtggg aggcctcctc cgagcggatg taccccgagg acggcgccct gaagggcgag | 600 |
| atcaagcagg agctggagct gaaggacggc ggccactacg acgctgaggt caagaccacc | 660 |
| tacaaggcca gaagcccgt gcagctgccc ggcgcctaca cgtcaacat caagttggac | 720 |
| atcacctccc acaacgagga ctacaccatc gtggaacagt acgaacgcgc cgagggccgc | 780 |
| cactccaccg gcggcatgga cgagctgtac aagtaa | 816 |

<210> SEQ ID NO 29
<211> LENGTH: 792
<212> TYPE: DNA
<213> ORGANISM: Artificial Sequence
<220> FEATURE:
<223> OTHER INFORMATION: mcP5 with ER Tag

<400> SEQUENCE: 29

| | |
|---|---|
| atgctgctat ccgtgccgtt gctgctcggc ctcctcggcc tggccgctgc agacgggat | 60 |
| cccgccacca tggtgagcaa gggcgaggag ataacatgg ccatcatcaa ggagttcatg | 120 |
| cgcttcaagg tgcacatgga gggctccgtg aacggccacg agttcgagat cgagggcgag | 180 |
| ggcgagggcc gcccctacga gggcacccag accgccaagc tgaaggtgac caagggtggc | 240 |
| cccctgccct tcgcctggga catcctgtcc cctcagttca tgtacggctc caaggcctac | 300 |
| gtgaagcacc ccgccgacat ccccgactac ttgaagctgt ccttccccga gggcttcaag | 360 |
| tgggagcgcg tgatgaactt cgaggacggc ggcgtggtga ccgtgaccca ggactcctcc | 420 |
| ctgcaggacg cgagttcat ctacaaggtg aagctgcgcg gcaccaactt cccctccgac | 480 |
| ggccccgtaa tgcagaagaa gaccatgggc tgggaggcct cctccgagcg gatgtacccc | 540 |
| gaggacggcg ccctgaaggg cgagatcaag caggagctgg agctgaagga cggcggcgag | 600 |

```
tacgacgctg aggtcaagac cacctacaag gccaagaagc ccgtgcagct gcccggcgcc    660
tacaacgtca acatcaagtt ggacatcacc tcccacaacg aggactacac catcgtggaa    720
cagtacgaac gcgccgaggg ccgccactcc accggcggca tggacgagct gtacaagaag    780
gacgagctgt aa                                                       792
```

<210> SEQ ID NO 30
<211> LENGTH: 816
<212> TYPE: DNA
<213> ORGANISM: Artificial Sequence
<220> FEATURE:
<223> OTHER INFORMATION: mcP5 with His Tag

<400> SEQUENCE: 30

```
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg gccacgagtt cgagatcgag ggcgagggcg agggccgccc ctacgagggc    240
acccagaccg ccaagctgaa ggtgaccaag ggtggccccc tgcccttcgc ctgggacatc    300
ctgtcccctc agttcatgta cggctccaag gcctacgtga agcaccccgc cgacatcccc    360
gactacttga gctgtccttc cccgagggc ttcaagtggg agcgcgtgat gaacttcgag    420
gacggcggcg tggtgaccgt gacccaggac tcctccctgc aggacggcga gttcatctac    480
aaggtgaagc tgcgcggcac caacttcccc tccgacggcc ccgtaatgca gaagaagacc    540
atgggctggg aggcctcctc cgagcggatg taccccgagg acggcgccct gaagggcgag    600
atcaagcagg agctggagct gaaggacggc ggcgagtacg acgctgaggt caagaccacc    660
tacaaggcca gaagcccgt gcagctgccc ggcgcctaca acgtcaacat caagttggac    720
atcacctccc acaacgagga ctacaccatc gtggaacagt acgaacgcgc cgagggccgc    780
cactccaccg gcggcatgga cgagctgtac aagtaa                             816
```

<210> SEQ ID NO 31
<211> LENGTH: 816
<212> TYPE: DNA
<213> ORGANISM: Artificial Sequence
<220> FEATURE:
<223> OTHER INFORMATION: mcP6 with His Tag

<400> SEQUENCE: 31

```
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg gccacgagtt cgagatcgag ggcgagggcg agggccgccc ctacgagggc    240
acccagaccg ccaagctgaa ggtgaccaag ggtggccccc tgcccttcgc ctgggacatc    300
ctgtcccctc agttcatgta cggctccaag gcctacgtga agcaccccgc cgacatcccc    360
gactacttga gctgtccttc cccgagggc ttcgagtggg agcgcgtgat gaacttcgag    420
gacggcggcg tggtgaccgt ggagcaggac tcctccctgc aggacggcga gttcatctac    480
aaggtgaagc tgcgcggcac caacttcccc tccgacggcc ccgtaatgca gaagaagacc    540
atgggctggg aggcctcctc cgagcggatg taccccgagg acggcgccct gaagggcgag    600
atcaagcaga ggctgaagct gaaggacggc ggccactacg acgctgaggt caagaccacc    660
```

```
tacaaggcca agaagcccgt gcagctgccc ggcgcctaca acgtcaacat caagttggac    720
atcacctccc acaacgagga ctacaccatc gtggaacagt acgaacgcgc cgagggccgc    780
cactccaccg gcggcatgga cgagctgtac aagtaa                              816
```

<210> SEQ ID NO 32
<211> LENGTH: 903
<212> TYPE: DNA
<213> ORGANISM: Artificial Sequence
<220> FEATURE:
<223> OTHER INFORMATION: MCIN1 with His Tag

<400> SEQUENCE: 32

```
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg gccacgagtt cgagatcgag ggcgagggcg agggccgccc ctacgagggc    240
acccagaccg ccaagctgaa ggtgaccaag ggtggccccc tgcccttcgc ctgggacatc    300
ctgtcccctc agttcatgta cggctccaag gcctacgtga agcaccccgc cgacatcccc    360
gactacttga agctgtcctt ccccgagggc ttcaagtggg agcgcgtgat gaacttcgag    420
gacggcggcg tggtgaccgt gacccaggac tcctccctgc aggacggcga gttcatctac    480
aaggtgaagc tgcgcggcac caacttcccc tccgacggcc ccgtaatgca gaagaagacc    540
atgggctggg aggcctcctc cgagcggatg taccccgaga ccctagatga gctctttgag    600
gaactggata agaatggcga tgcgaagtg agctttgaag aattccaagt attagtaaaa     660
aagatagacg gcgccctgaa gggcgagatc aagcagaggc tgaagctgaa ggacggcggc    720
cactacgacg ctgaggtcaa gaccacctac aaggccaaga agcccgtgca gctgcccggc    780
gcctacaacg tcaacatcaa gttggacatc acctcccaca cgaggactac accatcgtg    840 gaacagtacg aacgcgccga gggccgccac tccaccggcg gcatggacga gctgtacaag    900
taa                                                                  903
```

<210> SEQ ID NO 33
<211> LENGTH: 885
<212> TYPE: DNA
<213> ORGANISM: Artificial Sequence
<220> FEATURE:
<223> OTHER INFORMATION: MCIN2 with His Tag
<220> FEATURE:
<221> NAME/KEY: misc_feature
<222> LOCATION: (231)..(231)
<223> OTHER INFORMATION: n is a, c, g, or t

<400> SEQUENCE: 33

```
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg gccacgagtt cgagatcgag ggcgagggcg agggccgccc ntacgagggc    240
acccagaccg ccaagctgaa ggtgaccaag ggtggccccc tgcccttcgc ctgggacatc    300
ctgtcccctc agttcatgta cggctccaag gcctacgtga agcaccccgc cgacatcccc    360
gactacttga agctgtcctt ccccgagggc ttcaagtggg agcgcgtgat gaacttcgag    420
dacggcggcg tggtgaccgt gacccaggac tcctccctgc aggacggcga gttcatctac    480
aaggtgaagc tgcgcggcac caacttcccc tccgacggcc ccgtaaccct agatgagctc    540
```

```
tttgaggaac tggataagaa tggcgatggc gaagtgagct ttgaagaatt ccaagtatta    600
gtaaaaaaga taggctggga ggcctcctcc gagcggatgt accccgagga cggcgccctg    660
aagggcgaga tcaagcagag gctgaagctg aaggacggcg ccactacga cgctgaggtc    720 aagaccacct acaaggccaa gaagcccgtg cagctgcccg cgcctacaa cgtcaacatc     780 aagttggaca tcacctccca caacgaggac tacaccatcg tggaacagta cgaacgcgcc    840
gagggccgcc actccaccgg cggcatggac gagctgtaca agtaa                    885
```

<210> SEQ ID NO 34
<211> LENGTH: 891
<212> TYPE: DNA
<213> ORGANISM: Artificial Sequence
<220> FEATURE:
<223> OTHER INFORMATION: MCIN3 with His Tag

<400> SEQUENCE: 34

```
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg ccacgagtt cgagatcgag ggcgagggcg agggccgccc ctacgagggc     240
acccagaccg ccaagctgaa ggtgaccaag ggtggccccc tgcccttcgc ctgggacatc    300
ctgtcccctc agttcatgta cggctccaag gcctacgtga agcaccccgc cgacatcccc    360
gactacttga agctgtcctt ccccgagggc ttcaagtggg agcgcgtgat gaacttcgag    420
gacggcggcg tggtgaccgt gacccaggac tcctccctgc aggacggcga gttcatctac    480
aaggtgaagc tgcgcggcac caacttcccc tccgacggcc ccgtaatgca gaagaagacc    540
atgggcaccc tagatgagct ctttgaggaa ctggataaga atggcgatgg cgaagtgagc    600
tttgaagaat tccaagtatt agtaaaaaag atatccgagc ggatgtaccc cgaggacggc    660
gccctgaagg gcgagatcaa gcagaggctg aagctgaagg acgcggcca ctacgacgct    720 gaggtcaaga ccacctacaa ggccaagaag cccgtgcagc tgcccggcgc ctacaacgtc    780
aacatcaagt tggacatcac ctcccacaac gaggactaca ccatcgtgga acagtacgaa    840
cgcgccgagg ccgccactc caccggcggc atggacgagc tgtacaagta a              891
```

<210> SEQ ID NO 35
<211> LENGTH: 867
<212> TYPE: DNA
<213> ORGANISM: Artificial Sequence
<220> FEATURE:
<223> OTHER INFORMATION: MCIN3 with ER Tag
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t

<400> SEQUENCE: 35

```
atgctgctat ccgtgccgtt gctgctcggc ctcctcggcc tggccgctgc agacggggat     60
cccgccacca tggtgagcaa gggcgaggag gataacatgg ccatcatcaa ggagttcatg    120
cgcttcaagg tgcacatgga gggctccgtg aacggcacg agttcgagat cgagggcgag     180
ggcgagggcc gcccctacga gggcacccag accgccaagc tgaaggtgac caagggtggc    240
```

```
cccctgccct tcgcctggga catcctgtcc cctcagttca tgtacggctc caaggcctac    300
gtgaagcacc ccgccgacat ccccgactac ttgaagctgt ccttccccga gggcttcaag    360
tgggagcgcg tgatgaactt cgaggacggc ggcgtggtga ccgtgaccca ggactcctcc    420
ctgcaggacg gcgagttcat ctacaaggtg aagctgcgcg gcaccaactt ccctccggac    480
ggccccgtaa tgcagaagaa gaccatgggc accctagatg agctctttga ggaactggat    540
aagaatggcg atggcgaagt gagctttgaa gaattccaag tattagtaaa aaagatatcc    600
gagcggatgt accccgagga cggcgccctg aagggcgaga tcaagcagag gctgaagctg    660
aaggacggcg ccactacga cgctgangtc aagaccacct acaaggccaa gaagcccgtg    720
cagctgcccg cgcctacaa cgtcaacatc aagttggaca tcacctccca caacgaggac    780
tacaccatcg tggaacagta cgaacgcgcc ganggccgcc actccaccgg cggcatggac    840
gagctgtaca agaaggacga gctgtaa                                       867

<210> SEQ ID NO 36
<211> LENGTH: 828
<212> TYPE: DNA
<213> ORGANISM: Artificial Sequence
<220> FEATURE:
<223> OTHER INFORMATION: MCIN4 with His Tag

<400> SEQUENCE: 36
atgcggggtt ctcatcatca tcatcatcat ggtatggcta gcatgactgg tggacagcaa     60
atgggtcggg atctgtacga cgatgacgat aaggatcccg ccaccatggt gagcaagggc    120
gaggaggata acatggccat catcaaggag ttcatgcgct tcaaggtgca catggagggc    180
tccgtgaacg gccacgagtt cgagatcgag ggcgagggcg agggccgccc ctacgagggc    240
acccagaccg ccaagctgaa ggtgaccaag ggtggccccc tgcccttcgc ctgggacatc    300 ctgtccccctc agttcatgta cggctccaag gcctacgtga agcaccccgc cgacatcccc    360
gactacttga gctgtccttt ccccgagggc ttcaagtggg agcgcgtgat gaacttcgag    420
gacggcggcg tggtgaccgt gacccaggac tcctccctgc aggacggcga gttcatctac    480
aaggtgaagc tgcgcggcac caacttcccc tccgacggcc ccgtaatgca agaagaagacc    540 atgggctggg ataagaatgg cgatggcgaa gtcgagcgga tgtaccccga ggacggcgcc    600
ctgaagggcg agatcaagca gaggctgaag ctgaaggacg gcggccacta cgacgctgag    660
gtcaagacca cctacaaggc caagaagccc gtgcagctgc ccggcgccta caacgtcaac    720
atcaagttgg acatcacctc ccacaacgag gactacacca tcgtggaaca gtacgaacgc    780
gccgagggcc gccactccac cggcggcatg gacgagctgt acaagtaa                828

<210> SEQ ID NO 37
<211> LENGTH: 238
<212> TYPE: PRT
<213> ORGANISM: Artificial Sequence
<220> FEATURE:
<223> OTHER INFORMATION: CatchER

<400> SEQUENCE: 37

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

```
Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
            195                 200                 205

Lys Asp Pro Asn Glu Lys Arg Asp His Ile Val Leu Leu Glu Glu Val
210                 215                 220

Glu Ala Ala Gly Ile Thr Leu Gly Met Asp Glu Leu Tyr Lys
225                 230                 235

<210> SEQ ID NO 38
<211> LENGTH: 260
<212> TYPE: PRT
<213> ORGANISM: Artificial Sequence
<220> FEATURE:
<223> OTHER INFORMATION: CatchER Tag

<400> SEQUENCE: 38

Met Leu Leu Ser Val Pro Leu Leu Gly Leu Leu Gly Leu Ala Ala
 1               5                  10                  15

Ala Asp Val Ser Lys Gly Glu Glu Leu Phe Thr Gly Val Val Pro Ile
             20                  25                  30

Leu Val Glu Leu Asp Gly Asp Leu Asn Gly His Lys Phe Ser Val Ser
         35                  40                  45

Gly Glu Gly Glu Gly Asp Ala Thr Tyr Gly Lys Leu Thr Leu Lys Phe
     50                  55                  60

Ile Cys Thr Thr Gly Lys Leu Pro Val Pro Trp Pro Thr Leu Val Thr
 65                  70                  75                  80

Thr Leu Thr Tyr Gly Val Gln Cys Phe Ser Arg Tyr Pro Asp His Met
                 85                  90                  95

Lys Gln His Asp Phe Phe Lys Ser Ala Met Pro Glu Gly Tyr Val Gln
                100                 105                 110

Glu Arg Thr Ile Phe Phe Lys Asp Asp Gly Asn Tyr Lys Thr Arg Ala
            115                 120                 125

Glu Val Lys Phe Glu Gly Asp Thr Leu Val Asn Arg Ile Glu Leu Lys
130                 135                 140

Gly Ile Asp Phe Lys Glu Asp Gly Asn Ile Leu Gly His Lys Leu Glu
145                 150                 155                 160

Tyr Asn Tyr Asn Glu His Asn Val Tyr Ile Thr Ala Asp Lys Gln Lys
                165                 170                 175
```

```
Asn Gly Ile Lys Ala Asn Phe Lys Ile Arg His Asn Ile Glu Asp Gly
            180                 185                 190

Ser Val Gln Leu Ala Asp His Tyr Gln Gln Asn Thr Pro Ile Gly Asp
        195                 200                 205

Gly Pro Val Leu Leu Pro Asp Asn His Tyr Leu Asp Thr Glu Ser Ala
    210                 215                 220

Leu Ser Lys Asp Pro Asn Glu Lys Arg Asp His Ile Val Leu Leu Glu
225                 230                 235                 240

Glu Val Glu Ala Ala Gly Ile Thr Leu Gly Met Asp Glu Leu Tyr Lys
                245                 250                 255

Lys Asp Glu Leu
            260
```

<210> SEQ ID NO 39
<211> LENGTH: 267
<212> TYPE: PRT
<213> ORGANISM: Artificial Sequence
<220> FEATURE:
<223> OTHER INFORMATION: CatchER-T

<400> SEQUENCE: 39

```
Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
                20                  25                  30

Phe Thr Gly Val Val Pro Ile Leu Val Glu Leu Asp Gly Asp Val Asn
                35                  40                  45

Gly His Lys Phe Ser Val Ser Gly Glu Gly Glu Gly Asp Ala Thr Tyr
            50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
                100                 105                 110

Met Pro Glu Gly Tyr Val Gln Glu Arg Thr Ile Phe Phe Lys Asp Asp
            115                 120                 125

Gly Asn Tyr Lys Thr Arg Ala Glu Val Lys Phe Glu Gly Asp Thr Leu
130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Glu His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Gly Val Gln Leu Ala Asp His Tyr Gln
            195                 200                 205

Gln Asn Thr Pro Ile Gly Asp Gly Pro Val Leu Leu Pro Asp Asn His
        210                 215                 220

Tyr Leu Asp Thr Glu Ser Ala Leu Ser Lys Asp Pro Asn Glu Lys Arg
225                 230                 235                 240

Asp His Met Val Leu Leu Glu Glu Val Glu Ala Ala Gly Ile Thr Leu
                245                 250                 255

Gly Met Asp Glu Leu Tyr Lys Lys Asp Glu Leu
            260                 265
```

<210> SEQ ID NO 40
<211> LENGTH: 238
<212> TYPE: PRT
<213> ORGANISM: Artificial Sequence
<220> FEATURE:
<223> OTHER INFORMATION: MCherry

<400> SEQUENCE: 40

```
Met Val Ser Lys Gly Glu Glu Asp Asn Met Ala Ile Ile Lys Glu Phe
1               5                  10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Lys Leu Asp Ile
        195                 200                 205

Thr Ser His Asn Glu Asp Tyr Thr Ile Val Glu Gln Tyr Glu Arg Ala
    210                 215                 220

Glu Gly Arg His Ser Thr Gly Gly Met Asp Glu Leu Tyr Lys
225                 230                 235
```

<210> SEQ ID NO 41
<211> LENGTH: 242
<212> TYPE: PRT
<213> ORGANISM: Artificial Sequence
<220> FEATURE:
<223> OTHER INFORMATION: MCD1er

<400> SEQUENCE: 41

```
Met Val Ser Lys Gly Glu Glu Asp Asn Met Ala Ile Ile Lys Glu Phe
1               5                  10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80
```

Lys His Pro Ala Asp Ile Pro Asp Tyr Leu Lys Leu Ser Phe Pro Glu
                85                  90                  95

Gly Phe Lys Trp Glu Arg Val Met Asn Phe Asp Gly Gly Val Val
            100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Asp Leu Asp Ile
            195                 200                 205

Thr Ser His Asn Glu Asp Tyr Thr Ile Val Glu Gln Tyr Glu Glu Ala
            210                 215                 220

Glu Gly Arg His Ser Thr Gly Gly Met Asp Glu Leu Tyr Lys Lys Asp
225                 230                 235                 240

Glu Leu

<210> SEQ ID NO 42
<211> LENGTH: 242
<212> TYPE: PRT
<213> ORGANISM: Artificial Sequence
<220> FEATURE:
<223> OTHER INFORMATION: MCD15er

<400> SEQUENCE: 42

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
        50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

```
Pro Val Gln Leu Pro Gly Ala Tyr Asn Val Asp Ile Glu Leu Asp Ile
            195                 200                 205

Thr Ser His Asn Glu Asp Tyr Thr Ile Val Glu Gln Tyr Glu Glu Ala
    210                 215                 220

Glu Gly Glu His Ser Thr Gly Gly Met Asp Glu Leu Tyr Lys Lys Asp
225                 230                 235                 240

Glu Leu

<210> SEQ ID NO 43
<211> LENGTH: 238
<212> TYPE: PRT
<213> ORGANISM: Artificial Sequence
<220> FEATURE:
<223> OTHER INFORMATION: MCD1

<400> SEQUENCE: 43

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Asp Leu Asp Ile
        195                 200                 205

Thr Ser His Asn Glu Asp Tyr Thr Ile Val Glu Gln Tyr Glu Glu Ala
    210                 215                 220

Glu Gly Arg His Ser Thr Gly Gly Met Asp Glu Leu Tyr Lys
225                 230                 235

<210> SEQ ID NO 44
<211> LENGTH: 238
<212> TYPE: PRT
<213> ORGANISM: Artificial Sequence
<220> FEATURE:
<223> OTHER INFORMATION: MCD14

<400> SEQUENCE: 44

Met Val Ser Lys Gly Glu Glu Asp Asn Met Ala Ile Ile Lys Glu Phe
1               5                   10                  15
```

Met Arg Phe Lys Val His Met Glu Gly Ser Val Asn Gly His Glu Phe
        20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
 50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
130                 135                 140

Lys Lys Thr Met Gly Trp Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Asp Leu Asp Ile
        195                 200                 205

Thr Ser His Asn Glu Asp Tyr Thr Ile Val Glu Gln Tyr Glu Glu Ala
210                 215                 220

Glu Gly Glu His Ser Thr Gly Gly Met Asp Glu Leu Tyr Lys
225                 230                 235

<210> SEQ ID NO 45
<211> LENGTH: 238
<212> TYPE: PRT
<213> ORGANISM: Artificial Sequence
<220> FEATURE:
<223> OTHER INFORMATION: MCD15

<400> SEQUENCE: 45

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
 50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
130                 135                 140

```
Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Glu Leu Asp Ile
        195                 200                 205

Thr Ser His Asn Glu Asp Tyr Thr Ile Val Glu Gln Tyr Glu Glu Ala
    210                 215                 220

Glu Gly Glu His Ser Thr Gly Gly Met Asp Glu Leu Tyr Lys
225                 230                 235

<210> SEQ ID NO 46
<211> LENGTH: 238
<212> TYPE: PRT
<213> ORGANISM: Artificial Sequence
<220> FEATURE:
<223> OTHER INFORMATION: MCD2

<400> SEQUENCE: 46

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Glu Leu Asp Ile
        195                 200                 205

Thr Ser His Asn Glu Asp Tyr Thr Ile Val Glu Gln Glu Glu Glu Ala
    210                 215                 220

Glu Gly Arg His Ser Thr Gly Gly Met Asp Glu Leu Tyr Lys
225                 230                 235

<210> SEQ ID NO 47
<211> LENGTH: 238
<212> TYPE: PRT
<213> ORGANISM: Artificial Sequence
<220> FEATURE:
```

<223> OTHER INFORMATION: MCP5

<400> SEQUENCE: 47

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Glu Leu Glu Leu Lys Asp
                165                 170                 175

Gly Gly Glu Tyr Asp Ala Glu Val Lys Thr Thr Tyr Lys Ala Lys Lys
            180                 185                 190

Pro Val Gln Leu Pro Gly Ala Tyr Asn Val Asn Ile Lys Leu Asp Ile
        195                 200                 205

Thr Ser His Asn Glu Asp Tyr Thr Ile Val Glu Gln Tyr Glu Arg Ala
    210                 215                 220

Glu Gly Arg His Ser Thr Gly Gly Met Asp Glu Leu Tyr Lys
225                 230                 235

<210> SEQ ID NO 48
<211> LENGTH: 238
<212> TYPE: PRT
<213> ORGANISM: Artificial Sequence
<220> FEATURE:
<223> OTHER INFORMATION: MCP6

<400> SEQUENCE: 48

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Glu Trp Glu Arg Val Met Asn Phe Glu Asp Gly Gly Val Val
            100                 105                 110

```
Thr Val Glu Gln Asp Ser Ser Leu Gln Asp Gly Phe Ile Tyr Lys
        115                 120                 125

Val Lys Leu Arg Gly Thr Asn Phe Pro Ser Asp Gly Pro Val Met Gln
130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Lys Leu Asp Ile
        195                 200                 205

Thr Ser His Asn Glu Asp Tyr Thr Ile Val Glu Gln Tyr Glu Arg Ala
    210                 215                 220

Glu Gly Arg His Ser Thr Gly Gly Met Asp Glu Leu Tyr Lys
225                 230                 235

<210> SEQ ID NO 49
<211> LENGTH: 238
<212> TYPE: PRT
<213> ORGANISM: Artificial Sequence
<220> FEATURE:
<223> OTHER INFORMATION: MCD14Y

<400> SEQUENCE: 49

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
        50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Tyr Asp Leu Asp Ile
        195                 200                 205

Thr Ser His Asn Glu Asp Tyr Thr Ile Val Glu Gln Tyr Glu Glu Ala
    210                 215                 220

Glu Gly Glu His Ser Thr Gly Gly Met Asp Glu Leu Tyr Lys
225                 230                 235
```

<210> SEQ ID NO 50
<211> LENGTH: 238
<212> TYPE: PRT
<213> ORGANISM: Artificial Sequence
<220> FEATURE:
<223> OTHER INFORMATION: MCD14YS

<400> SEQUENCE: 50

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Tyr Asp Ser Asp Ile
        195                 200                 205

Thr Ser His Asn Glu Asp Tyr Thr Ile Val Glu Gln Tyr Glu Glu Ala
    210                 215                 220

Glu Gly Glu His Ser Thr Gly Gly Met Asp Glu Leu Tyr Lys
225                 230                 235
```

<210> SEQ ID NO 51
<211> LENGTH: 238
<212> TYPE: PRT
<213> ORGANISM: Artificial Sequence
<220> FEATURE:
<223> OTHER INFORMATION: MCD16

<400> SEQUENCE: 51

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
```

```
                 65                  70                  75                  80
Lys His Pro Ala Asp Ile Pro Asp Tyr Leu Lys Leu Ser Phe Pro Glu
                     85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Glu Ser Asp Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Asp Leu Asp Ile
        195                 200                 205

Thr Ser His Asn Glu Asp Tyr Thr Ile Val Glu Gln Tyr Glu Glu Ala
    210                 215                 220

Glu Gly Glu His Ser Thr Gly Gly Met Asp Glu Leu Tyr Lys
225                 230                 235

<210> SEQ ID NO 52
<211> LENGTH: 238
<212> TYPE: PRT
<213> ORGANISM: Artificial Sequence
<220> FEATURE:
<223> OTHER INFORMATION: MCD17

<400> SEQUENCE: 52

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Glu Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Thr Glu Ser Ala Ile
```

```
              195                 200                 205
Thr Ser His Asn Glu Asp Tyr Thr Ile Val Glu Gln Tyr Glu Glu Ala
    210                 215                 220
Glu Gly Glu His Ser Thr Gly Gly Met Asp Glu Leu Tyr Lys
225                 230                 235

<210> SEQ ID NO 53
<211> LENGTH: 238
<212> TYPE: PRT
<213> ORGANISM: Artificial Sequence
<220> FEATURE:
<223> OTHER INFORMATION: MCD18

<400> SEQUENCE: 53

Met Val Ser Lys Gly Glu Glu Asp Asn Met Ala Ile Ile Lys Glu Phe
1               5                  10                  15
Met Arg Phe Lys Val His Met Glu Gly Ser Val Asn Gly His Glu Phe
                20                  25                  30
Glu Ile Glu Gly Glu Gly Glu Gly Glu Gly Arg Pro Tyr Glu Gly Thr
            35                  40                  45
Gln Thr Ala Lys Leu Lys Val Thr Lys Gly Gly Pro Leu Pro Phe Ala
        50                  55                  60
Trp Asp Ile Leu Ser Pro Gln Phe Met Tyr Gly Ser Lys Ala Tyr Val
65                  70                  75                  80
Lys His Pro Ala Asp Ile Pro Asp Tyr Leu Lys Leu Ser Phe Pro Glu
                85                  90                  95
Gly Phe Lys Trp Glu Arg Val Met Asn Phe Glu Asp Gly Gly Val Val
            100                 105                 110
Thr Val Thr Gln Asp Ser Ser Leu Gln Asp Gly Glu Phe Ile Tyr Lys
        115                 120                 125
Val Lys Leu Arg Gly Thr Asn Phe Pro Ser Asp Gly Pro Val Met Gln
130                 135                 140
Lys Lys Thr Met Gly Trp Glu Glu Ser Ser Glu Arg Met Tyr Pro Glu
145                 150                 155                 160
Asp Gly Ala Leu Lys Gly Glu Ile Lys Gln Arg Leu Lys Leu Lys Asp
                165                 170                 175
Gly Gly His Tyr Asp Ala Glu Val Lys Thr Thr Tyr Lys Ala Lys Lys
            180                 185                 190
Pro Val Gln Leu Pro Gly Ala Tyr Asn Val Asp Ile Glu Leu Ala Ile
        195                 200                 205
Thr Ser His Asn Glu Asp Tyr Thr Ile Val Glu Gln Tyr Glu Glu Ala
    210                 215                 220
Glu Gly Glu His Ser Thr Gly Gly Met Asp Glu Leu Tyr Lys
225                 230                 235

<210> SEQ ID NO 54
<211> LENGTH: 238
<212> TYPE: PRT
<213> ORGANISM: Artificial Sequence
<220> FEATURE:
<223> OTHER INFORMATION: MCD19

<400> SEQUENCE: 54

Met Val Ser Lys Gly Glu Glu Asp Asn Met Ala Ile Ile Lys Glu Phe
1               5                  10                  15
Met Arg Phe Lys Val His Met Glu Gly Ser Val Asn Gly His Glu Phe
                20                  25                  30
```

Glu Ile Glu Gly Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
 50                  55                  60

Trp Asp Ile Leu Ser Pro Gln Phe Met Tyr Gly Ser Lys Ala Tyr Val
 65                  70                  75                  80

Lys His Pro Ala Asp Ile Pro Asp Tyr Leu Lys Leu Ser Phe Pro Glu
                 85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Glu Leu Asp Ile
        195                 200                 205

Thr Ser His Asn Glu Asp Tyr Thr Ile Val Glu Gln Tyr Glu Glu Ala
210                 215                 220

Glu Gly Arg His Ser Thr Gly Gly Met Asp Glu Leu Tyr Lys
225                 230                 235

<210> SEQ ID NO 55
<211> LENGTH: 238
<212> TYPE: PRT
<213> ORGANISM: Artificial Sequence
<220> FEATURE:
<223> OTHER INFORMATION: MCD110

<400> SEQUENCE: 55

Met Val Ser Lys Gly Glu Glu Asp Asn Met Ala Ile Ile Lys Glu Phe
 1               5                  10                  15

Met Arg Phe Lys Val His Met Glu Gly Ser Val Asn Gly His Glu Phe
                20                  25                  30

Glu Ile Glu Gly Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
 50                  55                  60

Trp Asp Ile Leu Ser Pro Gln Phe Met Tyr Gly Ser Lys Ala Tyr Val
 65                  70                  75                  80

Lys His Pro Ala Asp Ile Pro Asp Tyr Leu Lys Leu Ser Phe Pro Glu
                 85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
130                 135                 140

Lys Lys Thr Met Gly Trp Glu Ser Ser Glu Arg Met Tyr Pro Glu
145                 150                 155                 160

-continued

Asp Gly Ala Leu Lys Gly Glu Ile Lys Gln Arg Leu Lys Leu Lys Asp
            165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Lys Ser Asp Ile
            195                 200                 205

Thr Ser His Asn Glu Asp Tyr Thr Ile Val Glu Gln Tyr Glu Glu Ala
        210                 215                 220

Glu Gly Glu His Ser Thr Gly Gly Met Asp Glu Leu Tyr Lys
225                 230                 235

<210> SEQ ID NO 56
<211> LENGTH: 238
<212> TYPE: PRT
<213> ORGANISM: Artificial Sequence
<220> FEATURE:
<223> OTHER INFORMATION: MCD111

<400> SEQUENCE: 56

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
            85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
    130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
            165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Glu Ile Lys Leu Asp Ile
            195                 200                 205

Thr Ser His Asn Glu Asp Tyr Thr Ile Val Glu Gln Tyr Glu Glu Ala
        210                 215                 220

Glu Gly Glu His Ser Thr Gly Gly Met Asp Glu Leu Tyr Lys
225                 230                 235

<210> SEQ ID NO 57
<211> LENGTH: 238
<212> TYPE: PRT
<213> ORGANISM: Artificial Sequence
<220> FEATURE:
<223> OTHER INFORMATION: MCD112

<400> SEQUENCE: 57

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
        130                 135                 140

Lys Lys Thr Met Gly Trp Glu Glu Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asp Ile Asp Leu Asp Ile
        195                 200                 205

Thr Ser His Asn Glu Asp Tyr Thr Ile Val Glu Gln Tyr Glu Arg Ala
    210                 215                 220

Glu Gly Gln His Ser Thr Gly Gly Met Asp Glu Leu Tyr Lys
225                 230                 235
```

<210> SEQ ID NO 58
<211> LENGTH: 238
<212> TYPE: PRT
<213> ORGANISM: Artificial Sequence
<220> FEATURE:
<223> OTHER INFORMATION: MCD22

<400> SEQUENCE: 58

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr
        35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125
```

```
Val Lys Leu Arg Gly Thr Asn Phe Pro Ser Asp Gly Pro Val Met Gln
    130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Lys Leu Asp Ile
        195                 200                 205

Thr Ser His Asn Glu Asp Tyr Thr Ile Val Glu Gln Glu Glu Glu Ala
    210                 215                 220

Glu Gly Arg His Ser Thr Gly Gly Met Asp Glu Leu Tyr Lys
225                 230                 235

<210> SEQ ID NO 59
<211> LENGTH: 238
<212> TYPE: PRT
<213> ORGANISM: Artificial Sequence
<220> FEATURE:
<223> OTHER INFORMATION: MCD23

<400> SEQUENCE: 59

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
        50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
    130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Glu Leu Glu Ile
        195                 200                 205

Thr Ser His Asn Glu Asp Tyr Thr Ile Val Glu Gln Glu Glu Glu Ala
    210                 215                 220

Glu Gly Arg His Ser Thr Gly Gly Met Asp Glu Leu Tyr Lys
225                 230                 235

<210> SEQ ID NO 60
```

```
<211> LENGTH: 238
<212> TYPE: PRT
<213> ORGANISM: Artificial Sequence
<220> FEATURE:
<223> OTHER INFORMATION: MCD24

<400> SEQUENCE: 60

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Gly Arg Pro Tyr Glu Gly Thr
            35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
                180                 185                 190

Pro Val Gln Leu Pro Gly Ala Tyr Asn Val Asn Ile Glu Leu Gln Ile
            195                 200                 205

Thr Ser His Asn Glu Asp Tyr Thr Ile Val Glu Gln Glu Glu Glu Ala
    210                 215                 220

Glu Gly Arg His Ser Thr Gly Gly Met Asp Glu Leu Tyr Lys
225                 230                 235

<210> SEQ ID NO 61
<211> LENGTH: 238
<212> TYPE: PRT
<213> ORGANISM: Artificial Sequence
<220> FEATURE:
<223> OTHER INFORMATION: MCD25

<400> SEQUENCE: 61

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
```

```
                    85                  90                  95
Gly Phe Lys Trp Glu Arg Val Met Asn Phe Glu Asp Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
        130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Glu Leu Asn Ile
        195                 200                 205

Thr Ser His Asn Glu Asp Tyr Thr Ile Val Glu Gln Glu Glu Glu Ala
    210                 215                 220

Glu Gly Arg His Ser Thr Gly Gly Met Asp Glu Leu Tyr Lys
225                 230                 235

<210> SEQ ID NO 62
<211> LENGTH: 238
<212> TYPE: PRT
<213> ORGANISM: Artificial Sequence
<220> FEATURE:
<223> OTHER INFORMATION: MCD26

<400> SEQUENCE: 62

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
        50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
                100                 105                 110

Thr Val Thr Gln Asp Ser Ser Leu Gln Asp Gly Glu Phe Ile Tyr Lys
            115                 120                 125

Val Lys Leu Arg Gly Thr Asn Phe Pro Ser Asp Gly Pro Val Met Gln
        130                 135                 140

Lys Lys Thr Met Gly Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Lys Leu Asp Ile
        195                 200                 205

Thr Ser His Asn Glu Asp Tyr Thr Ile Val Glu Gln Glu Glu Glu Ala
```

Glu Gly Arg His Ser Thr Gly Gly Met Asp Glu Leu Tyr Lys
225                 230                 235

<210> SEQ ID NO 63
<211> LENGTH: 238
<212> TYPE: PRT
<213> ORGANISM: Artificial Sequence
<220> FEATURE:
<223> OTHER INFORMATION: MCP4

<400> SEQUENCE: 63

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr
            35                  40                  45

Gln Thr Ala Lys Leu Lys Val Thr Lys Gly Gly Pro Leu Pro Phe Ala
    50                  55                  60

Trp Asp Ile Leu Ser Pro Gln Phe Met Tyr Gly Ser Lys Ala Tyr Val
65                  70                  75                  80

Lys His Pro Ala Asp Ile Pro Asp Tyr Leu Lys Leu Ser Phe Pro Glu
                85                  90                  95

Gly Phe Lys Trp Glu Arg Val Met Asn Phe Glu Asp Gly Gly Val Val
            100                 105                 110

Thr Val Thr Gln Asp Ser Ser Leu Gln Asp Gly Glu Phe Ile Tyr Lys
        115                 120                 125

Val Lys Leu Arg Gly Thr Asn Phe Pro Ser Asp Gly Pro Val Met Gln
130                 135                 140

Lys Lys Thr Met Glu Trp Glu Ala Ser Ser Glu Arg Met Tyr Pro Glu
145                 150                 155                 160

Asp Gly Ala Leu Lys Gly Glu Ile Lys Gln Arg Leu Lys Leu Lys Asp
                165                 170                 175

Gly Gly His Tyr Asp Ala Glu Val Lys Thr Thr Tyr Lys Ala Lys Lys
            180                 185                 190

Pro Val Gln Leu Pro Gly Ala Tyr Asn Val Asn Ile Lys Leu Asp Ile
        195                 200                 205

Thr Ser His Asn Glu Asp Tyr Thr Ile Val Glu Gln Tyr Glu Arg Ala
    210                 215                 220

Glu Gly Arg His Ser Thr Gly Gly Met Asp Glu Leu Tyr Lys
225                 230                 235

<210> SEQ ID NO 64
<211> LENGTH: 18
<212> TYPE: PRT
<213> ORGANISM: Artificial Sequence
<220> FEATURE:
<223> OTHER INFORMATION: Calreticulin ER-speciic Tag

<400> SEQUENCE: 64

Met Leu Leu Ser Val Pro Leu Leu Leu Gly Leu Leu Gly Leu Ala Ala
1               5                   10                  15

Ala Asp

<210> SEQ ID NO 65
<211> LENGTH: 804
<212> TYPE: DNA

<213> ORGANISM: Artificial Sequence
<220> FEATURE:
<223> OTHER INFORMATION: CatchER-T

<400> SEQUENCE: 65

```
atgctgctat ccgtgccgtt gctgctcggc ctcctcggcc tggccgctgc agacggatcc    60
gggccctcta gaatggtgag caagggcgag gagctgttca ccggggtggt gcccatcctg   120
gtcgagctgg acggcgacgt aaacggccac aagttcagca ggtccggcga gggcgagggc   180
gatgccacca acggcaagct gaccctgaag ttcatctgca ccaccggcaa gctgcccgtg   240
ccctggccca cctcgtgac cacccgacc tacggcgtgc agtgcttcag ccgctacccc     300
gaccacatga agcagcacga cttcttcaag tccgccatgc ccgaaggcta cgtccaggag   360
cgcaccatct tcttcaagga cgacggcaac tacaagaccc gcgccgaggt gaagttcgag   420
ggcgacaccc tggtgaaccg catcgagctg aagggcatcg acttcaagga ggacggcaac   480
atcctggggc acaagctgga gtacaactac aacgagcaca cgtctatat cacggccgac    540
aagcagaaga acggcatcaa ggcgaacttc aagatccgcc acaacatcga ggacggcagc   600
gtgcagctcg ccgaccacta ccagcagaac accccatcg cgggggccc cgtgctgctg     660
cccgacaacc actacctgga caccgaatcc gccctgagca agacccccaa cgagaagcgc   720
gatcacatgg tcctgctgga ggaggtggag gccgccggga tcactctcgg catggacgag   780
ctgtacaaga aggacgagct gtaa                                          804
```

<210> SEQ ID NO 66
<211> LENGTH: 804
<212> TYPE: DNA
<213> ORGANISM: Artificial Sequence
<220> FEATURE:
<223> OTHER INFORMATION: CatchER-T Y39N N149E

<400> SEQUENCE: 66

```
atgctgctat ccgtgccgtt gctgctcggc ctcctcggcc tggccgctgc agacggatcc    60
gggccctcta gaatggtgag caagggcgag gagctgttca ccggggtggt gcccatcctg   120
gtcgagctgg acggcgacgt aaacggccac aagttcagcg tgtccggcga gggcgagggc   180
gatgccacca acggcaagct gaccctgaag ttcatctgca ccaccggcaa gctgcccgtg   240
ccctggccca cctcgtgac cacccgacc tacggcgtgc agtgcttcag ccgctacccc     300
gaccacatga agcagcacga cttcttcaag tccgccatgc ccgaaggcta cgtccaggag   360
cgcaccatct tcttcaagga cgacggcaac tacaagaccc gcgccgaggt gaagttcgag   420
ggcgacaccc tggtgaaccg catcgagctg aagggcatcg acttcaagga ggacggcaac   480
atcctggggc acaagctgga gtacaactac aacgagcacg aggtctatat cacggccgac   540
aagcagaaga acggcatcaa ggcgaacttc aagatccgcc acaacatcga ggacggcagc   600
gtgcagctcg ccgaccacta ccagcagaac accccatcg cgacggccc cgtgctgctg     660
cccgacaacc actacctgga caccgaatcc gccctgagca agacccccaa cgagaagcgc   720
gatcacatgg tcctgctgga ggaggtggag gccgccggga tcactctcgg catggacgag   780
ctgtacaaga aggacgagct gtaa                                          804
```

<210> SEQ ID NO 67
<211> LENGTH: 795
<212> TYPE: DNA
<213> ORGANISM: Artificial Sequence
<220> FEATURE:
<223> OTHER INFORMATION: CatchER-T Y39N (CatchER-T1)

```
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t

<400> SEQUENCE: 67
gtgccgttgc tgctcggcct cctcggcctg gccgctgcag acggatccgg gccctctaga      60
atggtgagca agggcgagga gctgttcacc ggggtggtgc ccatcctggt cgagctggac     120
ggcgacgtaa acggccacaa gttcagcgtg tccggcgagg gcgagggcga tgccaccaac     180
ggcaagctga ccctgaagtt catctgcacc accggcaagc tgcccgtgcc ctggcccacc     240
ctcgtgacca ccctgaccta cggcgtgcag tgcttcagcc gctaccccga ccacatgaag     300
cagcacgact tcttcaagtc cgccatgccc gaaggctacg tccaggagcg caccatcttc     360
ttcaaggacg acggcaacta caagacccgc gccgaggtga agttcgaggg cgacaccctg     420
gtgaaccgca tcgagctgaa gggcatcgac ttcaaggagg acggcaacat cctggggcac     480
aagctggagt acaactacaa cgagcacaac gtctatatca cggccgacaa gcagaagaac     540
ggcatcaagg cgaacttcaa gatccgccac aacatcgagg acggcggcgt gcagctcgcc     600
gaccactacc agcagaacac ccccatcggc gacggccccg tgctgctgcc cgacaaccac     660
tacctggaca ccgaatccgc cctgagcaaa gaccccaacg agaagcgcga tcacatggtt     720
cctgctggga ggangtggag gccgccggga tcactctcgg catggacgag ctgtacnaaa     780
aaggacgagc tgtaa                                                      795

<210> SEQ ID NO 68
<211> LENGTH: 804
<212> TYPE: DNA
<213> ORGANISM: Artificial Sequence
<220> FEATURE:
<223> OTHER INFORMATION: CatchER-T S30R (CatchER-T2)

<400> SEQUENCE: 68
atgctgctat ccgtgccgtt gctgctcggc ctcctcggcc tggccgctgc agacggatcc      60
gggccctcta gaatggtgag caagggcgag gagctgttca ccggggtggt gcccatcctg     120
gtcgagctgg acggcgacgt aaacggccac aagttcagcg tgcgcggcga gggcgagggc     180
gatgccacct acggcaagct gaccctgaag ttcatctgca ccaccggcaa gctgcccgtg     240
ccctggccca ccctcgtgac caccctgacc tacggcgtgc agtgcttcag ccgctacccc     300
gaccacatga gcagcacga cttcttcaag tccgccatgc ccgaaggcta cgtccaggag     360
cgcaccatct tcttcaagga cgacggcaac tacaagaccc gcgccgaggt gaagttcgag     420
ggcgacaccc tggtgaaccg catcgagctg aagggcatcg acttcaagga ggacggcaac     480 atcctgggc acaagctgga gtacaactac aacgagcaca acgtctatat cacggccgac     540
aagcagaaga acggcatcaa ggcgaacttc aagatccgcc acaacatcga ggacggcagc     600
gtgcagctcg ccgaccacta ccagcagaac acccccatcg gcgacggccc cgtgctgctg     660
cccgacaacc actacctgga caccgaatcc gccctgagca agaccccaa cgagaagcgc     720 gatcacatgg tcctgctgga ggaggtggag gccgccggga tcactctcgg catggacgag     780
ctgtacaaga aggacgagct gtaa                                             804

<210> SEQ ID NO 69
```

<211> LENGTH: 804
<212> TYPE: DNA
<213> ORGANISM: Artificial Sequence
<220> FEATURE:
<223> OTHER INFORMATION: CatchER-T s30R Y39N (CatchER-T')

<400> SEQUENCE: 69

```
atgctgctat ccgtgccgtt gctgctcggc ctcctcggcc tggccgctgc agacggatcc    60
gggccctcta gaatggtgag caagggcgag gagctgttca ccggggtggt gcccatcctg   120
gtcgagctgg acggcgacgt aaacggccac aagttcagcg tgcgcggcga gggcgagggc   180
gatgccacca acggcaagct gaccctgaag ttcatctgca ccaccggcaa gctgcccgtg   240
ccctggccca ccctcgtgac caccctgacc tacggcgtgc agtgcttcag ccgctacccc   300
gaccacatga gcagcacga cttcttcaag tccgccatgc ccgaaggcta cgtccaggag   360
cgcaccatct tcttcaagga cgacggcaac tacaagaccc gcgccgaggt gaagttcgag   420
ggcgacaccc tggtgaaccg catcgagctg aagggcatcg acttcaagga ggacggcaac   480
atcctggggc acaagctgga gtacaactac aacgagcaca acgtctatat cacggccgac   540
aagcagaaga acggcatcaa ggcgaacttc aagatccgcc acaacatcga ggacggcagc   600
gtgcagctcg ccgaccacta ccagcagaac acccccatcg gcgacggccc cgtgctgctg   660
cccgacaacc actacctgga caccgaatcc gccctgagca agacccccaa cgagaagcgc   720
gatcacatgg tcctgctgga ggaggtggag gccgccggga tcactctcgg catggacgag   780
ctgtacaaga aggacgagct gtaa                                         804
```

<210> SEQ ID NO 70
<211> LENGTH: 720
<212> TYPE: DNA
<213> ORGANISM: Artificial Sequence
<220> FEATURE:
<223> OTHER INFORMATION: CatchER-JP45
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t

<400> SEQUENCE: 70

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggcac   420
aagctggagt acaactacaa cgagcacaac gtctatatca cggccgacaa gcagaagaac   480
ggcatcaagg cgaacttcaa gatccgccac aacatcgagg acggcagcgt gcagctcgcc   540
gaccactacc agcagaacac ccccatcggc gacggccccg tgctgctgcc cgacaaccac   600
tacctggnca ccgaatccgc cctgagcaaa gacccccaac gagaagcgcg atcacatggtc   660
ctgctggagg aggtggaggc cgccgggntc actctcggca tggacgagct gtacaagtaa   720
```

```
<210> SEQ ID NO 71
<211> LENGTH: 267
<212> TYPE: PRT
<213> ORGANISM: Artificial Sequence
<220> FEATURE:
<223> OTHER INFORMATION: CatchER-T Y39N N149E

<400> SEQUENCE: 71

Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Asn
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Glu His Glu Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Asp Thr Glu Ser Ala Leu Ser Lys Asp Pro Asn Glu Lys Arg
225                 230                 235                 240

Asp His Met Val Leu Leu Glu Val Glu Ala Ala Gly Ile Thr Leu
                245                 250                 255

Gly Met Asp Glu Leu Tyr Lys Lys Asp Glu Leu
            260                 265

<210> SEQ ID NO 72
<211> LENGTH: 263
<212> TYPE: PRT
<213> ORGANISM: Artificial Sequence
<220> FEATURE:
<223> OTHER INFORMATION: CatchER-T Y39N (CatchER-T1)
<220> FEATURE:
<221> NAME/KEY: MISC_FEATURE
<222> LOCATION: (20)..(20)
<223> OTHER INFORMATION: Xaa cab be any naturally ocurring amino acid

<400> SEQUENCE: 72

Val Pro Leu Leu Leu Gly Leu Leu Gly Leu Ala Ala Ala Asp Gly Ser
1               5                   10                  15

Gly Pro Ser Xaa Met Val Ser Lys Gly Glu Glu Leu Phe Thr Gly Val
            20                  25                  30
```

Val Pro Ile Leu Val Glu Leu Asp Gly Asp Val Asn Gly His Lys Phe
            35                  40                  45

Ser Val Ser Gly Glu Gly Glu Gly Asp Ala Thr Asn Gly Lys Leu Thr
 50                  55                  60

Leu Lys Phe Ile Cys Thr Thr Gly Lys Leu Pro Val Pro Trp Pro Thr
 65                  70                  75                  80

Leu Val Thr Thr Leu Thr Tyr Gly Val Gln Cys Phe Ser Arg Tyr Pro
                 85                  90                  95

Asp His Met Lys Gln His Asp Phe Phe Lys Ser Ala Met Pro Glu Gly
                100                 105                 110

Tyr Val Gln Glu Arg Thr Ile Phe Phe Lys Asp Asp Gly Asn Tyr Lys
            115                 120                 125

Thr Arg Ala Glu Val Lys Phe Glu Gly Asp Thr Leu Val Asn Arg Ile
        130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Glu His Asn Val Tyr Ile Thr Ala Asp
                165                 170                 175

Lys Gln Lys Asn Gly Ile Lys Ala Asn Phe Lys Ile Arg His Asn Ile
            180                 185                 190

Glu Asp Gly Gly Val Gln Leu Ala Asp His Tyr Gln Gln Asn Thr Pro
        195                 200                 205

Ile Gly Asp Gly Pro Val Leu Leu Pro Asp Asn His Tyr Leu Asp Thr
        210                 215                 220

Glu Ser Ala Leu Ser Lys Asp Pro Asn Glu Lys Arg Asp His Met Val
225                 230                 235                 240

Leu Leu Glu Glu Val Glu Ala Ala Gly Ile Thr Leu Gly Met Asp Glu
                245                 250                 255

Leu Tyr Lys Lys Asp Glu Leu
            260

<210> SEQ ID NO 73
<211> LENGTH: 267
<212> TYPE: PRT
<213> ORGANISM: Artificial Sequence
<220> FEATURE:
<223> OTHER INFORMATION: CatchER-T S30R (CatchER-T2)

<400> SEQUENCE: 73

Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Val Asn
            35                  40                  45

Gly His Lys Phe Ser Val Arg Gly Glu Gly Glu Gly Asp Ala Thr Tyr
         50                  55                  60

Gly Lys Leu Thr Leu Lys Phe Ile Cys Thr Thr Gly Lys Leu Pro Val
 65                  70                  75                  80

Pro Trp Pro Thr Leu Val Thr Thr Leu Thr Tyr Gly Val Gln Cys Phe
                 85                  90                  95

Ser Arg Tyr Pro Asp His Met Lys Gln His Asp Phe Phe Lys Ser Ala
                100                 105                 110

Met Pro Glu Gly Tyr Val Gln Glu Arg Thr Ile Phe Phe Lys Asp Asp
            115                 120                 125

```
Gly Asn Tyr Lys Thr Arg Ala Glu Val Lys Phe Glu Gly Asp Thr Leu
        130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Glu His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Asp Thr Glu Ser Ala Leu Ser Lys Asp Pro Asn Glu Lys Arg
225                 230                 235                 240

Asp His Met Val Leu Leu Glu Glu Val Glu Ala Ala Gly Ile Thr Leu
                245                 250                 255

Gly Met Asp Glu Leu Tyr Lys Lys Asp Glu Leu
            260                 265

<210> SEQ ID NO 74
<211> LENGTH: 267
<212> TYPE: PRT
<213> ORGANISM: Artificial Sequence
<220> FEATURE:
<223> OTHER INFORMATION: CatchER-T S30R Y39N (CatchER-T')
<220> FEATURE:
<221> NAME/KEY: MISC_FEATURE
<222> LOCATION: (264)..(265)
<223> OTHER INFORMATION: Xaa can be any naturally occurring amino acid

<400> SEQUENCE: 74

Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Arg Gly Glu Gly Glu Gly Asp Ala Thr Asn
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Glu His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
```

```
                195                 200                 205
Gln Asn Thr Pro Ile Gly Asp Gly Pro Val Leu Leu Pro Asp Asn His
        210                 215                 220
Tyr Leu Asp Thr Glu Ser Ala Leu Ser Lys Asp Pro Asn Glu Lys Arg
225                 230                 235                 240
Asp His Met Val Leu Glu Glu Val Glu Ala Ala Gly Ile Thr Leu
                245                 250                 255
Gly Met Asp Glu Leu Tyr Lys Xaa Xaa Glu Leu
        260                 265
```

<210> SEQ ID NO 75
<211> LENGTH: 239
<212> TYPE: PRT
<213> ORGANISM: Artificial Sequence
<220> FEATURE:
<223> OTHER INFORMATION: CatchER-JP45
<220> FEATURE:
<221> NAME/KEY: MISC_FEATURE
<222> LOCATION: (203)..(203)
<223> OTHER INFORMATION: Xaa can be any naturally occurring amino acid
<220> FEATURE:
<221> NAME/KEY: MISC_FEATURE
<222> LOCATION: (230)..(230)
<223> OTHER INFORMATION: Xaa can be any naturally occurring amino acid

<400> SEQUENCE: 75

```
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
130                 135                 140
Asn Tyr Asn Glu His Asn Val Tyr Ile Thr Ala Asp Lys Gln Lys Asn
145                 150                 155                 160
Gly Ile Lys Ala Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Xaa Thr Glu Ser Ala Leu
        195                 200                 205
Ser Lys Asp Pro Asn Glu Lys Arg Asp His Met Val Leu Leu Glu Glu
    210                 215                 220
Val Glu Ala Ala Gly Xaa Thr Leu Gly Met Asp Glu Leu Tyr Lys
225                 230                 235
```

<210> SEQ ID NO 76

```
<211> LENGTH: 47
<212> TYPE: PRT
<213> ORGANISM: Artificial Sequence
<220> FEATURE:
<223> OTHER INFORMATION: eZ5 from ryanodine receptor 4551-4597 (Genbank
      X15209)

<400> SEQUENCE: 76

Phe Leu Asn Tyr Leu Ser Arg Asn Phe Tyr Thr Leu Arg Phe Leu Ala
1               5                   10                  15

Leu Phe Leu Ala Phe Ala Ile Asn Phe Ile Leu Leu Phe Tyr Lys Val
                20                  25                  30

Ser Asp Ser Pro Pro Gly Glu Asp Asp Met Glu Gly Ser Ala Ala
            35                  40                  45

<210> SEQ ID NO 77
<211> LENGTH: 37
<212> TYPE: PRT
<213> ORGANISM: Artificial Sequence
<220> FEATURE:
<223> OTHER INFORMATION: Z10 from ryanodine receptor 490-4943 (Genbank
      X15209)

<400> SEQUENCE: 77

Asp Glu Tyr Glu Leu Tyr Arg Val Val Phe Asp Ile Thr Phe Phe Phe
1               5                   10                  15

Phe Val Ile Val Ile Leu Leu Ala Ile Ile Gln Gly Leu Ile Ile Asp
                20                  25                  30

Ala Phe Gly Glu Leu
        35

<210> SEQ ID NO 78
<211> LENGTH: 23
<212> TYPE: PRT
<213> ORGANISM: Artificial Sequence
<220> FEATURE:
<223> OTHER INFORMATION: Z5 from ryanodine receptor 4551-4597 (Genbank
      X15209)

<400> SEQUENCE: 78

Thr Leu Arg Phe Leu Ala Leu Phe Leu Ala Phe Ala Ile Asn Phe Ile
1               5                   10                  15

Leu Leu Phe Tyr Lys Val Ser
                20

<210> SEQ ID NO 79
<211> LENGTH: 331
<212> TYPE: PRT
<213> ORGANISM: Artificial Sequence
<220> FEATURE:
<223> OTHER INFORMATION: Z10Cat

<400> SEQUENCE: 79

Met Asp Glu Tyr Glu Leu Tyr Arg Val Val Phe Asp Ile Thr Phe Phe
1               5                   10                  15

Phe Phe Val Ile Val Ile Leu Leu Ala Ile Ile Gln Gly Leu Ile Ile
                20                  25                  30

Asp Ala Phe Gly Glu Leu Pro Thr Met Val Ser Lys Gly Glu Glu
            35                  40                  45

Leu Phe Thr Gly Val Val Pro Ile Leu Val Glu Leu Asp Gly Asp Val
    50                  55                  60

Asn Gly His Lys Phe Ser Val Ser Gly Glu Gly Glu Gly Asp Ala Thr
65                  70                  75                  80
```

-continued

```
Tyr Gly Lys Leu Thr Leu Lys Phe Ile Cys Thr Thr Gly Lys Leu Pro
                85                  90                  95
Val Pro Trp Pro Thr Leu Val Thr Thr Leu Thr Tyr Gly Val Gln Cys
            100                 105                 110
Phe Ser Arg Tyr Pro Asp His Met Lys Gln His Asp Phe Phe Lys Ser
        115                 120                 125
Ala Met Pro Glu Gly Tyr Val Gln Glu Arg Thr Ile Phe Phe Lys Asp
130                 135                 140
Asp Gly Asn Tyr Lys Thr Arg Ala Glu Val Lys Phe Glu Gly Asp Thr
145                 150                 155                 160
Leu Val Asn Arg Ile Glu Leu Lys Gly Ile Asp Phe Lys Glu Asp Gly
                165                 170                 175
Asn Ile Leu Gly His Lys Leu Glu Tyr Asn Tyr Asn Glu His Asn Val
            180                 185                 190
Tyr Ile Thr Ala Asp Lys Gln Lys Asn Gly Ile Lys Ala Asn Phe Lys
        195                 200                 205
Ile Arg His Asn Ile Glu Asp Gly Ser Val Gln Leu Ala Asp His Tyr
210                 215                 220
Gln Gln Asn Thr Pro Ile Gly Asp Gly Pro Val Leu Leu Pro Asp Asn
225                 230                 235                 240
His Tyr Leu Asp Thr Glu Ser Ala Leu Ser Lys Asp Pro Asn Glu Lys
                245                 250                 255
Arg Asp His Met Val Leu Leu Glu Val Glu Ala Ala Gly Ile Thr
            260                 265                 270
Leu Gly Met Asp Glu Leu Tyr Lys Ser Leu Pro Ala Phe Leu Asn Tyr
        275                 280                 285
Leu Ser Arg Asn Phe Tyr Thr Leu Arg Phe Leu Ala Leu Phe Leu Ala
290                 295                 300
Phe Ala Ile Asn Phe Ile Leu Leu Phe Tyr Lys Val Ser Asp Ser Pro
305                 310                 315                 320
Pro Gly Glu Asp Asp Met Glu Gly Ser Ala Ala
                325                 330
```

<210> SEQ ID NO 80
<211> LENGTH: 262
<212> TYPE: PRT
<213> ORGANISM: Artificial Sequence
<220> FEATURE:
<223> OTHER INFORMATION: CatZ5

<400> SEQUENCE: 80

```
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
        50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Glu His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Asp Thr Glu Ser Ala Leu
            195                 200                 205

Ser Lys Asp Pro Asn Glu Lys Arg Asp His Met Val Leu Leu Glu Glu
        210                 215                 220

Val Glu Ala Ala Gly Ile Thr Leu Gly Met Asp Glu Leu Tyr Lys Thr
225                 230                 235                 240

Leu Arg Phe Leu Ala Leu Phe Leu Ala Phe Ala Ile Asn Phe Ile Leu
                245                 250                 255

Leu Phe Tyr Lys Val Ser
            260

<210> SEQ ID NO 81
<211> LENGTH: 286
<212> TYPE: PRT
<213> ORGANISM: Artificial Sequence
<220> FEATURE:
<223> OTHER INFORMATION: CateZ5

<400> SEQUENCE: 81

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Glu His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Asp Thr Glu Ser Ala Leu
            195                 200                 205
```

Ser Lys Asp Pro Asn Glu Lys Arg Asp His Met Val Leu Leu Glu Glu
210                 215                 220

Val Glu Ala Ala Gly Ile Thr Leu Gly Met Asp Glu Leu Tyr Lys Phe
225                 230                 235                 240

Leu Asn Tyr Leu Ser Arg Asn Phe Tyr Thr Leu Arg Phe Leu Ala Leu
            245                 250                 255

Phe Leu Ala Phe Ala Ile Asn Phe Ile Leu Leu Phe Tyr Lys Val Ser
            260                 265                 270

Asp Ser Pro Pro Gly Glu Asp Met Glu Gly Ser Ala Ala
            275                 280                 285

<210> SEQ ID NO 82
<211> LENGTH: 290
<212> TYPE: PRT
<213> ORGANISM: Artificial Sequence
<220> FEATURE:
<223> OTHER INFORMATION: CatLeZ5
<220> FEATURE:
<221> NAME/KEY: MISC_FEATURE
<222> LOCATION: (263)..(263)
<223> OTHER INFORMATION: Xaa can be any naturally occurring amino acid
<220> FEATURE:
<221> NAME/KEY: MISC_FEATURE
<222> LOCATION: (286)..(286)
<223> OTHER INFORMATION: Xaa can be any naturally occurring amino acid

<400> SEQUENCE: 82

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Glu His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Asp Thr Glu Ser Ala Leu
        195                 200                 205

Ser Lys Asp Pro Asn Glu Lys Arg Asp His Met Val Leu Leu Glu Glu
210                 215                 220

Val Glu Ala Ala Gly Ile Thr Leu Gly Met Asp Glu Leu Tyr Lys Ser
225                 230                 235                 240

```
Leu Pro Ala Phe Leu Asn Tyr Leu Ser Arg Asn Phe Tyr Thr Leu Arg
                245                 250                 255

Phe Leu Ala Leu Phe Leu Xaa Phe Ala Ile Asn Phe Ile Leu Leu Phe
            260                 265                 270

Tyr Lys Val Ser Asp Ser Pro Pro Gly Glu Asp Asp Met Xaa Gly Ser
        275                 280                 285

Ala Ala
    290

<210> SEQ ID NO 83
<211> LENGTH: 4
<212> TYPE: PRT
<213> ORGANISM: Artificial Sequence
<220> FEATURE:
<223> OTHER INFORMATION: ER retention sequence

<400> SEQUENCE: 83

Lys Asp Glu Leu
1

<210> SEQ ID NO 84
<211> LENGTH: 5
<212> TYPE: PRT
<213> ORGANISM: Artificial Sequence
<220> FEATURE:
<223> OTHER INFORMATION: linker sequence

<400> SEQUENCE: 84

Gly Gly Ser Gly Gly
1               5

<210> SEQ ID NO 85
<211> LENGTH: 10
<212> TYPE: DNA
<213> ORGANISM: Artificial Sequence
<220> FEATURE:
<223> OTHER INFORMATION: Kozak sequence

<400> SEQUENCE: 85
gccaccatgg                                                                10

<210> SEQ ID NO 86
<211> LENGTH: 4
<212> TYPE: PRT
<213> ORGANISM: Artificial Sequence
<220> FEATURE:
<223> OTHER INFORMATION: linker sequence

<400> SEQUENCE: 86

Ser Leu Pro Ala
1
```